(12) United States Patent
Malaviya et al.

(10) Patent No.: US 8,092,529 B2
(45) Date of Patent: Jan. 10, 2012

(54) MENISCUS REGENERATION DEVICE

(75) Inventors: Prasanna Malaviya, Ft. Wayne, IN (US); Herbert Eugene Schwartz, Ft. Wayne, IN (US); Terrence David Whalen, Leesburg, IN (US); Mark Joseph Pelo, Macy, IN (US); Philip Joseph Jenks, Warsaw, IN (US); Pamela Lynn Plouhar, South Bend, IN (US); Jerry Lee Lower, Bourbon, IN (US)

(73) Assignee: DePuy Products, Inc., Warsaw, IN (US)

( * ) Notice: Subject to any disclaimer, the term of this patent is extended or adjusted under 35 U.S.C. 154(b) by 693 days.

(21) Appl. No.: 10/195,794

(22) Filed: Jul. 15, 2002

(65) Prior Publication Data

US 2003/0036797 A1 Feb. 20, 2003

Related U.S. Application Data

(60) Provisional application No. 60/388,713, filed on Jun. 14, 2002, provisional application No. 60/305,786, filed on Jul. 16, 2001.

(51) Int. Cl.
*A61F 2/08* (2006.01)
(52) U.S. Cl. ............... 623/14.12; 623/13.17; 623/23.63; 623/23.72
(58) Field of Classification Search ............... 623/23.52, 623/23.63, 23.72, 14.12, 13.17
See application file for complete search history.

(56) References Cited

U.S. PATENT DOCUMENTS

| | | | |
|---|---|---|---|
| 3,272,204 A | 9/1966 | Artandi et al. |
| 3,562,820 A | 2/1971 | Braun |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,352,463 A | 10/1982 | Baker |
| 4,400,833 A | 8/1983 | Kurland |
| 4,418,691 A | 12/1983 | Yannas et al. |
| 4,610,397 A | 9/1986 | Fischer et al. |
| 4,642,120 A | 2/1987 | Nevo et al. |
| 4,669,473 A | 6/1987 | Richards et al. |
| 4,703,108 A | 10/1987 | Silver et al. |
| 4,705,040 A | 11/1987 | Mueller et al. |

(Continued)

FOREIGN PATENT DOCUMENTS

EP 0 446 105 A2 1/1992

(Continued)

OTHER PUBLICATIONS

On-line Medical Dictionary definition of "extracellular matrix" located at http://cancerweb.ncl.ac.uk/cgi-bin/omd?extracellular+matrix.*

(Continued)

*Primary Examiner* — Paul Prebilic
(74) *Attorney, Agent, or Firm* — Barnes & Thornburg LLP

(57) ABSTRACT

Methods and devices are provided for regenerating a meniscus. The devices comprise a layer of toughened naturally occurring extracellular matrix. The devices may, optionally, further comprise a biologic material to provide a framework for meniscus regeneration. The methods comprise the steps of removing a portion of a meniscus to provide a space, and inserting a device comprising a layer of toughened naturally occurring extracellular matrix into the space.

25 Claims, 27 Drawing Sheets

U.S. PATENT DOCUMENTS

| | | | |
|---|---|---|---|
| 4,741,330 A | 5/1988 | Hayhurst | |
| 4,750,492 A | 6/1988 | Jacobs | |
| 4,775,361 A * | 10/1988 | Jacques et al. | 604/20 |
| 4,846,835 A | 7/1989 | Grande | |
| 4,873,976 A | 10/1989 | Schreiber | |
| 4,880,429 A | 11/1989 | Stone | |
| 4,902,508 A | 2/1990 | Badylak et al. | |
| 4,917,084 A * | 4/1990 | Sinofsky | 606/7 |
| 4,919,667 A | 4/1990 | Richmond | |
| 4,956,178 A | 9/1990 | Badylak et al. | |
| 4,956,179 A | 9/1990 | Bamberg et al. | |
| 4,976,715 A | 12/1990 | Bays et al. | |
| 5,007,934 A | 4/1991 | Stone | |
| 5,013,323 A * | 5/1991 | Kobayashi et al. | 623/23.56 |
| 5,061,286 A | 10/1991 | Lyle | |
| 5,102,421 A | 4/1992 | Anspach, Jr. | |
| 5,108,438 A | 4/1992 | Stone | |
| 5,116,374 A | 5/1992 | Stone | |
| 5,128,326 A | 7/1992 | Balazs et al. | |
| RE34,021 E | 8/1992 | Mueller et al. | |
| 5,227,627 A * | 7/1993 | Gamarnik et al. | 250/252.1 |
| 5,236,431 A | 8/1993 | Gogolewski et al. | |
| 5,246,441 A | 9/1993 | Ross et al. | |
| 5,258,015 A | 11/1993 | Li et al. | |
| 5,269,809 A | 12/1993 | Hayhurst et al. | |
| 5,275,826 A | 1/1994 | Badylak et al. | |
| 5,281,422 A | 1/1994 | Badylak et al. | |
| 5,306,311 A | 4/1994 | Stone et al. | |
| 5,320,633 A | 6/1994 | Allen et al. | |
| 5,329,846 A * | 7/1994 | Bonutti | 100/50 |
| 5,341,292 A * | 8/1994 | Zamenhof | 600/425 |
| 5,350,583 A | 9/1994 | Yoshizato et al. | |
| 5,352,463 A | 10/1994 | Badylak et al. | |
| 5,372,821 A | 12/1994 | Badylak et al. | |
| 5,374,268 A | 12/1994 | Sander | |
| 5,376,118 A | 12/1994 | Kaplan et al. | |
| 5,380,334 A | 1/1995 | Torrier et al. | |
| 5,445,833 A | 8/1995 | Badylak et al. | |
| 5,447,940 A | 9/1995 | Harvey et al. | |
| 5,460,962 A | 10/1995 | Kemp | |
| 5,464,929 A | 11/1995 | Bezwada et al. | |
| 5,479,033 A | 12/1995 | Baca et al. | |
| 5,514,181 A | 5/1996 | Light et al. | |
| 5,516,533 A | 5/1996 | Badylak et al. | |
| 5,520,691 A | 5/1996 | Branch | |
| 5,545,178 A | 8/1996 | Kensey et al. | |
| 5,554,389 A | 9/1996 | Badylak et al. | |
| 5,569,252 A | 10/1996 | Justin et al. | |
| 5,573,784 A | 11/1996 | Badylak et al. | |
| 5,591,234 A | 1/1997 | Kirsch | |
| 5,593,441 A | 1/1997 | Lichtenstein et al. | |
| 5,595,621 A | 1/1997 | Light et al. | |
| 5,595,751 A | 1/1997 | Bezwada et al. | |
| 5,597,579 A | 1/1997 | Bezwada et al. | |
| 5,601,558 A | 2/1997 | Torrie et al. | |
| 5,607,687 A | 3/1997 | Bezwada et al. | |
| 5,618,552 A | 4/1997 | Bezwada et al. | |
| 5,620,698 A | 4/1997 | Bezwada et al. | |
| 5,626,614 A | 5/1997 | Hart | |
| 5,630,824 A | 5/1997 | Hart | |
| 5,632,745 A | 5/1997 | Schwartz | |
| 5,641,518 A | 6/1997 | Badylak et al. | |
| 5,645,850 A | 7/1997 | Bezwada et al. | |
| 5,645,860 A | 7/1997 | Knapp, Jr. et al. | |
| 5,648,088 A | 7/1997 | Bezwada et al. | |
| 5,660,225 A | 8/1997 | Saffran | |
| 5,668,288 A | 9/1997 | Storey et al. | |
| 5,669,912 A | 9/1997 | Spetzler | |
| 5,677,355 A | 10/1997 | Shalaby et al. | |
| 5,681,353 A | 10/1997 | Li et al. | |
| 5,693,085 A | 12/1997 | Buirge et al. | |
| 5,695,998 A | 12/1997 | Badylak et al. | |
| 5,698,213 A | 12/1997 | Jamiolkowski et al. | |
| 5,700,583 A | 12/1997 | Jamiolkowski et al. | |
| 5,702,462 A | 12/1997 | Oberlander | |
| 5,711,690 A | 1/1998 | Thrush et al. | |
| 5,711,969 A | 1/1998 | Patel et al. | |
| 5,725,556 A | 3/1998 | Moser et al. | |
| 5,730,933 A | 3/1998 | Peterson | |
| 5,733,337 A | 3/1998 | Carr, Jr. et al. | |
| 5,733,868 A | 3/1998 | Peterson et al. | |
| 5,735,897 A | 4/1998 | Buirge | |
| 5,735,903 A | 4/1998 | Li et al. | |
| 5,736,372 A | 4/1998 | Vacanti et al. | |
| 5,753,267 A | 5/1998 | Badylak et al. | |
| 5,755,791 A | 5/1998 | Whitson et al. | |
| 5,759,190 A | 6/1998 | Vibe-Hansen et al. | |
| 5,759,205 A | 6/1998 | Valentini | |
| 5,762,600 A | 6/1998 | Bruchman et al. | |
| 5,762,966 A | 6/1998 | Knapp et al. | |
| 5,769,899 A | 6/1998 | Schwartz et al. | |
| 5,773,577 A | 6/1998 | Cappello | |
| 5,788,625 A | 8/1998 | Plouhar et al. | |
| 5,795,353 A | 8/1998 | Felt | |
| 5,800,537 A | 9/1998 | Bell | |
| 5,830,708 A | 11/1998 | Naughton | |
| 5,834,232 A | 11/1998 | Bishop et al. | |
| 5,842,477 A | 12/1998 | Naughton et al. | |
| 5,847,012 A | 12/1998 | Shalaby et al. | |
| 5,855,610 A | 1/1999 | Vacanti et al. | |
| 5,855,613 A | 1/1999 | Antanavich et al. | |
| 5,855,619 A | 1/1999 | Caplan et al. | |
| 5,859,150 A | 1/1999 | Jamiolkowski et al. | |
| 5,861,004 A | 1/1999 | Kensey et al. | |
| 5,863,551 A | 1/1999 | Woerly | |
| 5,865,849 A | 2/1999 | Stone | |
| 5,866,414 A | 2/1999 | Badylak et al. | |
| 5,885,619 A | 3/1999 | Patel et al. | |
| 5,891,558 A | 4/1999 | Bell et al. | |
| 5,899,939 A | 5/1999 | Boyce et al. | |
| 5,906,997 A | 5/1999 | Schwartz et al. | |
| 5,916,265 A | 6/1999 | Hu | |
| 5,922,028 A | 7/1999 | Plouhar et al. | |
| 5,939,323 A | 8/1999 | Valentini et al. | |
| 5,954,723 A | 9/1999 | Spetzler | |
| 5,954,747 A | 9/1999 | Clark | |
| 5,955,100 A | 9/1999 | Bosslet et al. | |
| 5,958,874 A | 9/1999 | Clark et al. | |
| 5,968,096 A | 10/1999 | Whitson et al. | |
| 5,971,987 A | 10/1999 | Huxel et al. | |
| 5,980,524 A | 11/1999 | Justin et al. | |
| 5,981,802 A | 11/1999 | Katz | |
| 5,981,825 A | 11/1999 | Brekke | |
| 5,989,269 A | 11/1999 | Vibe-Hansen et al. | |
| 5,989,280 A | 11/1999 | Euteneuer et al. | |
| 5,993,475 A | 11/1999 | Lin et al. | |
| 5,993,844 A | 11/1999 | Abraham et al. | |
| 5,997,575 A | 12/1999 | Whitson et al. | |
| 6,010,525 A | 1/2000 | Bonutti et al. | |
| 6,017,301 A | 1/2000 | Schwartz et al. | |
| 6,017,348 A | 1/2000 | Hart et al. | |
| 6,027,744 A | 2/2000 | Vacvanti et al. | |
| 6,034,140 A | 3/2000 | Schwartz et al. | |
| 6,042,610 A | 3/2000 | Li et al. | |
| 6,051,750 A | 4/2000 | Bell | |
| 6,056,752 A | 5/2000 | Roger | |
| 6,056,777 A | 5/2000 | McDowell | |
| 6,056,778 A | 5/2000 | Grafton et al. | |
| 6,060,640 A | 5/2000 | Pauley et al. | |
| 6,066,160 A | 5/2000 | Colvin et al. | |
| 6,068,648 A | 5/2000 | Cole et al. | |
| 6,077,989 A | 6/2000 | Kandel et al. | |
| 6,080,194 A | 6/2000 | Pachence et al. | |
| 6,093,201 A | 7/2000 | Cooper et al. | |
| 6,098,347 A | 8/2000 | Jaeger et al. | |
| 6,099,567 A | 8/2000 | Badylak et al. | |
| 6,110,212 A | 8/2000 | Gregory | |
| 6,126,686 A | 10/2000 | Badylak et al. | |
| 6,133,325 A | 10/2000 | Schwartz et al. | |
| 6,146,385 A | 11/2000 | Torrie et al. | |
| 6,152,935 A | 11/2000 | Kammerer et al. | |
| 6,153,292 A | 11/2000 | Bell et al. | |
| 6,156,044 A | 12/2000 | Kammerer et al. | |
| 6,165,225 A | 12/2000 | Antanavich et al. | |
| 6,171,344 B1 | 1/2001 | Atala | |
| 6,176,880 B1 | 1/2001 | Plouhar et al. | |
| 6,179,840 B1 | 1/2001 | Bowman | |

| | | |
|---|---|---|
| 6,179,872 B1 | 1/2001 | Bell et al. |
| 6,187,039 B1 | 2/2001 | Hiles et al. |
| 6,197,296 B1 | 3/2001 | Davies et al. |
| 6,206,931 B1 | 3/2001 | Cook et al. |
| 6,214,048 B1 | 4/2001 | Ito et al. |
| 6,214,049 B1 | 4/2001 | Gayer et al. |
| 6,224,892 B1 | 5/2001 | Searle |
| 6,235,057 B1 | 5/2001 | Roger et al. |
| 6,242,247 B1 | 6/2001 | Rieser et al. |
| 6,251,143 B1 * | 6/2001 | Schwartz et al. ......... 623/23.72 |
| 6,251,876 B1 | 6/2001 | Bellini et al. |
| 6,258,124 B1 | 7/2001 | Darois et al. |
| 6,264,702 B1 | 7/2001 | Ory et al. |
| 6,265,333 B1 | 7/2001 | Dzenis et al. |
| 6,267,957 B1 | 7/2001 | Green et al. |
| 6,270,530 B1 | 8/2001 | Eldridge et al. |
| 6,273,893 B1 | 8/2001 | McAllen, III et al. |
| 6,280,473 B1 | 8/2001 | Lemperle et al. |
| 6,280,474 B1 | 8/2001 | Cassidy et al. |
| 6,283,980 B1 | 9/2001 | Vibe-Hansen et al. |
| 6,288,043 B1 | 9/2001 | Spiro et al. |
| 6,290,711 B1 | 9/2001 | Caspari et al. |
| 6,293,961 B2 | 9/2001 | Schwartz et al. |
| 6,294,041 B1 | 9/2001 | Boyce et al. |
| 6,299,905 B1 | 10/2001 | Peterson et al. |
| 6,306,156 B1 | 10/2001 | Clark |
| 6,306,159 B1 | 10/2001 | Schwartz et al. |
| 6,306,177 B1 | 10/2001 | Felt et al. |
| 6,319,258 B1 | 11/2001 | McAllen, III et al. |
| 6,319,271 B1 | 11/2001 | Schwartz et al. |
| 6,326,025 B1 | 12/2001 | Sigler et al. |
| 6,333,029 B1 | 12/2001 | Vyakarnam et al. |
| 6,334,872 B1 | 1/2002 | Termin et al. |
| 6,355,699 B1 | 3/2002 | Vyakarnam et al. |
| 6,358,284 B1 | 3/2002 | Fearnot et al. |
| 6,364,884 B1 | 4/2002 | Bowman et al. |
| 6,371,958 B1 | 4/2002 | Overaker |
| 6,373,221 B1 | 4/2002 | Koike et al. |
| 6,379,367 B1 | 4/2002 | Vibe-Hansen et al. |
| 6,379,710 B1 | 4/2002 | Badylak |
| 6,383,221 B1 | 5/2002 | Scarborough et al. |
| 6,387,693 B2 | 5/2002 | Rieser et al. |
| 6,402,766 B2 | 6/2002 | Bowman et al. |
| 6,409,764 B1 | 6/2002 | White et al. |
| 6,423,073 B2 | 7/2002 | Bowman |
| 6,436,110 B2 | 8/2002 | Bowman et al. |
| 6,440,444 B2 | 8/2002 | Boyce et al. |
| 6,447,517 B1 | 9/2002 | Bowman |
| 6,451,032 B1 | 9/2002 | Ory et al. |
| 6,458,158 B1 | 10/2002 | Anderson et al. |
| 6,458,383 B2 | 10/2002 | Chen et al. |
| 6,464,729 B1 | 10/2002 | Kandel |
| 6,497,650 B1 | 12/2002 | Nicolo |
| 6,497,707 B1 | 12/2002 | Bowman et al. |
| 6,508,821 B1 | 1/2003 | Schwartz et al. |
| 6,517,564 B1 | 2/2003 | Grafton et al. |
| 6,566,345 B2 | 5/2003 | Miller et al. |
| 6,572,650 B1 | 6/2003 | Abraham et al. |
| 6,592,623 B1 | 7/2003 | Bowlin et al. |
| 6,638,312 B2 | 10/2003 | Plouhar et al. |
| 6,652,872 B2 | 11/2003 | Nevo et al. |
| 6,666,892 B2 | 12/2003 | Hiles et al. |
| 6,692,499 B2 | 2/2004 | Törmäläet et al. |
| 6,808,194 B2 | 10/2004 | Martin |
| 6,812,221 B2 | 11/2004 | McKeehan et al. |
| 6,840,962 B1 | 1/2005 | Vacanti et al. |
| 6,869,938 B1 | 3/2005 | Schwartz et al. |
| 6,989,034 B2 | 1/2006 | Hammer et al. |
| 7,819,918 B2 * | 10/2010 | Malaviya et al. ......... 623/14.12 |
| 7,914,808 B2 * | 3/2011 | Malaviya et al. ............ 424/423 |
| 2001/0002446 A1 | 5/2001 | Plouhar et al. |
| 2001/0023373 A1 | 9/2001 | Plouhar et al. |
| 2001/0024658 A1 | 9/2001 | Chen et al. |
| 2001/0043943 A1 | 11/2001 | Coffey |
| 2002/0019649 A1 | 2/2002 | Sikora et al. |
| 2002/0031551 A1 | 3/2002 | Peterson et al. |
| 2002/0034533 A1 | 3/2002 | Peterson et al. |
| 2002/0038151 A1 | 3/2002 | Plouhar et al. |
| 2002/0048595 A1 | 4/2002 | Geistlich et al. |
| 2002/0052628 A1 | 5/2002 | Bowman |
| 2002/0090725 A1 | 7/2002 | Simpson et al. |
| 2002/0091444 A1 | 7/2002 | Yang |
| 2002/0095157 A1 | 7/2002 | Bowman |
| 2002/0099448 A1 | 7/2002 | Hiles et al. |
| 2002/0165611 A1 | 11/2002 | Enzerink et al. |
| 2002/0169465 A1 | 11/2002 | Bowman et al. |
| 2002/0173806 A1 | 11/2002 | Giannetti et al. |
| 2003/0014126 A1 | 1/2003 | Patel et al. |
| 2003/0021827 A1 | 1/2003 | Malaviya et al. |
| 2003/0023316 A1 | 1/2003 | Brown et al. |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0044444 A1 | 3/2003 | Malaviya et al. |
| 2003/0049299 A1 | 3/2003 | Malaviya et al. |
| 2003/0078617 A1 | 4/2003 | Schwartz et al. |
| 2003/0212447 A1 | 11/2003 | Euteneuer et al. |
| 2004/0059431 A1 | 3/2004 | Plouhar et al. |
| 2004/0143344 A1 | 7/2004 | Malaviya et al. |
| 2004/0166169 A1 | 8/2004 | Malaviya et al. |
| 2004/0220574 A1 | 11/2004 | Pelo et al. |
| 2005/0027307 A1 | 2/2005 | Schwartz et al. |
| 2005/0112248 A1 * | 5/2005 | Galloway ...................... 426/237 |
| 2005/0249771 A1 | 11/2005 | Malaviya et al. |
| 2005/0249772 A1 | 11/2005 | Malaviya et al. |

FOREIGN PATENT DOCUMENTS

| | | |
|---|---|---|
| EP | 0591991 A2 | 4/1994 |
| EP | 0832999 A1 | 11/1995 |
| EP | 0 734 736 A1 | 10/1996 |
| EP | 1070487 | 1/2001 |
| EP | 1593400 A1 | 11/2005 |
| GB | 2 215 209 | 9/1989 |
| JP | 11319068 A | 11/1999 |
| WO | WO 90/09769 | 9/1990 |
| WO | WO 94/11008 | 5/1994 |
| WO | WO 95/05083 | 2/1995 |
| WO | WO 95/22301 | 8/1995 |
| WO | WO 95/06439 | 9/1995 |
| WO | 9532623 | 12/1995 |
| WO | WO 95/32623 | 12/1995 |
| WO | 9625961 | 8/1996 |
| WO | W096/24304 | 8/1996 |
| WO | WO 96/24661 | 8/1996 |
| WO | WO 97/05193 | 2/1997 |
| WO | 9730662 | 8/1997 |
| WO | WO 97/37613 | 10/1997 |
| WO | WO 98/06445 | 2/1998 |
| WO | 9822154 | 5/1998 |
| WO | WO 98/22158 A2 | 5/1998 |
| WO | WO 98/22158 A3 | 5/1998 |
| WO | WO 98/30167 | 7/1998 |
| WO | WO 98/34569 | 8/1998 |
| WO | WO 98/40111 | 9/1998 |
| WO | WO 99/03979 | 1/1999 |
| WO | WO 99/43786 | 9/1999 |
| WO | WO 99/47188 | 9/1999 |
| WO | 0015153 | 3/2000 |
| WO | WO 00/15765 | 3/2000 |
| WO | WO 00/16822 | 3/2000 |
| WO | WO 00/24437 A2 | 5/2000 |
| WO | WO 00/24437 A3 | 5/2000 |
| WO | WO 00/32250 | 6/2000 |
| WO | WO 00/48550 | 8/2000 |
| WO | 0072782 | 12/2000 |
| WO | WO 00/72782 | 12/2000 |
| WO | WO 01/19423 | 3/2001 |
| WO | WO 01/39694 A2 | 6/2001 |
| WO | WO 01/39694 A3 | 6/2001 |
| WO | WO 01/45765 | 6/2001 |
| WO | WO 01/66159 | 9/2001 |
| WO | WO 02/22184 | 3/2002 |
| WO | WO 03/007784 | 1/2003 |
| WO | WO 03/007788 A2 | 1/2003 |
| WO | WO 03/007790 A2 | 1/2003 |

OTHER PUBLICATIONS

Hiles et al., "Mechanical properties of xenogeneic small-intestinal submucosa when used as an aortic graft in the dog", *Journal of Biomedical Materials Research*, vol. 29, 883-891, (1995).

Sandusky, et al., "Healing Comparison of Small Intestine Submucosa and ePTFE Grafts in the Canine Carotid Artery", *J. Surg. Res..* 58:415-420. (1995).

Knapp, et al., "Biocompatibility of Small-Intestine Submucosa in Urinary Tract as Augmentation Cystoplasty Graft and Injectable Suspension" *J Endourology*, 8:125-130 (1994).

Kropp et al., "Regenerative Bladder Augmentation: A Review of the Initial Preclinical Studies with Porcine Small Intestinal Submucosa", *Muscle Matrix and Bladder Function*, Plenum Press, New York, (1995).

Kropp et al., "Experimental Assessment of Small Intestinal Submucosa as a Bladder Wall Substitute", *Urology* 446:396-400, (1995).

Vaught et al., "Detrusor Regeneration in the Rat Using Porcine Small Intestinal Submucosa Grafts: Functional Innervation and Receptor Expression", *J. Urol.*, 155:374-378, (1996).

Kropp et al, Characterization of Small Intestinal Submucosa Regenerated Canine Detrusor: Assessment of Reinnervation, In Vitro Compliance and contractility, *J. of Urol.* 156.599-607. (1996).

Kropp et al., "Regenerative Urinary Bladder Augmentation Using Small Intestinal Submucosa: Urodynamic and Histopathologic Assessment in Long-Term Canine Bladder Auamentations" *Journal of Urology*. 155:2098-2104 (1996).

Aiken et al., " Small Intestinal Submucosa as an Intra-Articular Ligamentous Graft Material: A Pilot Study in Dogs". *Vet Comp Orthopedics Traumatology*. 7:124-128. (1994).

Badylak et al., "The Use of Xenogeneic Small Intestinal Submucosa as a Biomaterial for Achille's Tendon Repair in a dog model" *J Biomed Materials*, 29:977-985, (1995).

Hodde et al., "The Effect of Range of Motion Upon Remodeling of Small Intestinal Submucosa (SIS) when used as an Achilles Tendon Repair Material in the Rabbit", Tissue Engineering 3, 1:27-37, (1997).

Ferrand et al., "Directional Porosity of Porcine Small-Intestinal Submucosa", *J Biomed Materials Res*, 27:1235-1241, (1993).

Hiles et at., "Porosity of Porcine Small-Intestinal Submucosa for use as a Vascular Graft", *J Biomed Materials Res*, 27: 139-144 (1993).

Hodde et al., "Glycosaminoglycan Content of Small Intestinal Submucosa: A Bioscaffold for Tissue Replacement", *Tissue Engineering*, 2:3, 209-217, (1996).

Prevel et al., "Small Intestinal Submucosa: Utilization for Repair of Rodent Abdominal Wall Defects", *Ann Plast Surg*, 35:374-380, (1995).

Clarke et al., "Intestine Submucosa and Polypropylene Mesh for Abdominal Wall Repair in Dogs", *J Surg Res*, 60:107-114, (1996).

Prevel et al., "Small Intestinal Submucosa: Utilization as a Wound Dressing in Full-Thickness Rodent Wounds", *Ann Plast Surg*, 35:381-388. (1995).

Cobb et al., "Histology after Dural Grafting with Small Intestinal Submucosa", *Surgical Neurology*, 46: 389-394, (1996).

Cobb et al., "Porcine Small Intestinal Submucosa as a Dural Substitute", *Surgical Neurology*, 51:99-104, (1999).

Voytik-Harbin et al., "Application and Evaluation of the AlamarBlue Assay for Cell Growth and Survival of Fibroblasts", *Journal of Immunological Methods, In Vitro Cell Bio-Animal*. 34: 2399-246 (1998).

Suckow, M.A., "Enhanced Bone Regeneration Using Porcine Small Intestinal Submucosa", *J. Invest Surg*, 12: 277, (1999).

Badylak , S., et al., "Naturally Occurring Extracellular Matrix as a Scaffold for Musculoskeletal Repair", *Clin Orthop*, 3675:S333-S3433, (1999).

Cook, J.L. et al., "Induction of Meniscal Regeneration in Dogs Using a Novel Biomaterial", *Am J Sports Med*, 27: 658, (1999).

Dejardin, L.M. et al., "Use of small intestinal submucosal implants for regeneration of large fascial defects: an experimental study in dogs", J Biomed Mater Res, 46:203-211, (1999).

Sacks, M.S., et al., "Quantification of the fiber architecture and biaxial mechanical behavior of porcine intestinal submucosa", *J Biomed Mater Res*, 46:1-10, (1999).

Cook® News Releases, "Cook® Introduces Innovative™ Surgisism Soft Tissue Repair Biomaterial", (May 21, 2000).

Cook® News Releases, "Cook® Oasis™ Wound Dressing Biomaterial From Cook® Remodels Partial Thickness Skin Injuries", (Dec. 23, 1999).

Cook® News Releases, "Cook Incorporated Forms Dedicated Tissue Engineered Products Group", (Feb. 16, 2000).

Cook® News Releases, "FDA Clears Oasis™ Wound Dressing Biomaterial From Cook® for Full-Thickness Skin Injuries", (Jan. 24, 2000).

Klootwyk, et al., "The Use of Xenographic SIS as a Biomaterial for Achilles Tendon Repair in Dogs," First SIS Symposium, Dec. 1996, USA.

Lenz, et al., "SIS as an ACL Replacement in Dogs and Goats," First Symposium, Dec. 1996, USA.

Cook, et al., "Comparison of SIS Cancellous Bone as Substrates for Three-Dimensional Culture of Canine Articular Chondrocytes," First SIS Symposium, Dec. 1996, USA.

Badylak, et al., "Different Configurations of Small Intestinal Submucosa as a Biomaterial for Achilles Tendon Repair in a Dog Model," First SIS Symposium, Dec. 1996, USA.

Voytik-Harbin & Badylak, "Induction of Osteogenic Activity by Small Intestinal Submucosa in Rat Calvaria Non-union Defects," First SIS Symposium, Dec. 1996, USA.

Kandel, et al., "SIS and Reconstituted Cartilage and Its Use in Joint Resurfacing of Focal Defects in Rabbits," First SIS Symposium, Dec. 1996, USA.

Tullius, et al., "Differential Permeabilty of SIS," First SIS Symposium, Dec. 1996, USA.

Obermiller, et al., "Suture Retention Strength of SIS," First SIS Symposium, Dec. 1996, USA.

Shelton, et al., "Repair of the Canine Medial Meniscus using SIS: A Feasibility Study," Second SIS Symposium, Dec. 1998, USA.

Cook, et al., "Meniscal Regeneration in dogs Using Grafts of SIS," Second SIS Symposium, Dec. 1998, USA.

Welch, et al., "Healing of Canine Meniscal Defect with Small Intestinal Submucosa Implants," Dec. 1998, USA.

Solchaga, et al., "SIS as Delivery Vehicle for Mesenchymal Progenitor Cells," Dec. 1998, USA.

Paulino, et al., "The Use of an SIS-PGA Composite Graft for Repair of Cartilage Defect," Dec. 1998, USA.

Toombs and May, "Clinical Follow-Up of Three Canine ACL Reconstructions Using an SIS ACL Device," Dec. 1998, USA.

Tomasek and Gifford, "Small Intestinal Submucosa Matrix Regulates the Differentiation of Myofibroblasts," Third SIS Symposium, Nov. 2000, USA.

Cook, et al., Tissue Engineering for Meniscal Repair Using SIS: Third SIS Symposium, Nov. 2000, USA.

Lifrak, et al., "Enhanced Repair of Goat Meniscal Defects Using Porcine Small Intestinal Submucosa (SIS)," Third SIS Symposium, Nov. 2000, USA.

Hoffman, "SIS Disc Replacement for the Temporomandibular Joint," Third SIS Symposium, Nov. 2000, USA.

Kaeding, "Use of SIS in the Surgical Treatment of Chronic Symptomatic Patella Tendinosis," Third SIS Symposium, Nov. 2000, USA.

Tomczak and Kaeding, "Use of SIS in the Surgical Treatment of Tendinosis About the Foot and Ankle," Third SIS Symposium, Nov. 2000, USA.

Moore, et al., "Bridging Segmental Defects in Long Bones With Intramedullary Tubes and Periosteal Sleeves Made From Small Intestinal Submucosa (SIS)," Third SIS Symposium, Nov. 2000, USA.

Wang, et al., "Small Intestinal Submucosa Enhances Healing of Medical Collateral Ligament in a Rabbit Model," Third SIS Symposium, Nov. 2000, USA.

Ojha, et al., "PGA-Plla Versus Small Intestinal Submucosa (SIS): A Comparison of Neo-Cartilage Grown From Two Scaffold Materials," Third SIS Symposium, Nov. 2000, USA.

Wiklerson, "Use of the Porcine Small Intestine Submucosal Tissue Graft and Repair of Rotator Cuff Tears," Third SIS Symposium, Nov. 2000, USA.

"Small Intestinal Submucosa," Third SIS Symposium, Nov. 2000, USA.
"Current Clinical Applications of SIS," Third SIS Symposium, Nov. 2000, USA.
Hodde, et al., "Glycosaminoglycan Content of Small Intestinal Submucosa: A Potential for GAG-Growth Interactions in SIS-Mediated Healing", First Symposium, Dec. 1996, USA.
Zhang et al., Design of nanostructured biological materials through self-assembly of peptides and proteins, MIT Current Opinion in chemical Biology, 2002, 6:865-871.
Hodde and Hiles, "Bioactive FGF-2 in sterilized extracellular matrix", Wounds, 13(5): 195-201 (2001).
O'Meara, Patrick, "The basic science of meniscus repair," Orthopaedic review, Jun. 1993, pp. 681-686.
Clearfix screw advertisement, 1998, Innovasive devices, Inc.
Winters and Justin, "Clearfix meniscal screw", Innovasive devices, Inc. 1998.
Surgical dynamics, meniscal stapler advertisement, 1997.
Bionix implants, Meniscus arrow advertisement, 1996.
Instrument maker, inc., Meniscus mender II, 1989.
Friess, "Collagen in drug delivery and tissue engineering", *Advanced Drug Delivery Reviews*, vol. 55, No. 12, 2003, pp. 1529-1530.
Olsen et al., "Recombinant collagen and gelatin for drug delivery", *Advanced Drug Delivery Reviews*, vol. 55, No. 12, 2003, pp. 1547-1567.
Aigner et al., "Collagens-major component of the physiological cartilage matrix, major target of cartilage degeneration, major tool in cartilage repair", *Advanced Drug Delivery Reviews*, vol. 55, No. 12, 2003, pp. 1569-1593.
Geiger et al., "Collagen sponges for bone regeneration with rhBMP-2", *Advanced Drug Delivery Reviews*, vol. 55, No. 12, 2003, pp. 1613-1629.
Ruszczak et al., "Collagen as a carrier for on-site delivery of antibacterial drugs", *Advanced Drug Delivery Reviews*, vol. 55, No. 12, 2003, pp. 1679-1698.
O'Grady et al., "Global regulatory registration requirements for collagen-based combination products: points to consider," *Advanced Drug Delivery Reviews*, vol. 55, No. 12, 2003, pp. 1699-1721.
Matthews et al., "Electrospinning of Collagen Type II: A Feasibility Study", *Journal of Bioactive and Compatible Polymers*, vol. 18, Mar. 2003, pp. 125-134.
Biscarini et al., "Growth of High Vacuum Sublimed Oligomer Thin Films", *ACS Polymer Preprints*, vol. 37, No. 2, 1996, pp. 618-619.
Biscarini et al., "Morphology and roughness of high-vacuum sublimed oligomer thin films", *Thin Solid Films*, vol. 439-443, 1996, pp. 284-285.
Biscarini et al., "Scaling Behavior of Anisotropic Organic Thin Films Grown in High-Vacuum", *Physical Review Letters*, vol. 78, No. 12, Mar. 24, 1997, pp. 2389-2392.
Voytik-Harbin et al., "Identification of Extractable Growth Factors from Small Intestinal Submucosa", *Journal of Cellular Biochemistry*, vol. 67, 1997, pp. 478-491.
McPherson, Ph.D. et al., "Characterization of Fibronectin Derived from Porcine Small Intestinal Submucosa", *Tissue Engineering*, vol. 4, No. 1, 1998, pp. 75-83.
Hodde, et al., "Vascular Endothelial Growth Factor in Porcine-Derived Extracellular Matrix", *Endothelium*, vol. 8(1), 2001, pp. 11-24.
Hodde et al., "Wounds: A Compendium of Clinical Research and Practice", Website: http:www.hmpcommunications.com/WNDS, Printed: Jul. 12, 2005, 7 pgs.
Hurst et al., "Mapping of the distribution of significant proteins and proteoglycans in small intestinal submucosa by fluorescence microscopy", *J. Biomater. Sci. Polymer Edn.*, vol. 12, No. 11, 2001, pp. 1267-1279.
Hodde et al., "Fibronectin peptides mediate HMEC adhesion to porcine-derived extracellular matrix", *Biomaterials*, vol. 23, 2002, pp. 1841-1848.
Hodde, "Naturally Occurring Scaffolds for Soft Tissue Repair and Regeneration", *Tissue Engineering*, vol. 8, No. 2, 2002, pp. 295-308.
Allman et al., Xenogeneic Extracellular Matrix Grafts Elicit a Th2-Restricted Immune Response, *Transplantation*, vol. 71, No. 11, Jun. 15, 2001, pp. 1631-1640.

Allman et al., "The Th2-Restricted Immune Response to Xenogeneic Small Intestinal Submucosa Does Not Influence Systemic Protective Immunity to Viral and Bacterial Pathogens", *Tissue Engineering*, vol. 8, No. 1, 2002, pp. 53-62.
Krčma, "Nonwoven Textiles", *Textile Trade Press*, Manchester, England, 1962, 6 pgs.
Answers.com,. Definition of "freeze-dry", Accessed on May 12, 2005, 6 pgs.
Ma et al., "Microtubular architecture of biodegradable polymer scaffolds", *J. Biomed. Materials Res.*, vol. 56, No. 4, 2001, pp. 469-477.
Ma et al., "Biodegradable Polymer Scaffolds with Well-Defined Interconnected Spherical Pore Network", *Tissue Engineering*, vol. 7, No. 1, 2001, pp. 23-33.
Klawitter et al., "An Evaluation of Bone Growth into Porous High Density Polyethylene", *J. Biomed. Materials Res.*, vol. 10, (1976) pp. 311-323.
White et al., "Biomaterial Aspects of Interpore-200 Porous Hydroxyapatite", *Dental Clinics of North America*, Reconstructive Implant Surgery and Implant Prosthodontics 1, vol. 30, No. 1, pp. 49-67.
Shors, Coralline Bone Graft Substitutes, *Orthopaedic Clinics of North America*, Bone Grafting and Bone Graft Substitutes, vol. 30, No. 4, Oct. 1999, pp. 599-613.
Wang, Experimental Study of Osteogenic Activity of Sintered Hydroxyapatite—On the Relationship of Temperature and Pore Size-, *J. Jpn. Orthop. Assoc.*, vol. 64, 1990, pp. 847-859.
Nehrer et al., "Matrix collagen type and pore size influence behavior of seeded canine chondrocytes", *Biomaterials*, vol. 18, No. 11, 1997, pp. 769-776.
Salem et al., "Interactions of 3T3 fibroblasts and endothelial with defined pore ffeatures", *J. Biomed Materials Res.*, vol. 61, No. 2, 2002, pp. 212-217.
Definitions of "intertwine" and "twine", *American Heritage Dictionary of the English Language Online*, Accessed Sep. 29, 2005, 2 pgs.
How to Cut Meat Products 2001, *Urschel Corp.*, Accessed online at fr.urschel.com/literature/HTCMeat.pdf on Oct. 3, 2005, 8 pgs.
Definitions of "comminute" and "slurry", *Dictionary.com*; Accessed Sep. 20, 2005, 2 pgs.
William G. Clancy, Jr., M.D., and Ben K. Graf, M.D., "Arthroscopic Meniscal Repair," ACUFEX Microsurigal Inc., advertisement, 1988.
P. K. Chu et al., "Plasma-surface modification of biomaterials", Materials Science and Engineering, Reports: A Review Journal, vol. 36, No. 5-6, Mar. 29, 2002, pp. 143-208.
Amoczky et al., The microvasculature of the meniscus and its response to Injury—An experimental study in the dog, *Am. J. Sports Med.*, 1983, 11(3); pp. 131-141.
Fox at al., Trephination of incomplete meniscal tears, *Arthroscopy*, 1993, 9(4); pp. 451-455.
Arnoczky et al., Meniscal repair using an exogenous fibrin clot—An experimental study of dogs, *J. Bone Joint Surg. Am.*, 1988, 70(8), pp. 1209-1216.
Rodeo, "Arthroscopic meniscal repair with use of the outside-in technique", *Instr. Course Lect.*, 2000, 49, pp. 195-206.
Stollsteimer et al., "Meniscal allograft transplantation: a 1- to 5-year follow-up of 22 patients", *Arhroscopy*, 2000,16(4), pp. 343-347.
Rodeo, "Meniscal allografts—where do we stand?", *Am. J. Sports Med.*, 2001, 29(2), pp. 246-261.
Sweigart et al., "Toward tissue engineering of the knee meniscus", *Tissue Eng.*, 2001, 7(2), pp. 111-129.
Boss at al., "Technical innovative: creation of a peripheral vascularized trough to enhance healing in cryopreserved meniscal allograft reconstruction", *Knee Surg Sports Traumatol Arthrosc.*, 2000, 8(3), pp. 159-162.
Siegel et al., "Meniscal allografts", *Clin Sports Med.*, 1993, 12(1), pp. 59-80.
Klompmaker et al, "Meniscal replacement using a porous polymer prosthesis: a preliminary study in the dog.", *Biomaterials*, 1996, 17(12), pp. 1169-1175.
de Groot et al., "Use of porous polyurethanes for meniscal reconstruction and meniscal protheses", *Biomaterials*, 1996, 17(2), pp. 163-173.

Spaans et al., "Solvent-free fabrication of micro-porous polyurethane amide and polyurethane-urea scaffolds for repair and replacement of the knee-joint meniscus", *Biomaterials*, 2000, 21(23), pp. 2453-2460.

Stone et al., "Regeneration of meniscal cartilage with use of a collagen scaffold—Analysis of Preliminary data", *J. Bone Joint Surg. Am.*, 1997, 79(12), pp. 1770-1777.

Rodkey at al., "A clinical study of collagen meniscus implants to restore the injured meniscus", *Clin. Orthop.*, 1999, 49(367 Suppl.), pp. S281-S292.

Merriam-Webster Online Dictionary definitions of "suspension", "suspend", "cohesive", "cohesion", "comminute", "pulverize", "submucosa", and "tissue". Accessed Mar. 30, 2006, 9 pgs.

Resin Technology Group, LLC, "Viscosity chart", http://www.resintechgroup.com/tables/viscosity.html, accessed online Mar. 30, 2006, 1 pg.

Definitions from Onelook.com for "trimethylen" and "trimethylene".

J.S. Pieper et at "Preparation and characterization of porous crosslinked collagenous matrices containing bloavailable chondroitin suplhate" Biomaterials 1999, 20: 847-858.

P.B. van Wachem et al. "In vivo biocompatability of carbodiimide-crosslinked collagen matrices: Effects of crosslink density, heparin immobilization, and bFGF loading" J. Biomed. Mater. Res. 2001, 55 (3): 368-378.

Kyumin Whang "A biodegradable polymer scaffold for delivery of osteotropic factors" Biomaterials 2000, 21 (24): 2545-2551.

J.S. Pieper et al. Attachment of glycosaminoglycans to collangenous matrices modulates the tissue response in rats, Biomaterials 2000, 21 (16): 1689-1699.

Kristen Billiar et al. "Effects of carbodiimide crosslinking conditions on the physical properties of laminated intestinal submucosa", J. Biomed. Mater. Res. 2001, 51(1): 101-108.

Toshimitsu Momose et al. "Surface modification of extrasynovial tendon by chemically modified hyaluronic acid coating" J. Biomed. Mater. Res. 2002, 59: 219-224.

Handbook of Biodegradable Polymers Hardwood Press 1997 (251-272).

Cohn et al., "Biodegradable PEO/PLA block copolymers," Journal of Biomedical Materials Research, 1988, 22 (993-1009).

"Polymer Preprints" (ACS Division of Polymer Chemistry), 1989. 30 (1): 498.

The Encyclopedia of Polymer Science, 1988 (13) 31-41.

"Handbook of Biodegradable Polymers" Hardwood Press 1977 (161-182).

"Handbook of Biodegradable Polymers" Hardwood Press 1997 (99-118).

Disilvestro et al., "Effects of Cross-Linking on the Mechanical Properties of a Porous Foam Scaffold of Small Intestine Submucosa", Society for Biomaterials 29th Annual Meeting Transactions, 2003, pp. 88. 2.

Ide et at., "Collagen Hybridization with Poly(I-Lactic Acid) Braid Promotes Ligament Cell Migration", Mater. Sci. Eng. C, 17(1-2), 95-99 (2001).

Bercovy et al., "Carbon-PGLA Prosthesis for Ligament Reconstruction Experimental Basis and Short Term Results in Man", Clin. Orthop. Relat. Res., (196), 159-68 (1985).

Zhu et al, "Immobilization of Biomacromolecules onto Aminolyzed Poly(L-lactic acid) toward Acceleration of Endothelium Regeneration", Tissue Engineering, v 10, pp. 53-61, 2004.

Cheng & Teoh, "Surface modification of ultra thin poly (ÿ caprolactone) films using acrylic acid and collagen", Biomaterials, v25(11), pp. 1991-2001, 2004.

Wan et al., "Cell adhesion on gaseous plasma modified poly-(L-lactide) surface under shear stress field", Biomaterials, v24(21), pp: 3757-3764, 2003.

Yang et al., "Effect of surface treatment on the biocompatibility of microbial polyhydroxyallcanoates", Biomaterials, v 23 (5), pp. 1391-1397, 2002.

Croll et al., "Controllable surface modification of Poly(lactic-co-glycolic acid) (PLGA) by hydrolysis or aminolysis I: physical, chemical, and theoretical aspects", Biomacromolecules, Mar.-Apr. 2004, 5(2): 463-473.

Kwon et al., "Fibroblast culture on surface-modified poly (glycolide-co-ÿ-caprolactone) scaffold for soft tissue regeneration", J. Biomater Sci Polym ed. 2001, 12(10) 1147-60.

Gastel JA, Muirhead WR, Lifrak JT, Fadale PD, Hulstyn MJ, Labrador DP "Meniscal tissue regeneration using a collagenous biomaterial derived from porcine small intestine submucosa", Arthroscopy, Feb; 17(2): 151-159.

Tan W, Krishnaraj R, Desai TA "Evaluation of nanostructured composite collagen-chitosan matrices for tissue engineering", Tissue Eng Apr; 7(2): 203-210, 2001.

Arnoczky SP "Building a meniscus", Biological considerations, Clin Orthop Oct; 367 (suppl), S244-53, 1999.

Metcalf et al., "Surgical technique for xenograft (SIS) augmentation of rotator-cuff repairs", Op Tech Orthop, 12(3): 204-208, 2002.

Courtney et al., "Modification of polymer surfaces: optimization of approaches", Perfusion, v 18 (11), pp. 33-39, 2003.

Supplementary European Search Report, Appln No. 02753403.1 (PCT/US 223190) dated Dec. 21, 2006 (3 pages).

Definitions of "intertwine" and "twine." American Heritage Dictionary of the English Language Online. Accessed Sep. 29, 2005. 2 pages.

European Search Report for European Application No. 02752290.3-1219, Mar. 26, 2007, 5 pages.

\* cited by examiner

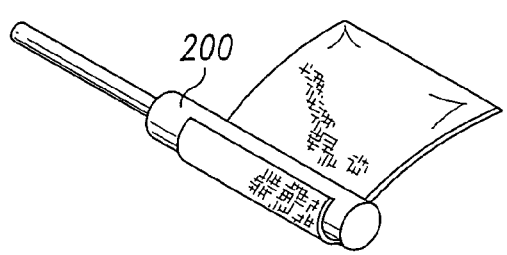
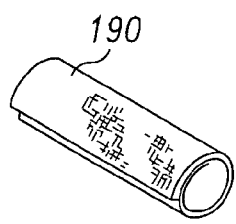
Fig. 20    Fig. 21
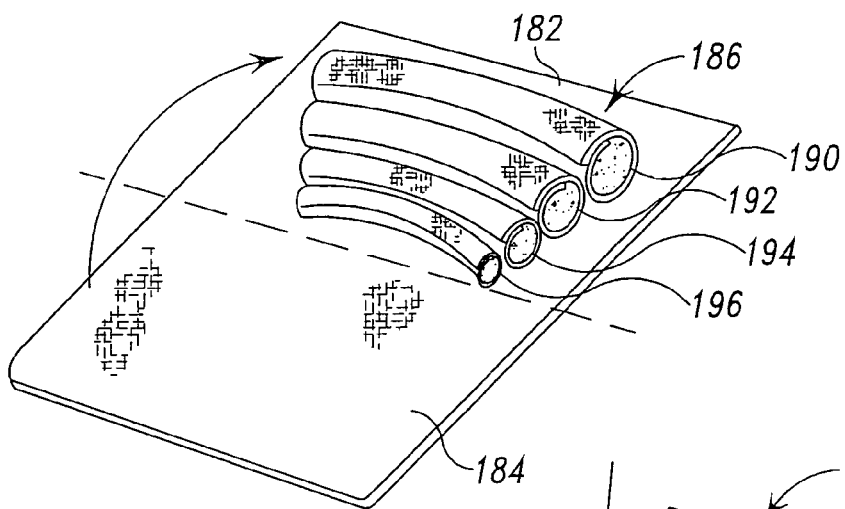
Fig. 22
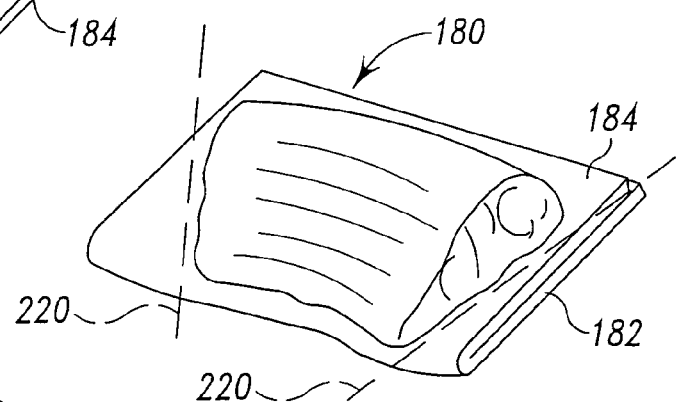
Fig. 23
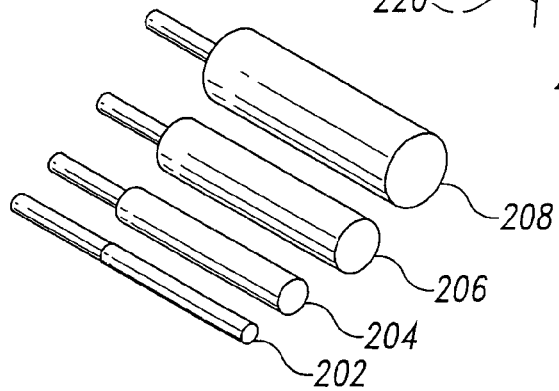
Fig. 20A

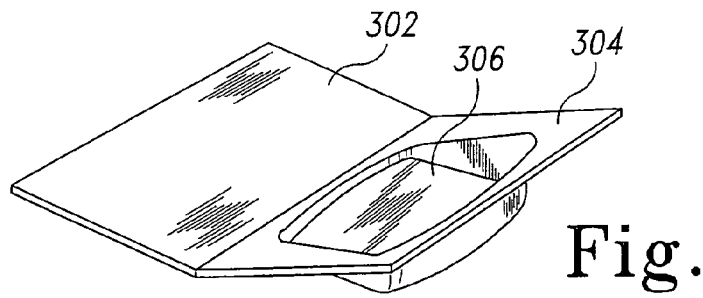
Fig. 36
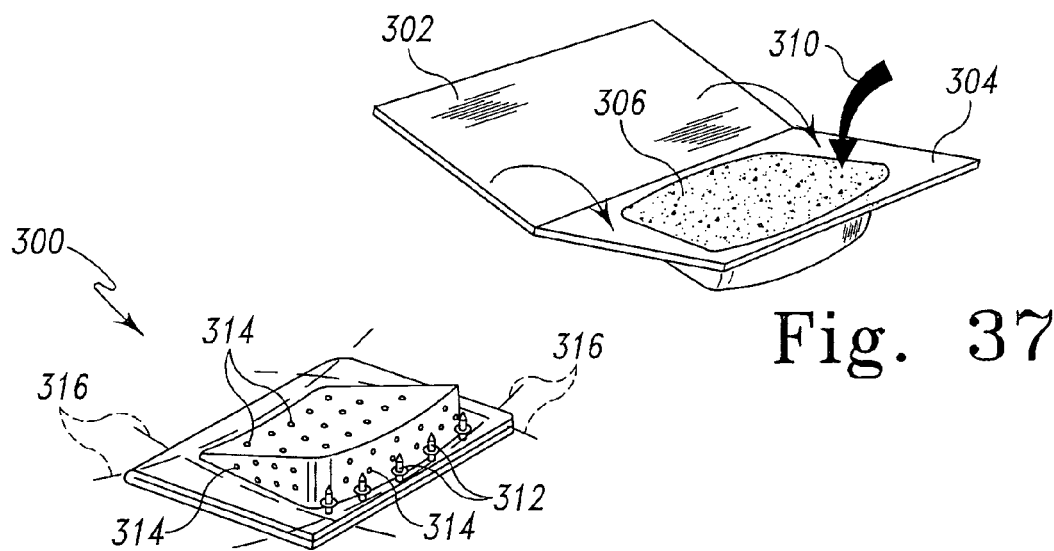
Fig. 37
Fig. 38
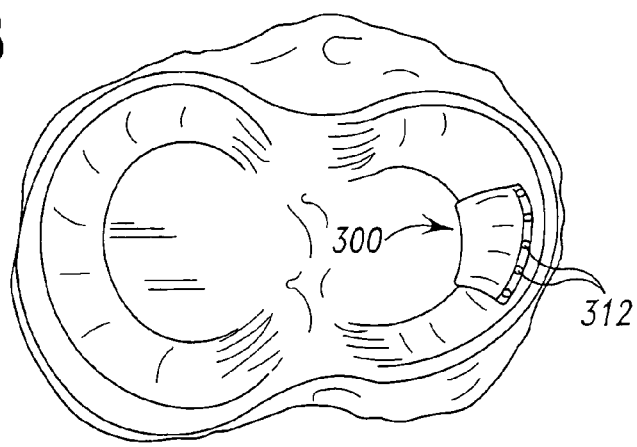
Fig. 39

MENISCUS REGENERATION DEVICE

CROSS REFERENCE

This application claims the benefit of U.S. Provisional Application Nos. 60/388,713, filed Jun. 14, 2002, and 60/305,786, filed on Jul. 16, 2001, which are incorporated by reference herein in there entirety.

Cross reference is made to U.S. patent application Ser. No. 10/195,719 entitled "Devices from Naturally Occurring Biologically Derived Materials"; Ser. No. 10/195,347 entitled "Cartilage Repair Apparatus and Method"; Ser. No. 10/195,344 entitled "Unitary Surgical Device and Method"; Ser. No. 10/195,341 entitled "Hybrid Biologic/Synthetic Porous Extracellular Matrix Scaffolds"; Ser. No. 10/195,606 entitled "Cartilage Repair and Regeneration Device and Method"; Ser. No. 10/195,354 entitled "Porous Extracellular Matrix Scaffold and Method"; Ser. No. 10/195,334 entitled "Cartilage Repair and Regeneration Scaffolds and Method"; and Ser. No. 10/195,633 entitled "Porous Delivery Scaffold and Method", each of which is assigned to the same assignee as the present application, each of which is filed concurrently herewith, and each of which is hereby incorporated by reference. Cross reference is also made to U.S. patent application Ser. No. 10/172,347 entitled "Hybrid Biologic-Synthetic Bioabsorbable Scaffolds" which was filed on Jun. 14, 2002, which is assigned to the same assignee as the present application, and which is hereby incorporated by reference.

BACKGROUND AND SUMMARY OF THE INVENTION

The present disclosure relates to devices for repairing or regenerating a meniscus or a portion of a meniscus in a knee.

It is known to use various collageneous scaffolds to provide a matrix for repair and regeneration of damaged tissue. U.S. Pat. No. 6,042,610 to ReGen Biologics, hereby incorporated by reference, discloses the use of a device comprising a bioabsorbable material made at least in part from purified natural fibers of collagen or glycosaminoglycans. The purified natural fibers are cross-linked to form the device of U.S. Pat. No. 6,042,610. The device can be used to provide augmentation for a damaged meniscus. Related U.S. Pat. Nos. 5,735,903, 5,681,353, 5,306,311, 5,007,934, and 4,880,429 also disclose a meniscal augmentation device for establishing a scaffold adapted for ingrowth of meniscal fibrochondrocyts.

It is also known to use naturally occurring extracellular matrices (ECMs) to provide a scaffold for tissue repair and regeneration. One such ECM is small intestine submucosa (SIS). SIS has been described as a natural biomaterial used to repair, support, and stabilize a wide variety of anatomical defects and traumatic injuries. See, for example, Cook® Online New Release provided by Cook Biotech of Bloomington, Ind., a copy of which can be found at their online website. The SIS material is reported to be a naturally-occurring collagenous matrix derived from porcine small intestinal submucosa that models the qualities of its host when implanted in human soft tissues. Further, it is taught that the SIS material provides a natural matrix with a three-dimensional structure and biochemical composition that attracts host cells and supports tissue remodeling. SIS products, such as Oasis material and Surgisis material, are commercially available from Cook Biotech, Bloomington, IN.

An SIS product referred to as RESTORE Orthobiologic Implant is available from DePuy Orthopaedics, Inc. in Warsaw, Ind. The DePuy product is described for use during rotator cuff surgery, and is provided as a resorbable framework that allows the rotator cuff tendon to regenerate itself. The RESTORE Implant is derived from porcine small intestine submucosa that has been cleaned, disinfected, and sterilized. Small intestine submucosa (SIS) has been described as a naturally-occurring ECM composed primarily of collagenous proteins. Other biological molecules, such as growth factors, glycosaminoglycans, etc., have also been identified in SIS. See Hodde et al., Tissue Eng. 2(3): 209-217 (1996); Voytik-Harbin et al., J. Cell Biochem., 67:478-491 (1997); McPherson and Badylak, Tissue Eng., 4(1): 75-83 (1998); Hodde et al., Endothelium, 8(1):11-24 (2001); Hodde and Hiles, Wounds, 13(5): 195-201 (2001); Hurst and Bonner, J. Biomater. Sci. Polym. Ed., 12(11) 1267-1279 (2001); Hodde et al., Biomaterial, 23(8): 1841-1848 (2002); and Hodde, Tissue Eng., 8(2): 295-308 (2002), all of which are incorporated by reference herein. During seven years of preclinical testing in animals, there were no incidences of infection transmission from the implant to the host, and the SIS material has not decreased the systemic activity of the immune system. See Allman et al., Transplant, 17(11): 1631-1640 (2001); Allman et al., Tissue Eng., 8(1): 53-62 (2002).

Other products made from porcine small intestine are commercially available. For example, Organogenesis, Inc., of Canton, Mass., is understood to market such products under the designations GRAFTPATCH, FORTAFLEX, FORTAGEN and FORTAPERM, and possibly under other designations.

While small intestine submucosa is available, other sources of submucosa are known to be effective for tissue remodeling. These sources include, but are not limited to, stomach, bladder, alimentary, respiratory, or genital submucosa, or liver basement membrane. See, e.g., U.S. Pat. Nos. 6,171,344, 6,099,567, and 5,554,389, hereby incorporated by reference. Further, while SIS is most often porcine derived, it is known that these various submucosa materials may be derived from non-porcine sources, including bovine and ovine sources. Additionally, other collageneous matrices are known, for example lamina propria and stratum compactum.

For the purposes of this disclosure, it is within the definition of a naturally occurring ECM to clean, delaminate, and/or comminute the ECM, or even to cross-link the collagen fibers within the ECM. It is also within the definition of naturally occurring ECM to fully or partially remove one or more sub-components of the naturally occurring ECM. However, it is not within the definition of a naturally occurring ECM to extract and purify the natural collagen or other components or sub-components of the ECM and reform a matrix material from the purified natural collagen or other components or sub-components of the ECM. Thus, while reference is made to SIS, it is understood that other naturally occurring ECMs are within the scope of this invention. Thus, in this application, the terms "naturally occurring extracellular matrix" or "naturally occurring ECM" are intended to refer to extracellular matrix material that has been cleaned, disinfected, sterilized, and optionally cross-linked. The terms "naturally occurring extracellular matrix" and "naturally occurring ECM" are also intended to include ECM foam material prepared as described in copending U.S. patent application Ser. No. 10/195,354 entitled "Porous Extracellular Matrix Scaffold and Method", filed concurrently herewith.

The following patents, hereby incorporated by reference, disclose the use of ECMs for the regeneration and repair of various tissues: U.S. Pat. Nos. 6,334,872, 6,187,039, 6,176,880, 6,126,686, 6,099,567, 6,096,347, 5,997,575, 5,993,844, 5,968,096, 5,955,110, 5,922,028, 5,885,619, 5,788,625, 5,762,966, 5,755,791, 5,753,267, 5,733,337, 5,711,969, 5,645,860, 5,641,518, 5,554,389, 5,516,533, 5,460,962, 5,445,833, 5,372,821, 5,352,463, 5,281,422, and 5,275,826. U.S. Pat. Nos. 5,275,826 and 5,516,533 disclose providing a mass of SIS, particularly as a fluidized injectable mass, to promote repair of tissue defects. U.S. Pat. No. 5,352,463 discloses an SIS pillow filled with comminuted SIS for regeneration of a meniscus. While U.S. Pat. No. 5,352,463 contemplates the general concept of meniscus regeneration with an SIS filled pouch, it does not address itself to providing such a pouch having the capability of withstanding the compression and shear stresses involved in an implant for regenerating a meniscus.

The present disclosure relates to a device for regenerating a meniscus of a knee or a portion thereof. A natural meniscus in a human knee has a generally wedge-shaped cross-section, i.e., a section through a plane extending along and radially outwardly from the axis of the tibia either through the medial meniscus or the lateral meniscus will define a generally wedged-shaped cross-section. Typically, the device will be placed in a meniscal space from which a defective portion of the meniscus is removed, and that space will be a generally wedge-shaped space. The device will be placed in the space and anchored to the surrounding tissue. In one embodiment, a composite device will be inserted into the space from which the defective meniscus portion has been removed. The device comprises an upper cover made from toughened naturally occurring extracellular matrix (ECM), the cover defining a space therebelow. In some embodiments, the cover comprises a plurality of layers of naturally occurring ECM laminated together and toughened to withstand articulation stresses. A mass comprising comminuted naturally occurring ECM is disposed in the space. In various embodiments, the mass may also comprise bioactive agents, biologically-derived agents, cells, biological lubricants, biocompatible inorganic materials, biocompatible polymers and/or some combination thereof mixed with the comminuted ECM.

In some embodiments, a biocompatible polymer can be used in conjunction with naturally occurring ECM. See, for example, the teachings of U.S. patent application Ser. No. 10/195,341 entitled "Hybrid Biologic/Synthetic Porous Extracellular Matrix Scaffolds" filed contemporaneously herewith, and U.S. patent application Ser. No. 10/172,347 entitled "Hybrid Biologic-Synthetic Bioabsorbable Scaffolds," which was filed on Jun. 14, 2002.

An implant for regeneration or repair of the meniscus of the knee may be toughened to withstand better the compression and/or shear forces of the knee for a sufficient amount of time for remodeling to begin. It will be understood that a surgeon may immobilize or partially immobilize the knee for a period of time subsequent to surgery. The rehabilitation protocol may include limited articulation, compression, and shear forces for a period of time. However, an implant that is toughened should be able to withstand even these reduced forces better than an equivalent implant that has not been toughened. At the same time, the material must be porous enough to permit remodeling. Thus, it is preferred that the condyle-facing surface of the ECM device of this disclosure is toughened to withstand the forces. Toughness may include stiffness (i.e. tensile modulus), resistance to delamination, increased thickness, resistance to shear or abrasion, decreased water content, or increased density, for example.

One method of toughening is dehydrothermal cross-linking. Techniques for dehydrothermal cross-linking are known in the art, but the steps in one method include applying mechanical pressure to the ECM while using vacuum to remove water, and subsequently delivering pressurized warm air to the ECM, thus producing a dehydrated ECM. Other methods of mechanical cross-linking, as are known in the art, may be used to toughen the upper cover of the device of the present disclosure. Such methods of physical cross-linking include, for example, freeze-drying, irradiation (ultraviolet or gamma irradiation) and combinations of methods. In addition, chemical cross-linking can be used to toughen the upper cover of the device of the present disclosure. Chemical cross-linking can be achieved through the use of materials like aldehydes, carbodiimides, glycation agents, enzymes and the like.

In some embodiments, the upper cover is formed by laminating a plurality of sheets of naturally occurring ECM and treating it to provide a toughened surface capable of withstanding the compression and shear stresses involved in knee articulation, i.e., the articulation of the knee condyle on the device inserted into the meniscus. The mass in the space below the upper cover may be comminuted SIS or is alternatively bioactive agents, biologically derived agents, cells or combinations thereof, for example. Other collageneous materials may also be used for the mass in the space below the upper cover, alone or in combination with the above-mentioned materials. The mass of comminuted naturally occurring ECM is believed to provide a framework for meniscus regeneration. The insertion of the device into the space from which the defective portion has been removed and the attachment of the device to the surrounding tissue places the device such that it is in contact with the host tissue of the remaining meniscus such that the meniscus will be regenerated in the space from which the defective portion is removed. However, in some embodiments the space below the upper cover is left empty; if desired, biological material may be implanted as a discrete element or could be injected intraoperatively or postoperatively for example.

To reduce the stress on the upper surface of the device, a lubricant may be affixed or applied to the toughened surface of the implant. For example, a lubricant such as hyaluronic acid may be affixed to the upper surface of the device by cross-linking. Other lubricants can also be used. Reference is made to U.S. patent application Ser. No. 10/195,606 entitled "Cartilage Repair and Regeneration Device and Method", filed concurrently herewith, which is incorporated by reference herein in its entirety.

One embodiment, therefore, is a composite device comprising a cover of naturally occurring ECM and a framework therebelow provided to accommodate the regeneration. With the mass of comminuted ECM, the device serves as a cushion for the condyle load and a bearing surface for the condyle. By placing the device into close contact with the remaining portion of the meniscus, the regeneration will take place.

In another embodiment of the present invention, the device comprises a shell shaped conformingly to fit into the space occupied by the removed meniscus portion, the shell to provide an upper surface to withstand the articulation of the knee and a space below the upper surface. A bioactive agent, biologically derived agent, cells, biocompatible polymer, biocompatible inorganic material, biological lubricant or combinations thereof is disposed within the space. It will be appreciated that shells of different size and shape will be provided to surgeons such that they can remove a portion of the damaged meniscus conforming to the shape of a device to be inserted or size the shell to conform to the removed portion of damaged meniscus. Templates can be provided to guide the surgeon in the removal of the defective portion. Preferably, the device is shaped to conform to the space into which it is inserted such that the surrounding tissue of the remaining meniscus is in contact with the device. It has been found, for example, that a plug made from comminuted ECM such as SIS may be inserted into a hole in a meniscus to regenerate the meniscus and close the hole. Such a plug may be wrapped or covered with layers of SIS.

For handling purposes, the devices will preferably be made in a factory and supplied to the surgeons for selection and use based on size and shape. In some embodiments, the devices will be provided in dried or lyophilized condition to be hydrated by the surgeon. Portions of the exterior of the device, particularly those portions providing communication with the biological mass under the upper cover, may be perforated to expedite the hydration of the device.

In some embodiments, the device for regenerating a meniscus or a portion thereof comprises a wedge-shaped biological scaffold material body having an apex portion and a base portion spaced radially outwardly from the apex portion. The body provides an upper surface to face a condyle of the femur and to provide for articulation of the knee against the upper surface and a lower surface to face the tibial platform of the knee. This body, which may be fabricated from sheets or strips of naturally occurring ECM, is formed to provide a plurality of channels or compartments disposed between the upper and lower surfaces. In some embodiments, the channels or compartments extend radially inwardly from the base portion to the apex portion. In other embodiments, the channels or compartments extend circumferentially about the device, i.e., in the circumferential direction of the original meniscus. In some embodiments, the radially extending channels will be generally conical in shape with their large ends disposed toward the base portion and their smaller ends disposed toward the apex portion. In some embodiments, the circumferential channels will be arranged such that smaller diameter channels will be disposed toward the apex portion and larger diameter channels will be disposed adjacent the base portion.

These channels or compartments may be filled with comminuted naturally occurring ECMs to provide a framework for meniscus regeneration. In some embodiments, the comminuted ECM will be mixed with or replaced by bioactive agents, biologically-derived agents, cells, biological lubricants, biocompatible inorganic materials, biocompatible polymers and/or combinations thereof. The ECM material providing the upper surface and the lower surface may be laminated sheets or strips of an ECM material such as SIS which may be formed under pressure and heat. It will be appreciated that lyophilization may be used to dry the mass of comminuted material.

It will be appreciated that various structures may be provided within the concept of the present disclosure to produce a composite device having an upper cover made from a toughened sheet of a naturally occurring ECM with a mass of comminuted naturally occurring ECM therebelow to accommodate the regeneration of the meniscus. For example, a device for regenerating a meniscus or a portion thereof may comprise a wedge-shaped body having radially extending or circumferentially extending compartments or channels into which the comminuted ECM is placed. The upper or lower panels may merely serve as covers for the device's internal structure which may be made separately from the panels as will be further described herein. In some embodiments, the devices are made in the shape of a pillow, the upper and lower covers of which provide an interior space which is filled with a biological material to provide a framework for meniscus regeneration. Channels or compartments within the space between the upper and lower covers may be fabricated, for example, with partitions of ECM material to direct the regeneration. In some cases, the channels or compartments will extend radially inwardly and in other cases, the channels or compartments will extend circumferentially.

Various systems may be provided for forming naturally occurring ECMs such as SIS layers or strips to provide the panels or covers and to provide the recesses, channels or compartments in between the panels or covers. It has been found that layers of harvested and cleaned SIS may be drawn into cavities in vacuum forming operations. Such layers of SIS may be formed and then laminated together and dried by the application of heat and pressure. The mass of biological material such as the comminuted SIS may be placed in the vacuum formed cavities as part of the forming process.

The present invention also comprises a method of regenerating a portion of a knee meniscus comprising the steps of removing a segment of a meniscus to provide a partial meniscal space extending circumferentially about a predetermined portion of the tibial platform and leaving remaining segments of the original meniscus. This partial meniscal space will have a radially outer portion and a radially inner portion. The method involves providing an implant device constructed from naturally occurring ECMs and shaped to conform to the partial meniscal space. The device is placed into the space and then attached to the adjacent tissue of the knee. The method encourages regeneration from the radially outer portion of the device to the radially inner portion of the device. In embodiments of the present invention, the encouraging step comprises channeling blood flow from the vascular rich outer portion of the meniscus and the device to the radially inner portion of the device. The regeneration is encouraged by structuring the device such that the vascular rich portion of the original meniscus and the adjacent radially outer portion of the original meniscus will work with the device and particularly the mass of biological material under the upper cover of the device to regenerate the meniscal tissue.

In one embodiment, the method of the present invention, therefore, comprises the steps of replacing a portion of the original meniscus with a naturally occurring extracellular matrix material shaped and formed to provide an upper surface toughened to withstand the compression and shear stress of articulation of the knee and an interior space into which the meniscal regeneration occurs and attaching the material to the surrounding tissue to provide blood flow to the device. In some embodiments, the interior space is filled with a mass of comminuted naturally occurring extracellular matrix material, bioactive agents, biologically-derived agents, cells or various combinations thereof. In some embodiments, the comminuted ECM may be chemically cross-linked by chemical agents such as aldehydes, carbodiamide, glycation agents, enzymes or the like. See, for example, U.S. Pat. No. 6,042,610, already incorporated by reference, at columns 11-12. In some embodiments, the comminuted ECM may be physically cross-linked by heat (thermal cross-linking), radiation (ultraviolet or gamma irradiation), or combinations such as drying at elevated temperatures (dehydrothermal crosslinking). And in some embodiments a lubricating agent may be applied or affixed to the device.

For handling and installation purposes, some embodiments comprise a cover over a recess which is filled with biological materials and constructed to provide a framework for meniscus regeneration. At least the upper cover is formed from a material which will withstand the compression and shear stresses involved in articulation of the femur on the tibia, i.e., of the condyles on the tibia platform. It will be appreciated that this is a dynamic stress situation for the upper cover and, for that matter, for the device attached to the surrounding tissue or anchored in the space from which the defected meniscus portion is removed. This upper cover of the device may be provided by treating layers of ECM with heat and pressure to form a toughened upper surface.

In this specification and in the appended claims, unless expressly limited otherwise, it is intended that "toughened" or "treatment for toughening" shall involve treating ECM such as SIS with various treatment steps including such steps as laminating several layers of ECM strips together and treating the layers with compression and vacuum or heat or combinations of pressure, vacuum, and heat. It is contemplated that such layers may be laminated together and bonded by both mechanical compression and application of vacuum and/or heated air which accomplishes the bonding and also dries the product, leading to a dehydrated product. It has been found that several layers of SIS can be laminated together with heat, vacuum, and pressure to provide a portion of the composite structure. Illustratively, in some embodiments, both the upper cover and the lower cover defining the shell of the device are treated with heat and pressure to remove water from the ECM comprising the shell to produce a shell comprising a dehydrated naturally occurring extracellular matrix. It has been found that various drying conditions affect the toughness of the ECM. For example, changing the platen or drying surface in vacuum drying by reducing the size of the openings in the platen can increase the toughness of the resultant ECM. Drying in air or hot air, as compared to in vacuum, can also produce a dehydrated extracellular matrix having increased toughness. Any method to increase density, for example by increasing the number of layers of ECM in a given volume, will also increase toughness. Altering the orientation of layers, selecting older animals, selecting species having tougher ECMs, and processing techniques (for example, increasing concentration of peracetic acid or pressure from rollers) can also affect the toughness of the resultant ECM.

Unless otherwise expressly limited, "toughened" or "treatment for toughening" may also include other means of cross-linking ECM. As discussed above, the ECM can be chemically crosslinked to increase the toughness of all or a portion of the ECM through the use of agents such as aldehydes, carbodiimides, glycation agents, enzymes and the like. In addition, as discussed above, other methods of crosslinking the ECM may be used. For example, radiation (including UV, RF, and gamma radiation) could be used to toughen the ECM. When UV or RF radiation is used, preferably the ECM is crosslinked prior to final drying. Additionally, combinations of methods may be used, such as be drying at elevated temperatures (dehydrothermal crosslinking). All of such methods are intended to be included in the expressions "toughened" and "treatment for toughening" unless expressly limited.

In this specification and claims, unless expressly limited otherwise, "generally wedge-shaped" is intended to define the shape of a device that has a thick base portion and a thin apex portion, wherein the device tapers between the thick base portion and the thin apex portion. Although a generally wedge-shaped device can have flat upper and lower surfaces (see, e.g., FIG. 12), such a device can also have one or more surfaces that are curved, such as a tapering convex surface (see, e.g. FIG. 49) or a tapering concave surface, or could have stepped or contoured surfaces that follow the contour of any underlying material.

In this specification and claims, unless otherwise expressly limited, "mass of biological material" is intended to include naturally occurring extracellular matrix, bioactive agents, and/or biologically-derived agents and cells. "Mass of biological material" is also intended to include biological materials formed in whole or in part from such matrices, agents and cells. Thus, "mass of biological material" includes comminuted extracellular matrix and extracellular matrix foams as disclosed in U.S. patent application Ser. No. 10/195,354 entitled "Porous Extracellular Matrix Scaffold and Method", and hybrid materials, as disclosed in U.S. patent application Ser. No. 10/195,341 entitled "Hybrid Biologic/Synthetic Porous Extracellular Matrix Scaffolds", all of which are filed concurrently herewith, and U.S. patent application Ser. No. 10/172,347 entitled "Hybrid Biologic-Synthetic Bioabsorbable Scaffolds" which was filed on Jun. 14, 2002, the disclosures of which are incorporated by reference herein. Unless otherwise expressly limited, "mass of biological material" includes material from which commercially available products are made, including, for example: the RESTORE® Orthobiologic Implant, available from DePuy Orthopaedics, Inc. of Warsaw, Indiana; OASIS and SURGISIS products available from Cook Biotech, Inc. of Bloomington, Indiana; "TISSUEMEND" available from TEI Biosciences Inc. of Boston, Mass.; and GRAFTPATCH, FORTAFLEX, FORTAGEN and FORTAPERM products available from Organogenesis, Inc. of Canton, Mass. Unless expressly limited otherwise, the expression "mass of biological material" is also intended to encompass purified collagen, such as that disclosed in U.S. Pat. No. 6,042,610. The expression "mass of biological material" is intended to encompass all such materials regardless of whether they include another material, regardless of their physical state (e.g. powder or foam), and regardless of whether they are cross-linked or otherwise toughened, unless otherwise expressly stated. The expression "mass of biological material" should be understood to encompass both materials that are integral and that which comprise discrete elements. "Mass of biological material" should also be understood to encompass all forms of these materials, including dry forms, solutions, dispersions, gels, and pastes for example. Specific examples of materials for the mass of biological materials include: comminuted ECM; ECM pieces; ECM foam; an ECM roll; woven ECM; a non-woven ECM mat; braided ECM; ECM solution; ECM dispersion; ECM slurry; ECM gel; ECM paste; and ECM that has not been toughened. Such ECMs include but are not limited to: comminuted SIS; SIS pieces; SIS foam; an SIS roll; woven SIS; non-woven SIS mat; braided SIS; SIS solution; SIS dispersion; SIS slurry; SIS gel; SIS paste; and SIS that has not been toughened.

In the specification and claims, "comminuted" is intended to mean reduced to pieces. "Piece" and "pieces" are intended to mean any fiber, strip, ribbon, sliver, filament, shred, bit, fragment, part, flake, slice, cut, chunk, or other portion of solid or solid-like material. "Comminuted" is not intended to imply any particular means of producing the pieces. No particular shape is intended to be implied by the use of the word "comminuted" unless otherwise expressly limited; the pieces can comprise a variety of two and three dimensional shapes of material. Moreover, unless a specific size of material is specified, the use of the term "comminuted" is not intended to imply any particular size of pieces.

"Bioactive agents" include one or more of the following: chemotactic agents; therapeutic agents (e.g. antibiotics, steroidal and non-steroidal analgesics and anti-inflammatories, anti-rejection agents such as immunosuppressants and anti-cancer drugs); various proteins (e.g. short chain peptides, bone morphogenic proteins, glycoprotein and lipoprotein); cell attachment mediators; biologically active ligands; integrin binding sequence; ligands; various growth and/or differentiation agents (e.g. epidermal growth factor, IGF-I, IGF-II, TGF-β I-III, growth and differentiation factors, vascular endothelial growth factors, fibroblast growth factors, platelet derived growth factors, insulin derived growth factor and transforming growth factors, parathyroid hormone, parathyroid hormone related peptide, bFGF; $TGF_{62}$ superfamily factors; BMP-2; BMP-4; BMP-6; BMP-12; sonic hedgehog;

GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. If other such substances have therapeutic value in the orthopaedic field, it is anticipated that at least some of these substances will have use in the present invention, and such substances should be included in the meaning of "bioactive agent" and "bioactive agents" unless expressly limited otherwise.

"Biologically derived agents" include one or more of the following: bone (autograft, allograft, and xenograft) and derivates of bone; cartilage (autograft, allograft, and xenograft), including, for example, meniscal tissue, and derivatives; ligament (autograft, allograft, and xenograft) and derivatives; derivatives of intestinal tissue (autograft, allograft, and xenograft), including for example submucosa; derivatives of stomach tissue (autograft, allograft, and xenograft), including for example submucosa; derivatives of bladder tissue (autograft, allograft, and xenograft), including for example submucosa; derivatives of alimentary tissue (autograft, allograft, and xenograft), including for example submucosa; derivatives of respiratory tissue (autograft, allograft, and xenograft), including for example submucosa; derivatives of genital tissue (autograft, allograft, and xenograft), including for example submucosa; derivatives of liver tissue (autograft, allograft, and xenograft), including for example liver basement membrane; derivatives of skin (autograft, allograft, and xenograft); platelet rich plasma (PRP), platelet poor plasma, bone marrow aspirate, demineralized bone matrix, insulin derived growth factor, whole blood, fibrin and blood clot. Purified ECM and other collagen sources are also intended to be included within "biologically derived agents." If other such substances have therapeutic value in the orthopaedic field, it is anticipated that at least some of these substances will have use in the present invention, and such substances should be included in the meaning of "biologically-derived agent" and "biologically-derived agents" unless expressly limited otherwise.

"Biologically derived agents" also include bioremodelable collageneous tissue matrices. The expressions "bioremodelable collagenous tissue matrix" and "naturally occurring bioremodelable collageneous tissue matrix" include matrices derived from native tissue selected from the group consisting of skin, artery, vein, pericardium, heart valve, dura mater, ligament, bone, cartilage, bladder, liver, stomach, fascia and intestine, tendon, whatever the source. Although "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers. The term "bioremodelable collageneous tissue matrices" includes "extracellular matrices" within its definition.

"Cells" include one or more of the following: chondrocytes; fibrochondrocytes; osteocytes; osteoblasts; osteoclasts; synoviocytes; bone marrow cells; mesenchymal cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited otherwise. Illustratively, in one example of embodiments that are to be seeded with living cells such as chondrocytes, a sterilized implant may be subsequently seeded with living cells and packaged in an appropriate medium for the cell type used. For example, a cell culture medium comprising Dulbecco's Modified Eagles Medium (DMEM) can be used with standard additives such as non-essential amino acids, glucose, ascorbic acid, sodium pyruvate, fungicides, antibiotics, etc., in concentrations deemed appropriate for cell type, shipping conditions, etc.

"Biological lubricants" include: hyaluronic acid and its salts, such as sodium hyaluronate; glycosaminoglycans such as dermatan sulfate, heparan sulfate, chondroiton sulfate and keratan sulfate; synovial fluid and components of synovial fluid, including as mucinous glycoproteins (e.g. lubricin), tribonectins, articular cartilage superficial zone proteins, surface-active phospholipids, lubricating glycoproteins I, II; vitronectin, and rooster comb hyaluronate. "Biological lubricant" is also intended to include commercial products such as ARTHREASE™ high molecular weight sodium hyaluronate, available in Europe from DePuy International, Ltd. of Leeds, England, and manufactured by Bio-Technology General (Israel) Ltd., of Rehovot, Israel; SYNVISC® Hylan G-F 20, manufactured by Biomatrix, Inc., of Ridgefield, N.J. and distributed by Wyeth-Ayerst Pharmaceuticals of Philadelphia, Pa.; HYLAGAN® sodium hyaluronate, available from Sanofi-Synthelabo, Inc., of New York, N.Y., manufactured by FIDIA S.p.A., of Padua, Italy; and HEALON® sodium hyaluronate, available from Pharmacia Corporation of Peapack, N.J. in concentrations of 1%, 1.4% and 2.3% (for opthalmologic uses). If other such substances have therapeutic value in the orthopaedic field, it is anticipated that at least some of these substances will have use in the present invention, and such substances should be included in the meaning of "biological lubricant" and "biological lubricants" unless expressly limited otherwise.

"Biocompatible polymers" is intended to include both synthetic polymers and biopolymers (e.g. collagen). Examples of biocompatible polymers include: polyesters of [alpha]-hydroxycarboxylic acids, such as poly(L-lactide) (PLLA) and polyglycolide (PGA); poly-p-dioxanone (PDS); polycaprolactone (PCL); polyvinyl alcohol (PVA); polyethylene oxide (PEO); polymers disclosed in U.S. Pat. Nos. 6,333,029 and 6,355,699; and any other bioresorbable and biocompatible polymer, co-polymer or mixture of polymers or co-polymers that are utilized in the construction of prosthetic implants. In addition, as new biocompatible, bioresorbable materials are developed, it is expected that at least some of them will be useful materials from which portions of the devices may be made. It should be understood that the above materials are identified by way of example only, and the present disclosure is not limited to any particular material unless expressly called for in the claims.

"Biocompatible inorganic materials" include materials such as hydroxyapatite, all calcium phosphates, alpha-tricalcium phosphate, beta-tricalcium phosphate, calcium carbonate, barium carbonate, calcium sulfate, barium sulfate, polymorphs of calcium phosphates, sintered and non-sintered ceramic particles and combinations of such materials. If other such substances have therapeutic value in the orthopaedic field, it is anticipated that at least some of these substances will have use in the present invention, and such substances should be included in the meaning of "biocompatible inorganic material" and "biocompatible inorganic materials" unless expressly limited otherwise.

It is expected that various combinations of bioactive agents, biologically derived agents, cells, biological lubricants, biocompatible inorganic materials, biocompatible polymers can be used with the scaffolds of the present invention. Various techniques may be used to fix the devices of the present invention. Examples of suitable devices and methods are disclosed in U.S. Patent Application "Unitary Surgical Device and Method", filed concurrently herewith and incorporated by reference herein in its entirety. Reference is also made to the following applications for filed concurrently herewith and incorporated by reference herein: U.S. patent application Ser. No. 10/195,719 entitled "Devices from Naturally Occurring Biologically Derived Materials"; and U.S. Patent Application Serial No. "Cartilage Repair Apparatus and Method"). To facilitate fixation of the devices to surrounding tissue, the lower cover or the upper cover may be extended. In some cases, the extension of the lower cover or upper cover will be provided with tacks to facilitate the attachment of the device to surrounding tissues. One or more of the layers of the material forming the upper cover or the lower cover may be formed to provide tabs extending away from the device to facilitate attachment of the device to the surrounding tissue.

A repair device may be made in accordance with the present invention in a form such that it can be pulled into, or otherwise placed within, the faces of a tear in a meniscus to extend along the tear. The device comprises strips of naturally occurring ECM material laminated together to form a body portion and at least one extension portion extending away from the body portion. The body portion is shaped to be pulled by the extension portion into the tear to extend along and fill the tear. This body portion may comprise a mass of comminuted naturally occurring ECM captured between the strips to serve as a framework for closing or regenerating the tear. The body portion may be divided into a series of compartments which may be pulled into a tear with a space between each compartment such that the surgeon may trim the device between the compartments.

Thus, one aspect of this disclosure is a device for regenerating a meniscus or a portion thereof, the device comprising a wedge-shaped body having an upper panel and a lower panel angularly separated to define an apex portion and a base portion, the panels being formed of a naturally occurring extracellular matrix.

Another aspect of this disclosure is a device for regenerating a knee meniscus or a portion thereof, the device comprising a wedge-shaped body formed from a naturally occurring extracellular matrix having an apex portion and a base portion spaced radially outwardly from the apex portion, the body providing an upper surface to face a condyle of a femur of the knee and provide an articulation surface therefor and a lower surface to face a tibial platform of the knee, the body providing a plurality of channels disposed between the upper and lower surfaces.

Yet another aspect of this disclosure is a device for regenerating a meniscus of a knee or a portion thereof, the device comprising a shell made from a toughened naturally occurring extracellular matrix and a biologic material to provide a framework for meniscus regeneration disposed in the shell.

Still another aspect of this disclosure is a device for regenerating the meniscus of a knee or a part thereof, the device comprising a plurality of layers of naturally occurring extracellular matrix material laminated together and formed in the shape of a meniscus with an outer radial portion, an inner radial portion and opposite end portions, one or more of the layers being formed to provide a plurality of tabs extending away from the device to be attached to the surrounding tissue of the knee to attach the device.

A further aspect of this disclosure is an implant for regenerating a meniscus or portions of a meniscus on a tibial platform to serve as a support bearing for a condyle above the platform, the implant comprising an outer cover formed from sheets of a naturally occurring extracellular matrix material layered together and formed and toughened by dehydrothermal cross-linking to provide a bearing surface to withstand the forces generated by articulation of the condyle relative to the platform and a biological material below the cover to provide a framework for regenerating the meniscus.

Another aspect of this disclosure is an implant for regenerating a portion of a meniscus in the knee, the implant comprising an outer cover providing a cavity, an upper surface to face the femur of the knee and a lower surface to face the tibial platform of the knee, the cavity being disposed between the surfaces of the cover, the outer cover being formed from a material selected from the group consisting of SIS, stomach submucosa, bladder submucosa, alimentary submucosa, respiratory submucosa, genital submucosa, and liver basement membrane, the upper surface being toughened by cross-linking the collagen fibers, and the cavity being filled with a material selected from the group consisting of blood clots, fibrin, comminuted ECMs and PRP.

An additional aspect of this disclosure is an implant for regenerating a portion of a meniscus in a knee, the implant having a radially outer portion, a radially inner portion, an upper surface and a lower surface, the outer and inner portions being curved to conform to the outer and inner portions, respectively, of the portion of the meniscus to be regenerated, the implant having an outer shell defining the outer and inner portions and upper and lower surfaces, the outer shell being formed from naturally occurring extracellular matrix material, and at least the upper surface being toughened, the shell having a space therein, and a biological material disposed in the space to provide a framework for regenerating the meniscus.

A further aspect of this disclosure is an implant for regenerating a knee meniscus or a portion thereof, the implant having radially outer and inner portions corresponding to the radially outer and inner portions of the portion of the meniscus to be regenerated, and an outer shell providing an inner space extending from the outer portion to the inner portion, the outer shell having an upper surface to be engaged by the femur of the knee and a lower surface to be supported on the tibial platform of the knee, the outer shell being formed from a plurality of layers of SIS laminated together and treated to be toughened to withstand the shearing and compressive forces in the knee in vivo, and at least one material selected from the group consisting of fibrin, blood clots, comminuted SIS and PRP disposed in the space to accommodate the meniscus regeneration.

In another aspect of this disclosure a method is provided for regenerating a portion of a knee meniscus having a radially outer portion and a radially inner portion, the meniscus portion extending circumferentially about a medial or a lateral portion of the tibial platform of the knee, the method comprising the steps of: removing a segment of a meniscus to provide a meniscal space extending circumferentially about a predetermined portion of the tibial platform and leaving remaining segments of the original meniscus, the meniscal space having a radially outer portion and a radially inner portion, providing an implant device constructed from a naturally occurring extracellular matrix to conform to the meniscal space and placing the device into the space, the device having a radially outer portion and a radially inner portion, attaching the device to the adjacent tissue of the knee, and encouraging in regeneration from the radially outer portion of the device to the radially inner portion of the device.

In yet another aspect of this disclosure a method is provided for regenerating a meniscus or a portion thereof comprising the steps of: replacing a portion of an original meniscus with a naturally occurring extracellular matrix material shaped to conform to the meniscus portion removed, and shaping the material such that in vivo the material defines channels extending from the radially outer portion of the meniscus to the radially inner portion of the meniscus to support the regeneration.

In a further aspect of this disclosure a method is provided for regenerating a knee meniscus or a portion thereof comprising the steps of: replacing a portion of an original meniscus with a naturally occurring extracellular matrix material shaped and formed to provide an upper surface toughened to withstand the compression and shear stress of articulation of the knee and an interior space into which meniscal regeneration occurs, and attaching the material to the surrounding tissue.

Still another aspect of this disclosure is a device for regenerating a removed portion of a knee meniscus, the device comprising a shell shaped conformingly to fit into the space occupied by the removed meniscus portion, the shell providing an upper surface to withstand the articulation of the knee and a space under the upper surface, and a biologically derived agent, said biologically derived agent comprising a material selected from the group consisting of comminuted naturally occurring extracellular matrix, fibrin, blood clot and platelet rich plasma (PRP) disposed within the space.

Yet another aspect of this disclosure is a composite device for insertion into a space in a knee meniscus from which space a meniscus portion has been removed, the device comprising an upper cover made from a toughened sheet of naturally occurring extracellular matrix (ECM), the cover defining therebelow a space, and a mass comprising comminuted naturally occurring ECM disposed in the space.

Still another aspect of this disclosure is a plug to be inserted into an opening formed in a knee meniscus, the plug comprising a mass of comminuted naturally occurring ECM formed into the shape of a plug.

A further aspect of this disclosure is a device for repairing a tear in a knee meniscus, the device comprising strips of naturally occurring extracellular matrix laminated together to form a body portion and at least one extension portion extending away from the body portion, the body portion being shaped to be pulled by the extension portion into the tear to extend along and fill the tear.

Moreover, an additional aspect of this disclosure is a device for regenerating a meniscus or a portion thereof, the device comprising a wedge-shaped body having an upper panel and a lower panel angularly separated to define an apex portion and a base portion, the panels being formed of a naturally occurring extracellular matrix, and a support structure disposed between the upper panel and lower panel, the support structure comprising one or more members of rigid and hardened naturally occurring extracellular matrix.

One more aspect of this disclosure is an implantable device for repairing or regenerating at least a portion of a meniscus of a knee, the device comprising a toughened laminate including layers of ECM, the layers of ECM being toughened by a method selected from the group consisting of: compressing the layers of ECM together with heat to form the toughened laminate; compressing the layers of ECM together with vacuum to form the toughened laminate; compressing the layers of ECM together with pressure to form the toughened laminate; mechanically pressing the layers of ECM together while heating the layers to form the toughened laminate; and cross-linking the ECM laminate.

Still another aspect of this disclosure is an implantable device for repairing or regenerating at least a portion of a meniscus of a knee, the device comprising a toughened outer surface and a mass of biological material to provide a framework for meniscus regeneration, at least part of the mass of biological material being covered by the toughened outer surface.

Yet another aspect of this disclosure is an implantable device for repairing or regenerating at least a portion of a meniscus of a knee, the device comprising a wedge-shaped body having an upper panel and a lower panel angularly separated to define an apex portion and a base portion, at least part of the device comprising naturally occurring ECM.

In an additional aspect of this disclosure an implantable device is provided for regenerating at least a portion of a meniscus of a knee, the device comprising a cover sheet and a mass of biological material, the cover sheet extending over and beyond the mass of biological material.

Yet another aspect of this disclosure is an implantable device for regenerating at least a portion of a meniscus of a knee, the device comprising a plurality of surfaces defining compartments, a mass of biological material in each compartment, and a cover extending over the compartments and masses of biological material.

Still another aspect of this disclosure is an implantable device for regenerating at least a portion of a meniscus of a knee, the device comprising at least two adjacent materials having different densities, wherein each of the materials comprises ECM, wherein at least one of the material is treated to increase its density.

An additional aspect of this disclosure is an implantable device for repairing or regenerating at least a portion of vertebrate tissue, the device comprising a sheet of naturally occurring ECM having a density of at least 0.9 gm/cm$^3$.

One more aspect of this disclosure is an implantable device for repairing or regenerating at least a portion of a meniscus of a knee, the device comprising a toughened laminate including layers of naturally occurring bioremodelable collageneous matrix, the laminate being toughened by a method selected from the group consisting of: compressing the layers of naturally occurring bioremodelable collageneous matrix together with heat to form the toughened laminate; compressing the layers of naturally occurring bioremodelable collageneous matrix together with vacuum to form the toughened laminate; compressing the layers of naturally occurring bioremodelable collageneous matrix together with pressure to form the toughened laminate; mechanically pressing the layers of naturally occurring bioremodelable collageneous matrix together while heating the layers to form the toughened laminate; and cross-linking the naturally occurring bioremodelable collageneous matrix laminate.

A final aspect of this disclosure is an implantable device for repairing or regenerating at least a portion of vertebrate tissue, the device comprising a sheet of naturally occurring bioremodelable collageneous matrix toughened to have a density of at least 0.9 gm/cm$^3$.

The above and other features of the present disclosure will become apparent from the following description and the attached drawings.

BRIEF DESCRIPTION OF THE DRAWINGS

In the drawings:

FIG. 20 shows how individual compartments may be formed from sheets of material such as SIS;

FIG. 20(a) shows a plurality of mandrels about which SIS is wrapped to form a plurality of channels;

FIG. 21 shows a single cylindrically-shaped compartment of the SIS material;

FIG. 22 shows a plurality of such cylindrical compartments extending in a circumferential direction (about the meniscus) with the radially outer compartments being larger then the radially inner compartments and with the compartments contained within a sheet of SIS formed to cover the compartments, the compartments being filled with a biological material such as comminuted SIS;

FIG. 23 shows a device made in accordance with FIG. 22;

FIG. 36 shows the formation of a wedge-shaped pocket in a panel of SIS to be folded about an apex;

FIG. 37 shows the pocket in FIG. 36 filled with a material such as comminuted SIS with a portion of the panel closing the pocket;

FIG. 38 shows the bottom of the FIG. 36 and FIG. 37 structure;

FIG. 39 shows the structure of FIGS. 36-38 attached to a meniscus;

DETAILED DESCRIPTION OF THE DRAWINGS

Figure 1:
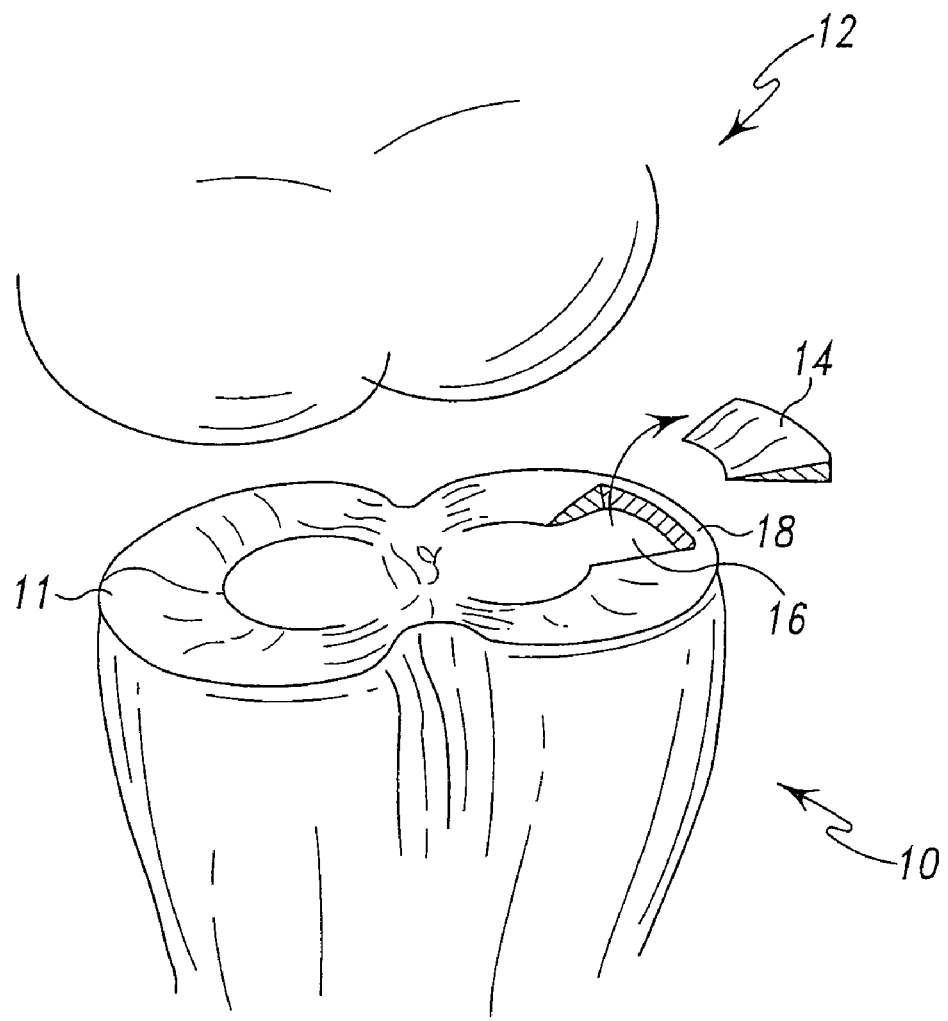
FIG. 1 is a diagrammatical view showing a tibial platform with a typical meniscus structure on the platform and a portion of the meniscus removed for illustration purposes, the tibia platform being below the condyles of the femur.

Referring to FIG. 1, it will be seen that a tibial platform 10 below the condyles 12 of a knee support a meniscus 11 from which an illustrative defective portion 14 is removed to leave a wedge-shaped space 16. In the removal process, the surgeon will generally leave an outer rim 18 of the meniscus. It is well known that the radially outer portion of a meniscus is richly vascularized while the radially inner portion of a meniscus is not so well vascularized. Menisci have been described by people working in the orthopaedic field to be two semi-lunar, wedge-shaped concave fibrocartilagenous structures anchored to the tibia plateau (such as shown at 10) in the knee. The menisci provide a large surface of articulation between the otherwise incongruent surfaces of the tibia platform or plateau and the femur condyles (such indicated at 12). The menisci serve to reduce contact stresses and wear in the knee joint. The peripheral rim of the meniscus at the menisco-synovial junction is highly vascular (red zone) whereas the inner two-third portion of the meniscus is completely avascular (white zone), with a small transition (red-white zone) between the two. Degenerative or traumatic tears to the meniscus which result in partial or complete loss of function frequently occur in the white zone. Such tears result in unstable flaps of meniscal tissue in the knee joint causing, in the short term, severe joint pain and locking, and in the long term, a loss of meniscal function leading to osteoarthritis. The current standard-of-care involves partial meniscectomy to remove unstable tissue to relieve joint pain and locking. However, when the resected tissue is from the avascular (white zone), the meniscus has little potential for self regeneration. Thus, the current standard-of-care results in partial but permanent loss of meniscal tissue, making the joint susceptible to osteoarthritis.

The portion 14 removed from the structure shown in FIG. 1 includes a portion of the original meniscus which is within the avascular zone, particularly the radially inner portion.

Figure 2:
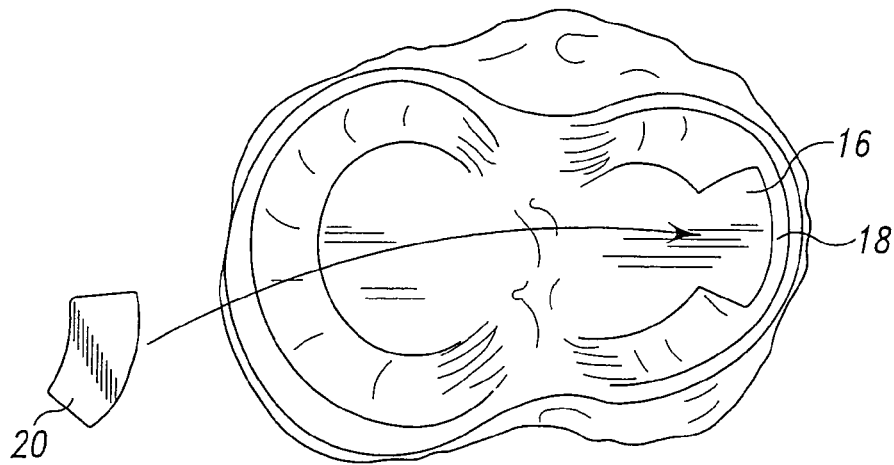
FIG. 2 is a view looking down at the tibial platform and showing diagrammatically the insertion of an illustrative meniscus repair device to replace the portion of the meniscus removed.
Figure 3:
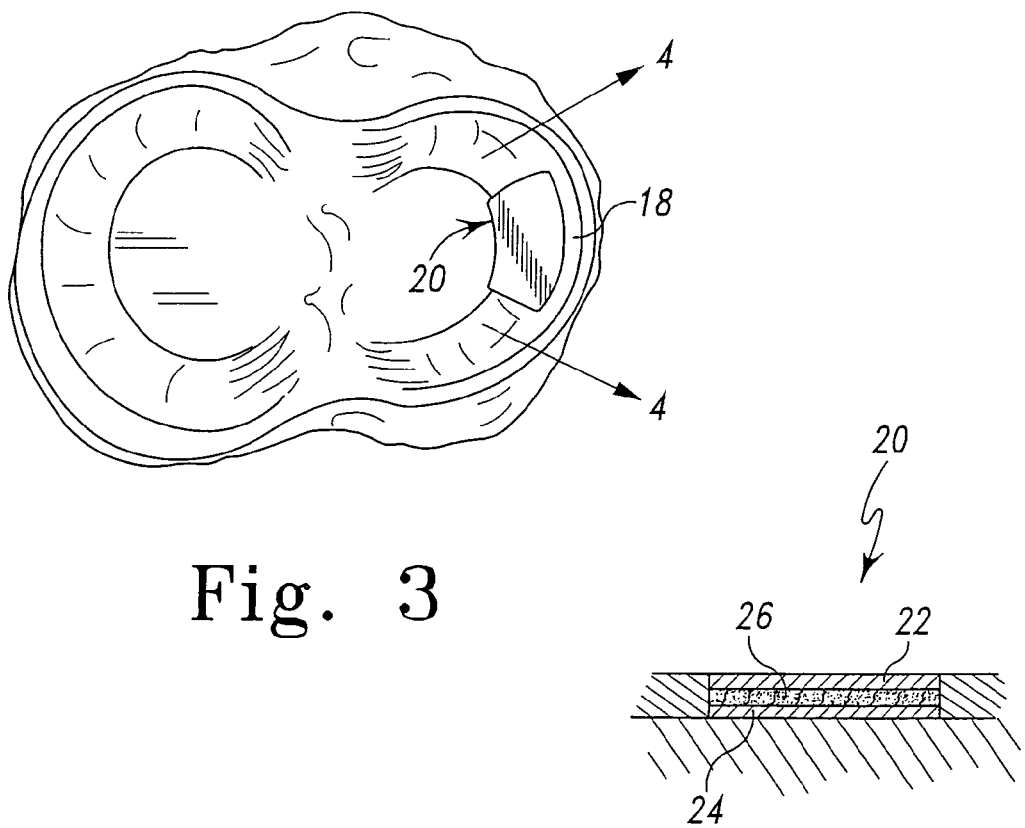
FIG. 3 shows the inserted device in a position to be attached to the portions of the meniscus remaining after the injured portion is removed.
Figure 4:
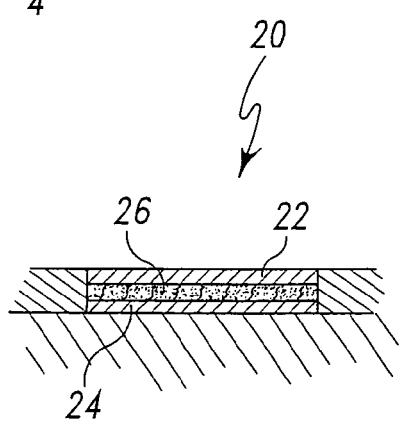
FIG. 4 is a sectional view taken from FIG. 3 along the lines 4-4.

FIG. 2 shows how a device 20 made in accordance with the present invention may illustratively be inserted into the space 16 to be against the outer rim 18. This illustrative device 20 is shown in FIGS. 3 and 4 in position filling the space 16 and against the rim 18 left by the surgeon. FIG. 4 shows the device as comprising an upper cover or upper panel 22 and a lower cover or lower panel 24. These panels 22, 24, which may illustratively be angularly related, will define an internal space 26 between the covers. Internal space 26 may be filled with a biological material or a biological structure providing a framework for regeneration of the meniscus into the space 16.

FIGS. 1-4, therefore, show the general concept of the present invention in which a generally wedge-shaped device 20 is inserted into the knee to fill a space 16 from which a defective portion of a meniscus has been removed. FIG. 2 suggests that the device 20 may be inserted, for example, in arthroscopic surgery through portals provided in the outer anterior surface of the knee opening into the knee cavity between the condyles 12 and the tibial platform 10. It will be appreciated that the device 20 will be inserted downwardly and inwardly through an opening to be placed into the space 16. It will also be appreciated that the device 20 may be anchored in some fashion in the space 16 such that it is in contact with the boundaries of the space as suggested in FIGS. 3 and 4. The upper cover 22 of the device 20 will serve as a bearing surface for the condyle 12 disposed thereabove and be subjected to the compression and stress forces involved in articulation of the knee. The condyle will move upon the upper surface of the cover 22. The device 20 will serve as a cushion or pillow for handling the compression load provided by the knee.

Figure 5:
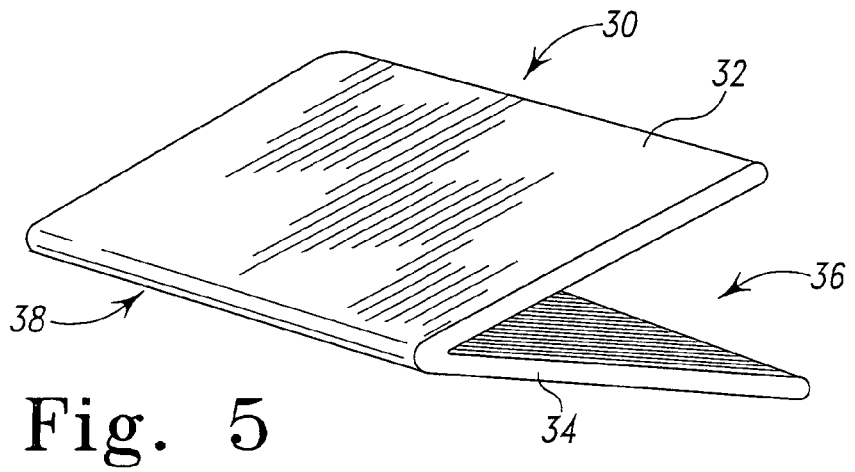
FIG. 5 is a perspective view showing an open wedge-shaped device comprising an upper panel and a lower panel angularly separated to define an apex portion and a base portion.
Figure 6:
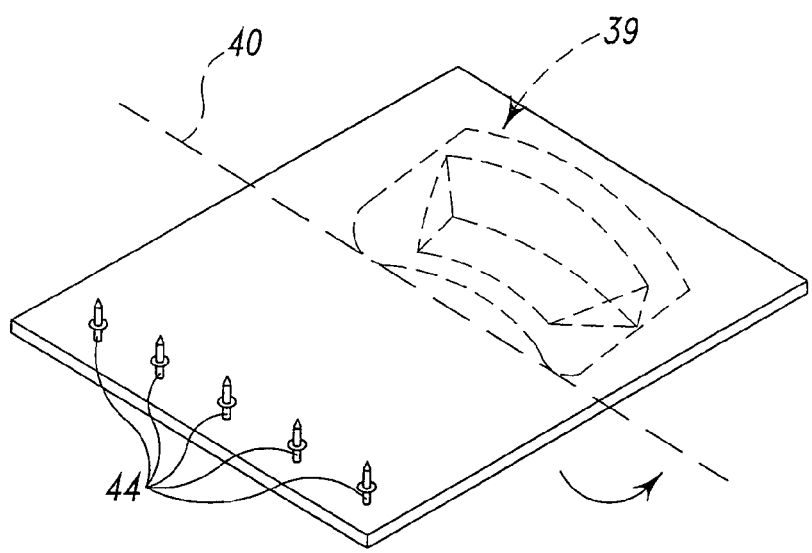
FIG. 6 shows a wedge shaped device prior to folding with a pocket shown in imaginary lines formed in the device.
Figure 7:
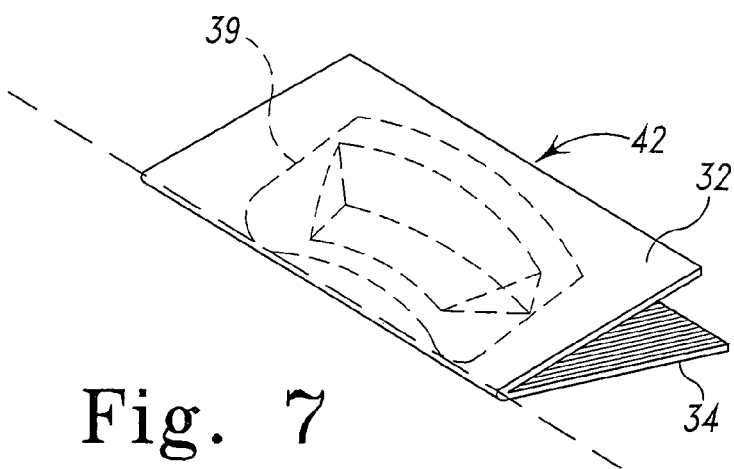
FIG. 7 shows a further step in the process in making the device shown in FIG. 6 to produce a filled, wedge-shaped device.

Turning to FIGS. 5, 6 and 7, it will be seen that an illustrative concept of a regeneration device is somewhat diagrammatically illustrated. The illustrative device 30 includes an upper panel 32 and a lower panel 34 defining a wedge-shaped device having a base portion 36 and an apex portion 38. The device 30 illustrated in FIGS. 5, 6 and 7 illustrates that a plurality of layers of a naturally occurring ECM such as SIS may be layered together and formed to provide a generally wedge-shaped device. FIG. 6 suggests that the device may include a formed cavity 39 (illustrated in phantom) and that the device may be folded about a fold line 40 to provide a device such as indicated at 42 in FIG. 7. While the FIG. 5 device 30 suggests an open wedge-shaped design, the device 42 in FIG. 7 suggests that, between the upper and lower panels 32, 34 a pocket of biological material may be disposed. In FIG. 6, a plurality of tacks 44 are shown attached to one of the two panels of the device to be used for securing the device to surrounding tissue in the knee. The panels 32, 34 may be trimmed to the desired wedge shape.

Figure 8:
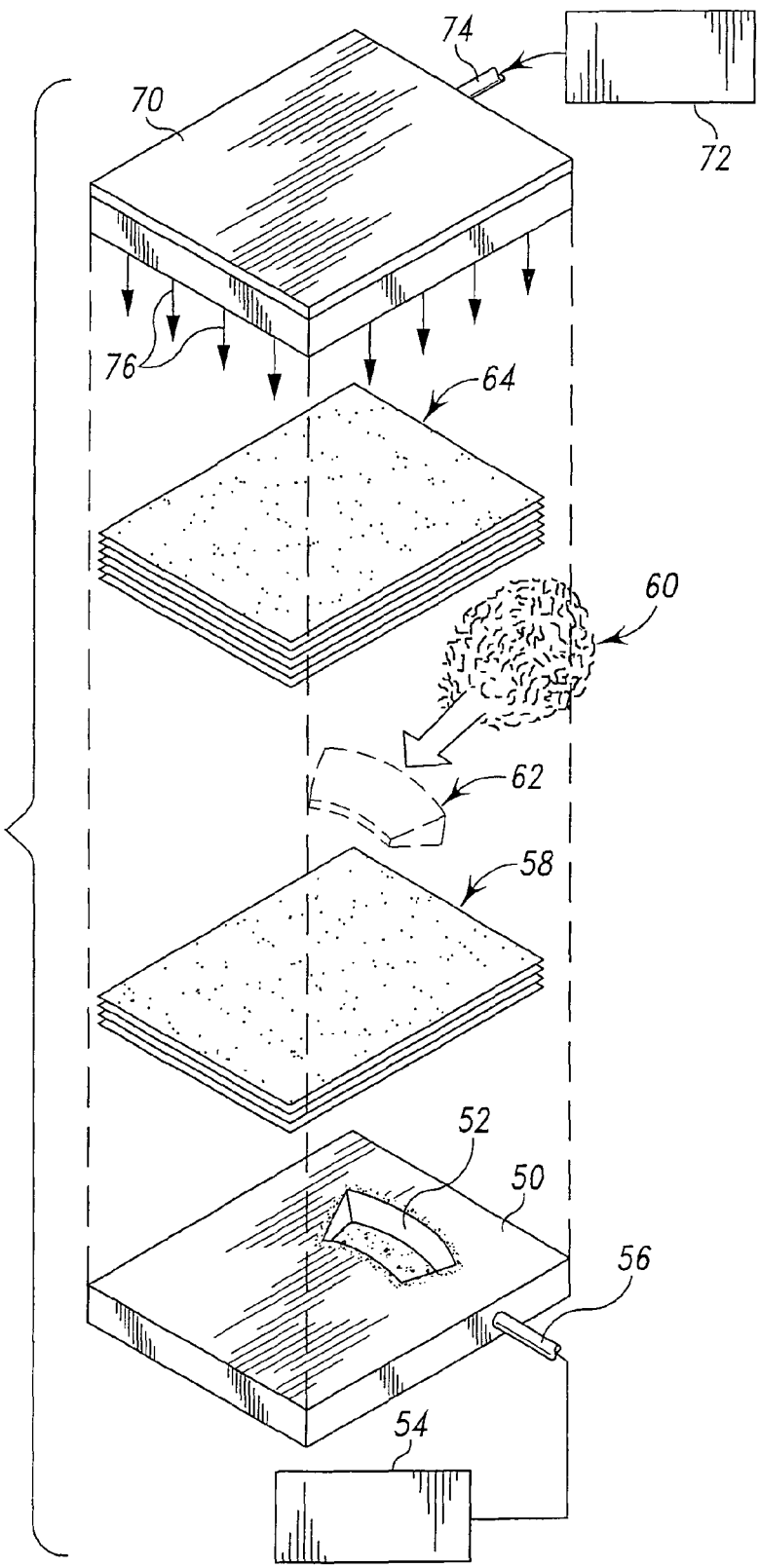
FIG. 8 shows an illustrative system and process for forming a pocket in a wedge-shaped device and filling that pocket with a biological material to promote meniscus regeneration.

FIG. 8 shows diagrammatically an illustrative system for forming devices similar to that shown in FIGS. 6 and 7, and FIGS. 9, 10, 11 and 12 show the stages of the system of FIG. 8. The illustrative FIG. 8 system comprises a vacuum plate or platen 50 having a cavity 52 in the shape of the desired device with a vacuum pump such as indicated at pump 54 connected to the cavity 52 by a tube 56. It will be appreciated that the cavity 52 is provided with a plurality of openings leading to a manifold space within the platen 50 which is connected to the pump 54. Several layers 58 of a naturally occurring ECM such as SIS are placed on the plate 50. These layers 58 which are moist and flexible are pulled by vacuum down into the cavity 52 to form a recess for receiving a mass of biological material 60 which will take the shape indicated at 62 defined by the cavity 52. Once the layers 58 are pulled into the cavity 52, and the mass 60 is placed in the shaped opening formed in the layers 58 by the cavity 52, a plurality of layers of ECM such as SIS indicated at 64 are placed over the layers 58 to enclose the mass 60 in the space defined by the cavity 52. Then, an upper platen 70 is placed over the layers 64 and 58 and clamped or otherwise held in position against the plate platen 50, to provide mechanical pressure, typically for 5-120 minutes, and more typically for 20 minutes. Vacuum from either or both of pumps 54 (via tube 56) and 72 (via tube 74), in combination with the mechanical pressure, may be used to draw moisture from the ECM material.

Subsequently, to toughen one or more of the surfaces of device 80, either or both of pumps 54 and 72 may be replaced with compressors to provide pressurized hot air to laminated layers 58 and/or 64, in combination with the mechanical pressure. The pressurized air is typically provided at room temperature to 120° C., and more typically from 30 to 70° C. Thus, it is understood that elements 54 and 72 in the drawings represent sources of vacuum and pressurized air. The combination of mechanical pressure and hot air results in toughened layers through dehydrothermal cross-linking.

As a result of toughening the ECM layers as described above, with heat and compression, the resultant toughened ECM laminate can be expected to be more dense than standard commercial ECM products. As an example, a toughened SIS laminate formed from twenty (20) layers of SIS material compressed in a vacuum bed at a temperature of 30° C. for 1 hour was determined to have a density of about $0.933+/-0.061$ g/cm$^3$. It can be expected that the density and other properties of such toughened ECM laminates can be varied with variations in processing conditions such as temperature and pressure. In comparison, the commercially available RESTORE® SIS laminate product has a density of $0.466+/-0.074$ gm/cm$^3$. A hardened SIS device as described in U.S. Provisional patent application Ser. No. 10/195,719 entitled "Devices from Naturally Occurring Biologically Derived Materials", filed concurrently herewith, can be made with a density of $0.747+/-0.059$ gm/cm$^3$, for example. An SIS foam can be made as described in U.S. patent application Ser. No. 10/195,354 entitled "Porous Extracellular Matrix Scaffold and Method", filed concurrently herewith, with a substantially lower density: $0.091+/-0.019$ gm/cm$^3$; $0.035+/-0.012$ µm/cm$^3$; or $0.006+/-0.002$ gm/cm$^3$, for example.

While the FIG. 8 illustration shows four layers 58 and six layers 64, it will be appreciated that different numbers of layers may be used. For example, a device may have from 2 to 10 layers 58 and from 5 to 20 layers 64. It will also be appreciated that different numbers of layers, different orientations of the layers, and different drying conditions may affect toughness. In one example, strips of clean, disinfected porcine SIS material as described in U.S. Pat. Nos. 4,902,508 and 4,956,178, were cut into swatches approximately 3.5" square. Several 20-layer implants were assembled from the swatches. Each swatch was oriented at 72° from the previous to obtain an isotropic laminated implant. The implants were dried under vacuum pressure in a gel drier system (Model FB-GD-45, Fisher scientific, Pittsburgh, Pa.), for approximately 2 hours at 30° C., under two different conditions. One set of implants was sandwiched between perforated stainless steel screens (20 gage thick 304 stainless steel, 15–×19" screen with 1/16" holes, 3/32" staggered centers arranged in hexagonal-close-packed format). These implants had a "dimpled" surface after drying, corresponding to the perforations on the screen. The other set of implants were dried in the same way as the first except that the porous screens were replaced by flat non-perforated surfaces. These implants had a smooth surface after drying. At least six implants of each type were fabricated. Uniaxial tension mechanical testing of implants, conducted according to ASTM standard D638, showed that the average failure stress of the smooth implants was more than two times that of the dimpled implants ($46.02+/-1.14$ MPa versus $19.97+/-1.04$ MPa.) The smooth implants were hence tougher than the dimpled implants.

Figure 9:
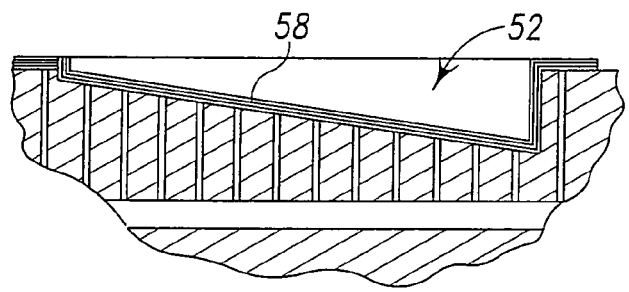
FIG. 9 is a sectional view of a portion of FIG. 8 showing how the cavity is formed in the lower panel of the wedge-shaped device.
Figure 10:
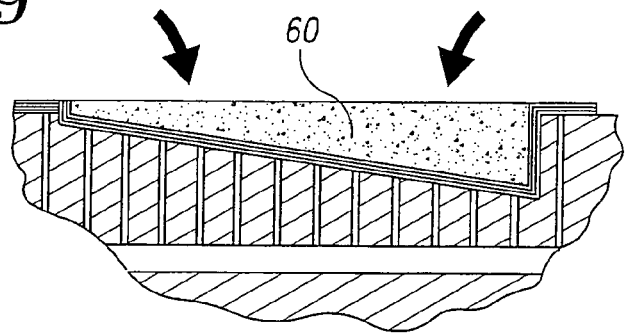
FIG. 10 shows the cavity filled with a biological material to regenerate the meniscus.
Figure 11:
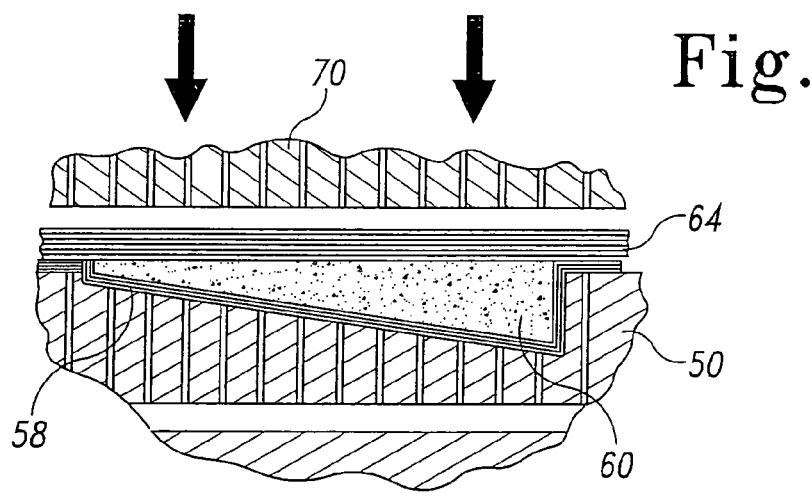
FIG. 11 shows how the upper cover for the pocket or upper panel is formed in the system illustrated in FIG. 8.

The sequence of the system of FIG. 8 is illustrated showing the layers 58 drawn down into the cavity 52 in FIG. 9. FIG. 10 shows the mass 60 located in the cavity and FIG. 11 shows the platen 70 closing against the platen 50 to capture the layers 64 above the mass 60.

As discussed above, a naturally occurring ECM for use in this invention is SIS. While SIS is commercially available, an illustrative method of obtaining SIS is as follows. Porcine SIS preferably comes from pigs raised on a Specific Pathogen Free farm. Such pigs are free from all pneumonia, diarrhea, lice, mange, and dysentery. The average pig weight is 220-280 lbs. The age of each pig should be between 150-200 days, and each pig is free from antibiotic administration for 21 days before slaughter. It is preferable that no unrefined animal byproducts be included in the pigs' diets. The SIS is obtained from the slaughterhouse by standard methods of obtaining casings. However, unless the SIS is used immediately, it is preferred that the SIS be stored in a frozen state lower than −20° C., and most preferably at −80° C. The SIS may be cleaned and disinfected by standard techniques, for example with 20% ethanol and 0.15% peracetic acid.

Figure 12:
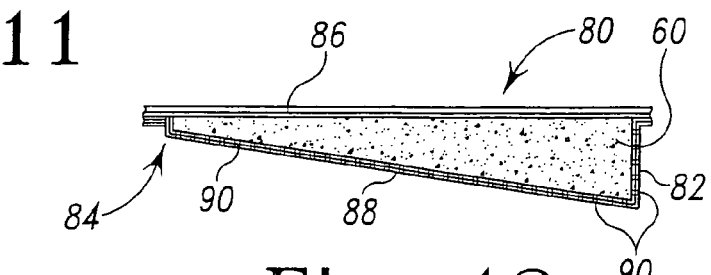
FIG. 12 is a sectional view showing the completed device made in the system shown in FIGS. 8-11.
Figure 13:
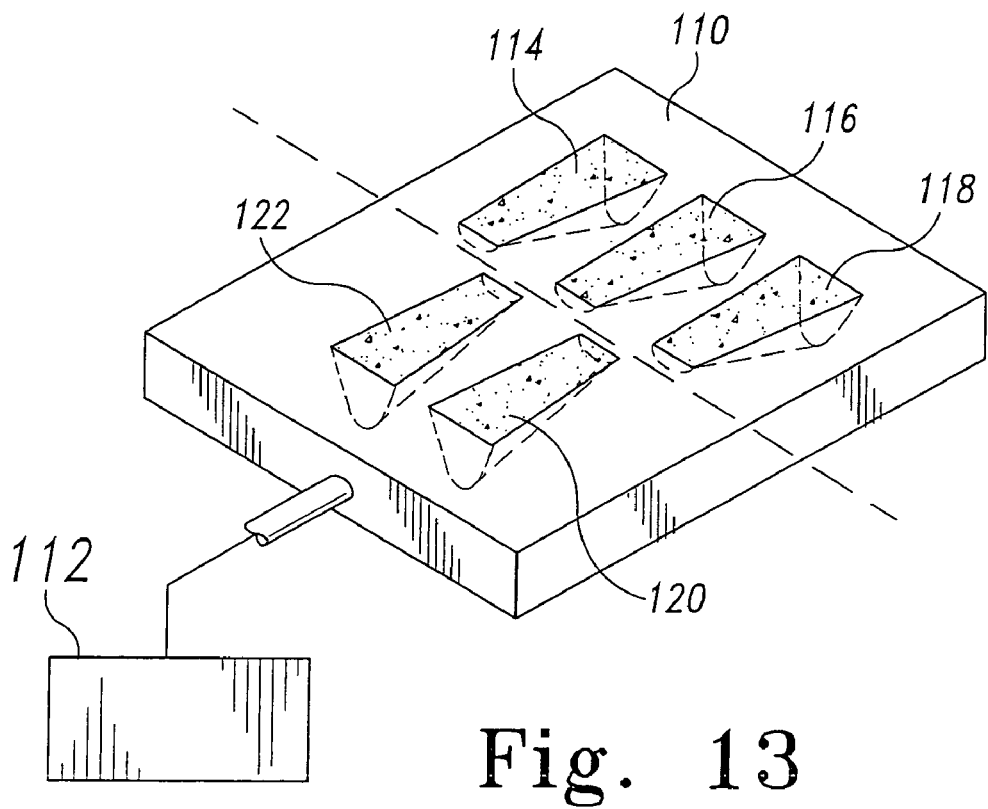
FIG. 13 shows a mechanism for forming radially extending compartments in the wedge-shaped device.

FIG. 12 shows the illustrated resulting device 80 which has a base portion 82, an apex portion 84, an upper cover 86, and a lower cover 88. The mass 60 is disposed between the covers 86, 88. Illustratively, the layers 58 and 64 may be layers or strips of SIS while the mass 60 may be a mass of comminuted SIS. In various embodiments of the device 80, and other illustrative devices hereinafter, the mass 60 may be or may comprise materials such as bioactive agents, biologically derived agents, cells, biologically compatible inorganic materials, biologically compatible polymers, and/or combinations of such materials. In a preferred method, the SIS is comminuted at 9391 rpm using a Comitrol® Processor Model 1700 with cutting head 140084-10 and a Vericut, sealed impeller from Urschel Laboratories Inc. (Valparaiso, Ind.). This method produces comminuted SIS of a consistent and reproducible size.

The device formed under pressure, compression, and heat in the system shown in FIG. 8 may be further treated in well known lyophilization processes to dry the device for shipment and/or storage. The lower surface 88 and the base portion 82 may be perforated as by penetration with a very fine cannula or other means to facilitate the hydration of the device. It will be appreciated that, when the wet layers of SIS 58, 64 and the mass 60 are dried, the body of the device, particularly the lower cover 88 and base portion 82 may shrink or cave in without the moisture. However, as illustrated, that shrinkage or caving in does not occur. The pinholes indicated at 90 expedite the hydration of the device for use by the physician.

Laminating the layers 64 under heat and pressure will provide a toughened surface to serve as a bearing surface against which a condyle will move. Ultimately, after insertion into the knee, and over a period of time, the device 80 will be remodeled to regenerate the damaged portion of the meniscus. Illustratively, subsequent to insertion, the patient will recuperate for 3-6 weeks without substantial load bearing on the knee. During this time, body fluids such as blood and synovial fluids infuse into the implant. If additional biological lubricants such as hyaluronic acid are injected into the site, such injected fluids also infuse into the implant. Other lubricants could also be used in addition to or alternatively from hyaluronic acid: lubricin, articular cartilage surface zone proteins, synovial fluid, surface-active phospholipids, and lubricating glycoprotein I, II, or any combination thereof, for example. The cells that infuse into the implant are known to proliferate in mass 60. Subsequently, when the patient resumes load bearing on the knee, it is believed that the cells begin secreting structural proteins (mostly collagens) in response to exposure to the forces of load bearing. These secreted structural proteins reform the meniscal body. It is believed that layers 64 eventually abrade away due to mechanical shearing or due to bioabsorption.

The device 80, therefore, is a composite device comprising layers of naturally occurring ECM material treated to provide a bearing surface and additional ECM material positioned below that surface to provide a framework into which regeneration of the meniscus occurs.

Figure 14:
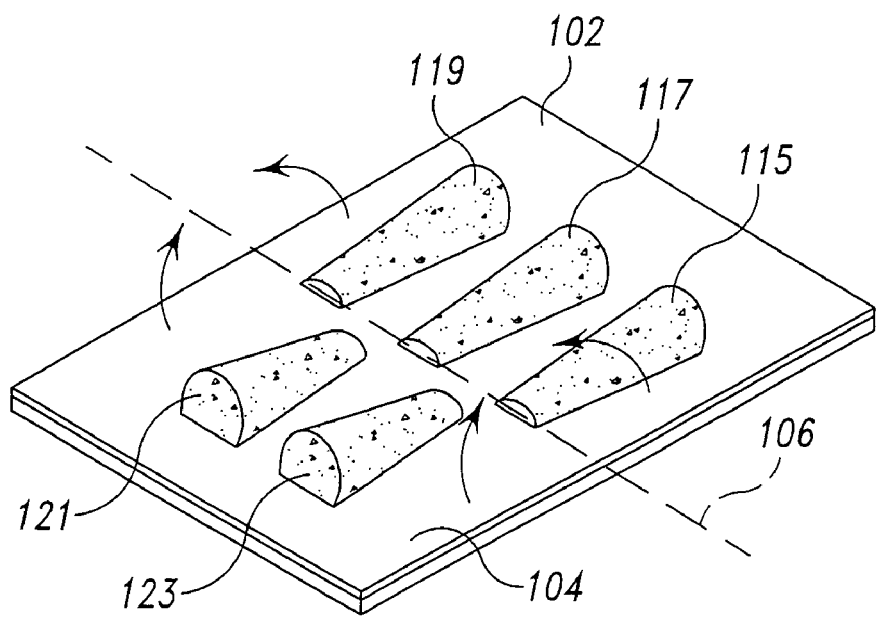
FIG. 14 shows a sheet of material formed in the FIG. 13 system with an elongated channels which will be interdigitated when the sheet is folded about a line defining the apex of the wedge.
Figure 15:
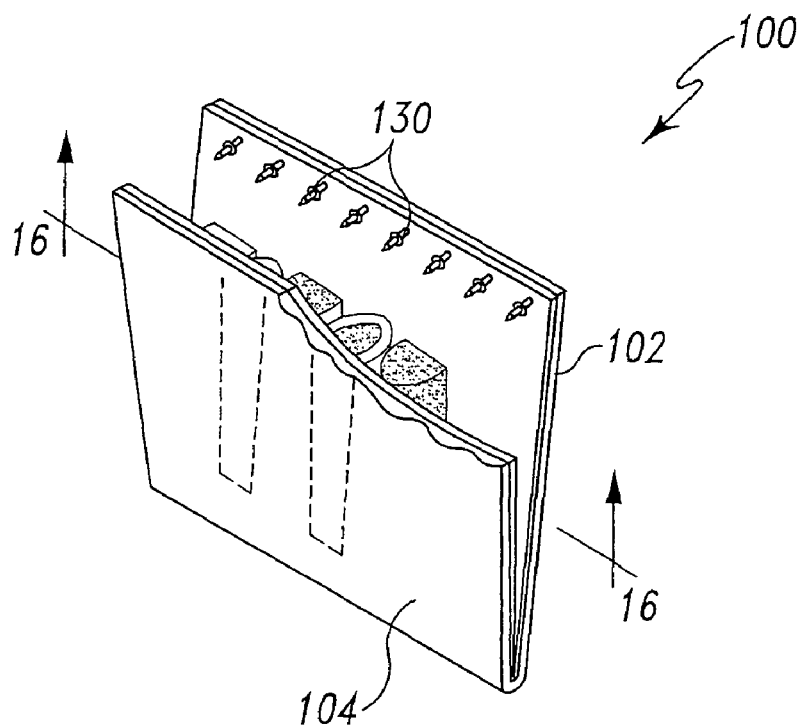
FIG. 15 shows the folding of the formed sheet from FIG. 14.
Figure 16:
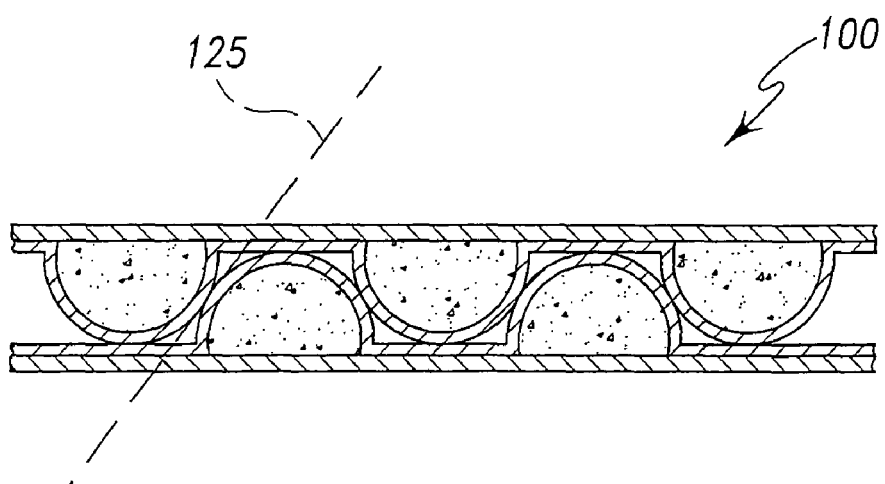
FIG. 16 shows a sectional view taken along the lines 16-16 in FIG. 15 and showing the interdigitated channels being filled with a biological material to promote meniscus regeneration.

FIGS. 13-16 show another system for fabricating a device 100 which comprises panels 102 and 104 that can be folded together about a line 106 to provide an upper cover and a lower cover with radially extending channels or compartments disposed therebetween. Illustratively, a vacuum plate or manifold 110 is provided for connecting to a pump 112 with a plurality of cavities 114, 116, 118, 120, 122 formed in the platen 110, each cavity being a radially extending, somewhat conical trough deeper and larger at its radially outer end, radially outwardly from the apex fold line 106. Wet layers of ECM strip are placed over the platen 110 and a vacuum is pulled sucking portions of the layers down into the cavities 114, 116, 118, 120, 122. Additional layers of ECM material may then be placed over the cavities. The resulting pressed and formed product is shown in FIG. 14 including the panels 102, 104 formed about a bend line 106. Each panel 102, 104 carries compartments that may be filled with comminuted ECM. Each of the three cavities 114, 116, 118 provide compartments 115, 117, 119. The cavities 120 and 122 provide the compartments 121 and 123. Since the compartments 115, 117, 119, 121, 123 are smaller adjacent the fold line 106 and larger radially outwardly from the fold line, when the two panels 102, 104 are folded together along bend line 106, the resulting product 100 will be a generally wedge-shaped device as illustrated in FIG. 15. The compartments 115, 117, 119, 121, 123 are spaced apart so that they will be interdigitated as shown best in FIG. 16 when the panels 102, 104 are folded. The upper panel (shown as 102) may be provided with tacks as indicated at 130 for attachment of the device 100 to the surrounding tissue. The compartments 115, 117, 119, 121, 123 will be generally radially extending in the device from the radially outer portion of the device as it is installed in a meniscus with the larger ends of the compartments configured to direct the regeneration radially inwardly. It will be appreciated that the compartments may be perforated and that the lower cover of the device may also be perforated to facilitate hydration of the product after it is delivered to the surgeon. The device 100 may be cut by the surgeon as indicated by the cut line 125 in FIG. 16 to make the device smaller in the circumferential direction of the meniscus.

It will be appreciated that tacks 130 may be made from well known materials that dissolve or absorb over time in the body. Such materials include, but are not limited to, PLA, PGA, a PLA-PGA copolymer, etc. In addition, as disclosed in U.S. Patent Application "Unitary Surgical Device and Method" application Ser. No. 10/483,929, filed concurrently and incorporated by reference herein, ECM can also be used for fixating elements like tacks 130.

Figure 17:
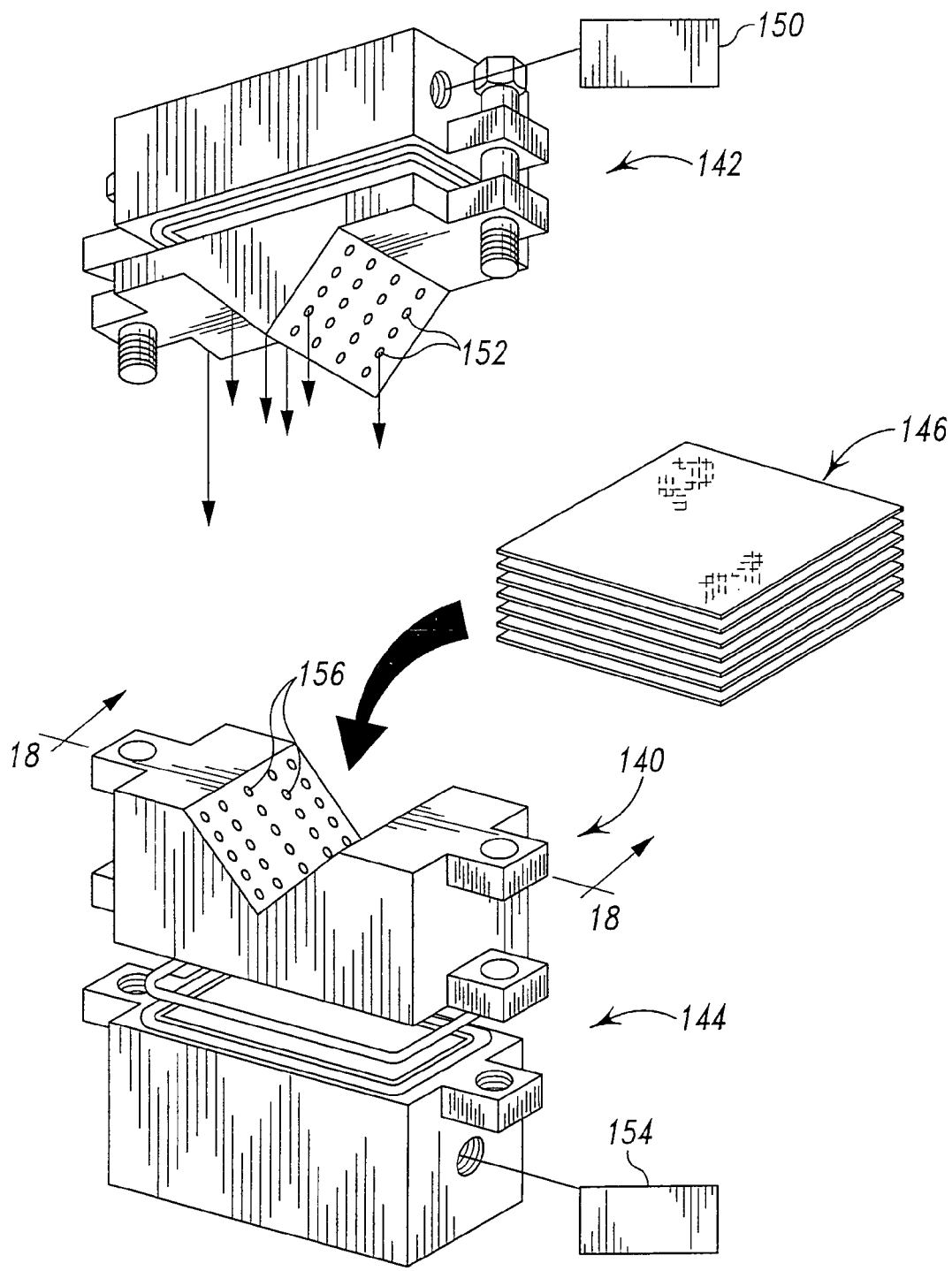
FIG. 17 shows an illustrative system for forming sheets of material such as SIS material into a wedge-shaped body.
Figure 18:
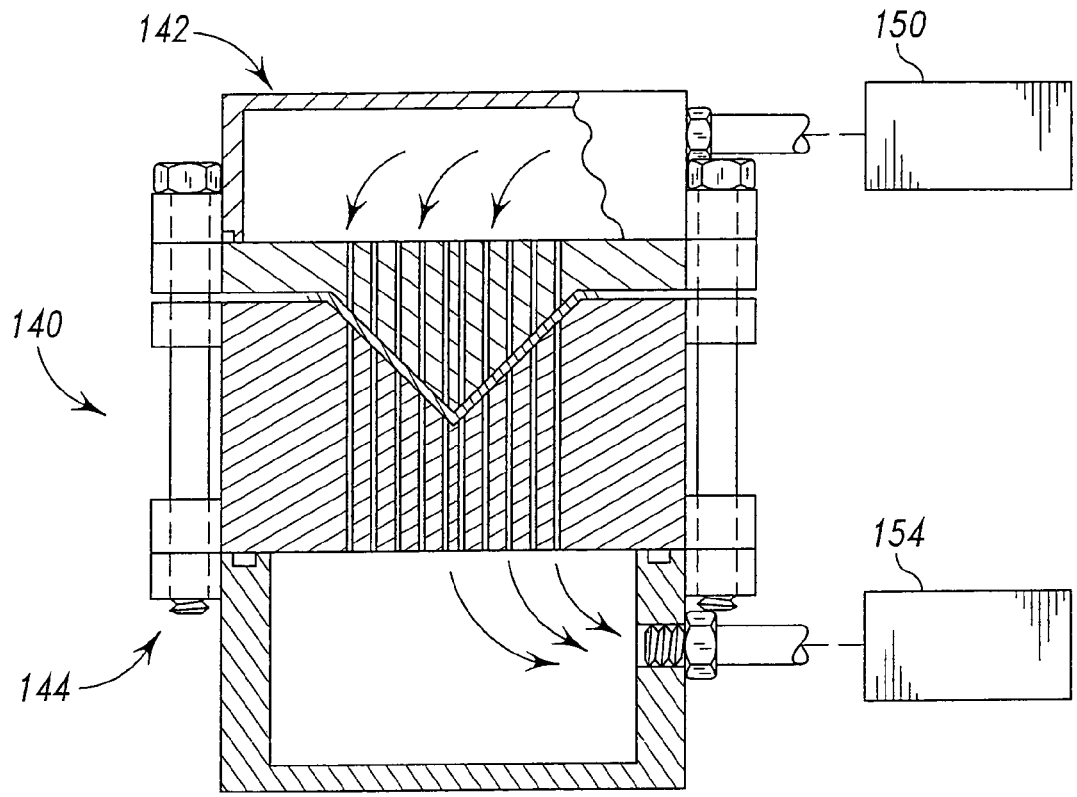
FIG. 18 shows a sectional view taken along the line 18-18 in FIG. 17 to show how the system of FIG. 17 works to form a wedge-shaped device.
Figure 19:
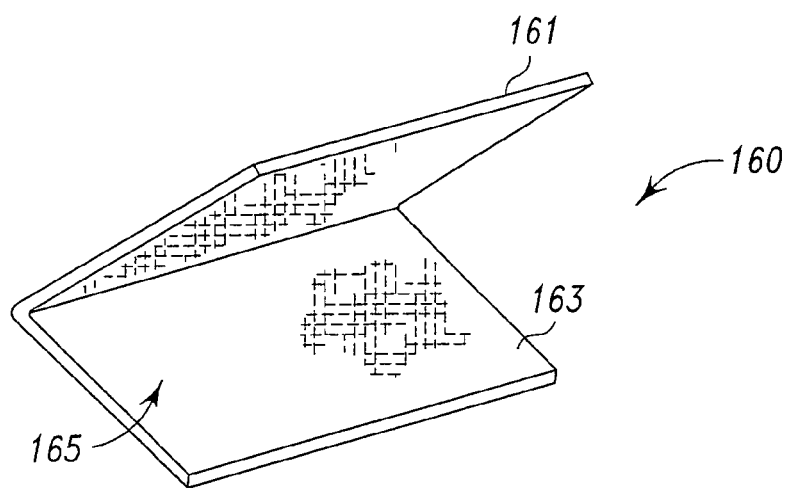
FIG. 19 shows a wedge-shaped device of the type produced by the system shown in FIG. 17 having an upper panel and a lower panel joined at an apex.

FIGS. 17, 18, and 19 show an illustrative system 140 comprising a male die system 142 and a female die system 144 for forming a plurality of layers of ECM material 146 into a desired shape. The illustrative system 140 has the male die system 142 and female die system 144 designed to produce a wedge-shape product 160. While the system 140 shown in FIGS. 17 and 18 will not be described in great detail herein, it will be seen in from the drawings that the male die system 142 and female die system 144 may be clamped or otherwise held together to provide a mechanical compression force on the layers 146. While screws are illustrated to indicate that the two systems 142, 144 may be clamped together under desired pressure simply by tightening the screws, it will be appreciated that presses of various types may be used to provide mechanical compressive forces for a plurality of layers such as indicated at 146. In addition to the mechanical compression force, the system 140 may be constructed such that either the male die system 142 or the female system 144 may be constructed to provide vacuum or heated dry air for treating the layers 146. The male die system 142 may be provided with a source 150 of compressed air or, if desired, heated compressed air forced into the male die system 142. A plurality of openings 152 are provided in the male die system for directing a plurality of streams of hot air to impinge on the layers 146 in the system 140. It will be appreciated that the male die system 142 may be reversed and that they system at 150 may be a vacuum pump if that is desired. The female die system 144 may similarly be provided with a system indicated at 154 for providing a vacuum or in the alternative, pressurized air or heated pressurized air to be expelled through openings 156 to impinge upwardly against the layers 146. While the system shown in FIGS. 17 and 18 will illustratively generate a wedge-shaped device as indicated at 160 in FIG. 19, it will be appreciated that a variety of shapes may be generated by conformingly shaping the male die and female die. For example, instead of a wedge-shaped device, the process can be used to make a toughened laminate in the form of a flat sheet.

Furthermore, the device 160 shown in FIG. 19 is a wedge-shaped device of this invention. Device 160 has upper cover 161 and lower cover 163. Upper cover is toughened, as discussed above, and is for contact with the femoral condyle. While device 160 does not have any biologic material disposed between upper cover 161 and lower cover 163, it has been shown that device 160 can be used to regenerate a damaged meniscus. Upon implantation, if the knee is sufficiently immobilized for a period of time subsequent to implantation to keep upper cover 161 and lower cover 163 apart, blood and synovial fluid will infiltrate open space 165. Later, when load bearing resumes, remodeling can occur.

Turning to the diagrammatic views FIGS. 20-24, it will be seen that an illustrative device 180 may be fabricated to have an upper cover 182 and a lower cover 184 with a plurality of circumferentially extending compartments or channels 186 within the device 180. Illustratively, the covers 182, 184 have four circumferentially extending compartments 190, 192, 194, 196, disposed therebetween. Each of these compartments may be filled with comminuted naturally occurring ECMs. Each compartment 190, 192, 194, 196 may be formed, for example, by wrapping an ECM such as SIS about a mandrel 200 (FIG. 20) to produce a single cylindrical shell (FIG. 21). FIGS. 20(a), 22(a) and 22(b) show how a plurality of channels may be formed by wrapping an elongated strip of SIS about the smallest mandrel 202 (FIG. 20(a)) and then successively the mandrels 204, 206 and 208. The resulting wrap is shown in FIG. 22(a) and the channels are shown filled in 22(b). The device 210 shown in FIGS. 22(a) and 22(b) may be covered or placed on covers such as indicated at 182, 184 as an alternative to the individual fabricated compartments 190, 192, 194, 196. Alternatively, because the final wraps extend around all of the mandrels together, the outer layers of the wraps may form the cover. As shown in FIGS. 22(a) and 22(b), a tab 205 formed as the end of the final wrap may extend beyond the base portion of device 210. Tacks, as shown in FIG. 15, may extend from tab 205, for securing device 210 to the meniscus. In preferred embodiments, the device is dried in a gel dryer vacuum bed, and all resulting SIS material becomes flattened out. Thus, it will be understood that the layers of SIS are quite thin, and FIGS. 22(a) and (b) are not drawn to scale. It is understood that device 210, formed by the process illustrated in FIGS. 22(a) and (b), is wedge-shaped with the vertical cross-section through compartment 196(a) formed by mandrel 202 being smaller and defining the apex, while the vertical cross-section through compartment 190(a) formed by mandrel 208 being larger and forming the base of the wedge shape.

Figure 24:
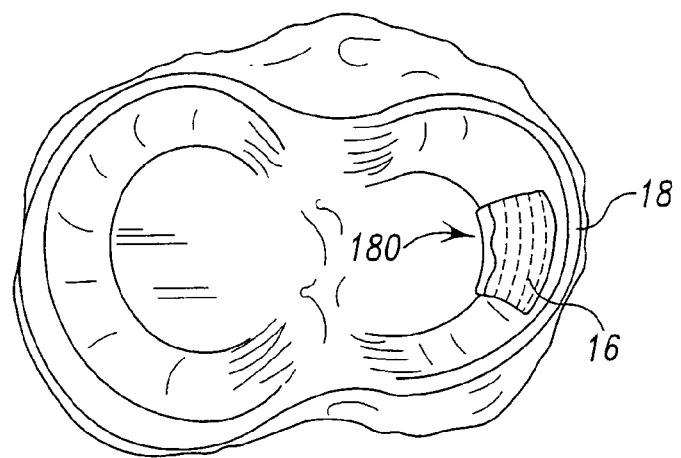
FIG. 24 shows the device of FIG. 23 installed to replace a segment of a meniscus.

The device 180 may be trimmed as indicated by the lines 220 as shown in FIG. 23 to fit into the open space 16 in the meniscus to be repaired as illustrated in FIG. 24. The channels or compartments 190, 192, 194, 196 which extend in the circumferential direction of the meniscus, provide for regeneration of the meniscus in the circumferential direction. The cylindrical shells of the compartments and the comminuted ECM material in the compartments provide the regeneration framework. The upper cover of the device 180 may be provided with attachment portions for attaching to the surrounding tissue to anchor the device.

Figure 25:
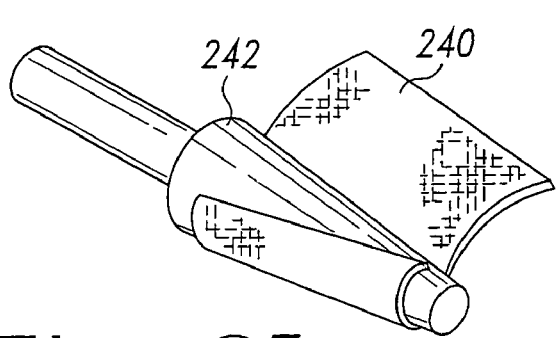
FIG. 25 shows an approach for wrapping a material such as SIS around a conical mandrel to form a single conical compartment.

FIGS. 25-31 diagrammatically show illustrative approaches for fabricating a device 230 (FIGS. 30, 31) comprising a plurality of conical compartments disposed between covers 232, 234 which may illustratively be provided by laminating sheets of ECMs. Between the upper and lower covers 232 and 234 are a plurality of radially extending conical or frusto conical compartments, each of which may illustratively be formed by a layer of ECM wrapped about a mandrel. FIG. 25 depicts a strip 240 being wrapped about a frusto conical mandrel 242 to provide a frusto conical shell 244 (FIG. 27) which may be filled as indicated at 246 with a mass of biological material to serve as a framework for meniscus regeneration.

Figure 26:
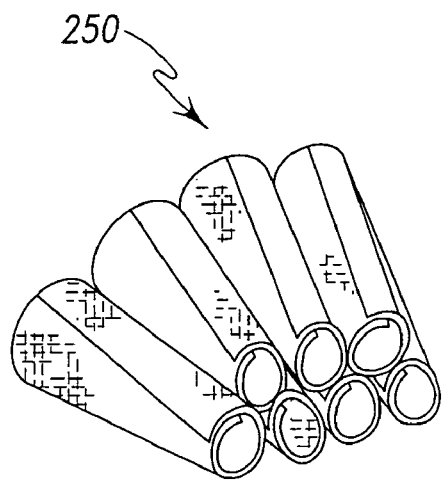
FIG. 26 shows a plurality of conical compartments assembled together.
Figure 29:
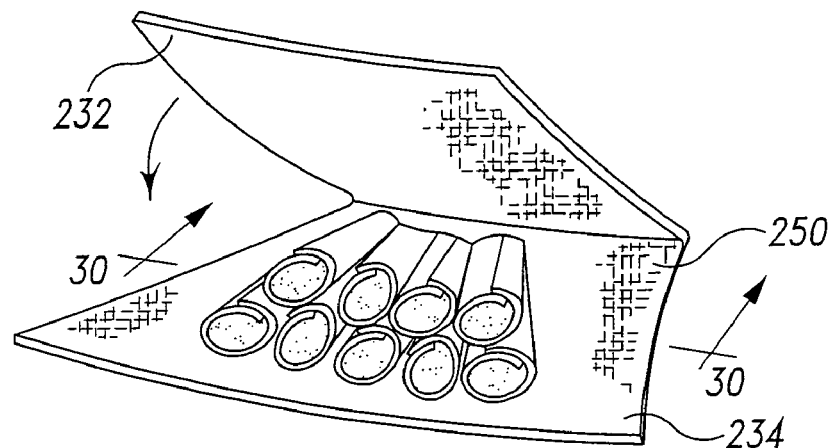
FIG. 29 shows a plurality of such conical compartments arranged together between an upper panel and a lower panel of ECM material, the compartments extending radially inwardly from the base to the apex of the wedge-shaped device formed by the plurality of conical compartments.
Figure 30:
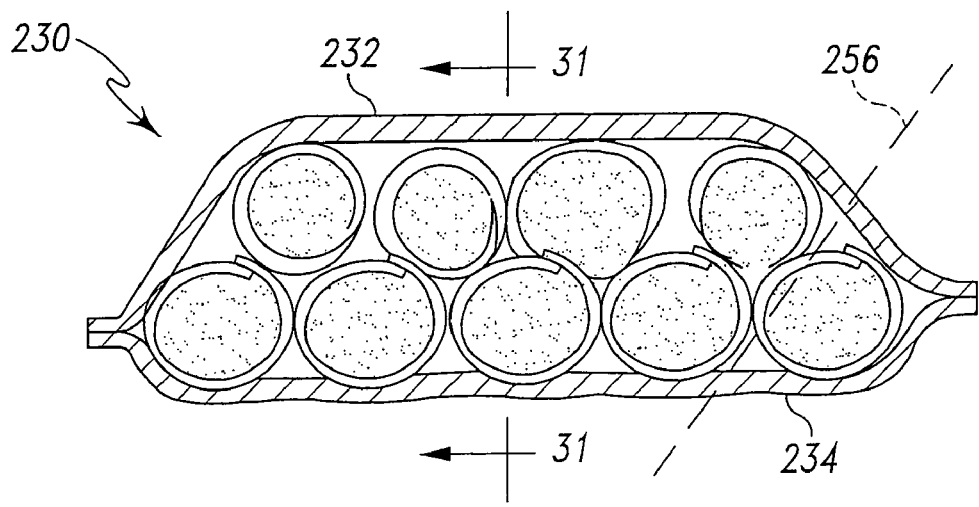
FIG. 30 shows a sectional view taken along the line 30-30 in FIG. 29.
Figure 31:
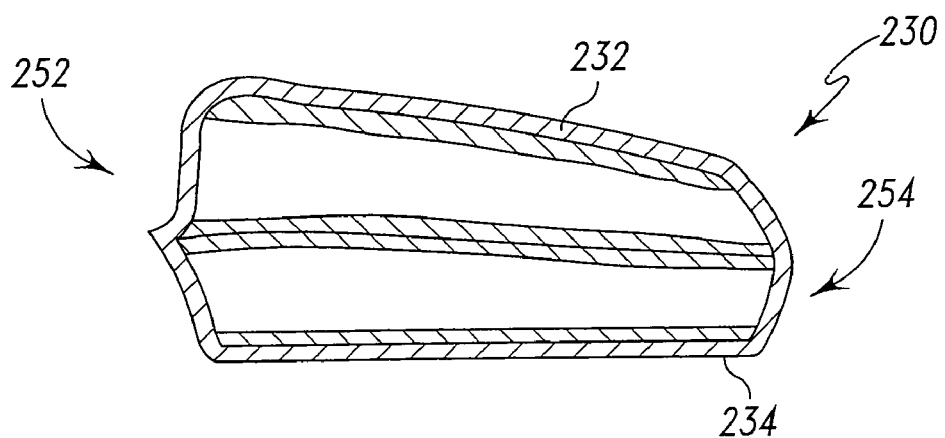
FIG. 31 shows a sectional view taken along the line of 31-31 in FIG. 30.
Figure 32:
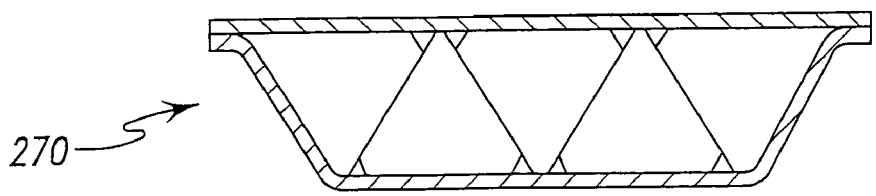
FIG. 32 shows a device containing a plurality of radially extending, generally triangular cross-section compartments.

FIG. 26 shows a plurality of such conical shells or compartments 250 which may be formed by wrapping strips of ECM such as SIS about a plurality of conical mandrels to provide an assembly to be inserted between the covers 232, 234 as depicted in FIG. 29. When the device 230 is completed as suggested in FIGS. 30 and 31, the device will have a thicker base portion 252 and a thinner apex portion 254 as indicated in FIG. 31. The circumferential extent of the device may be accomplished by trimming for example as indicated by the line 256.

Figure 22A:
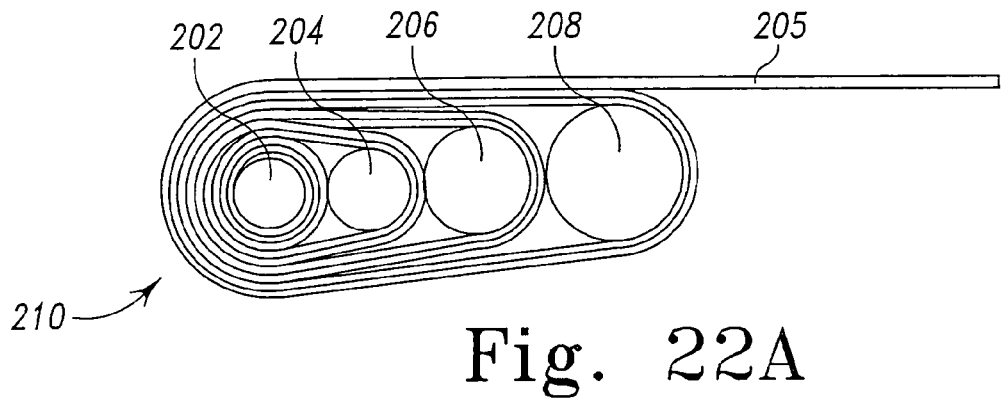
FIG. 22(a) shows an illustrative method for forming several cylindrical channels together.
Figure 22B:
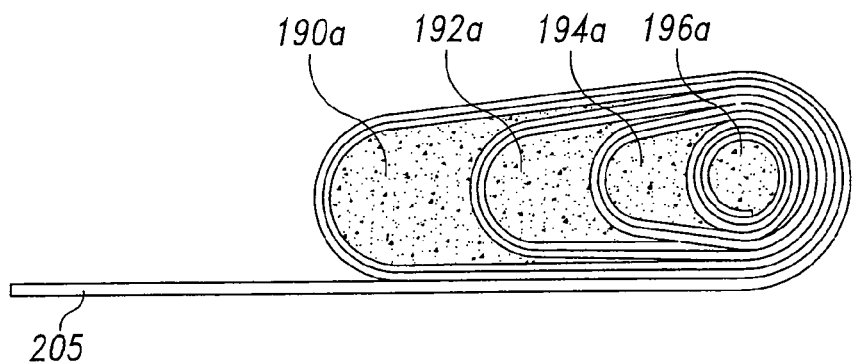
FIG. 22(b) shows the device of FIG. 22(a) filled with biological material such as comminuted SIS.

Alternatively, device 230 may be formed by wrapping successive mandrels together, similar to the method illustrated in FIGS. 22(a) and 22(b). Similar to the method shown in FIGS. 22(a) and 22(b), successive mandrels may be added until four or five compartments are formed. Alternatively, a mandrel may be wrapped with a second mandrel added to form a pair of frusto conical compartments. Two such pairs may be wrapped together to form a row of four frusto conical compartments. Subsequently, two such rows may be wrapped together to form a device similar to that depicted in FIG. 26. It is understood that the ECM layers are preferably quite thin (particularly after drying), that the number of wraps around each of the mandrels would not significantly affect the shape of device 230, and that the wedge shape of device 230 is provided by the shape of the mandrels. It is further understood that a device 230 formed by this method has at least one solid layer of ECM wrapping surrounding the plurality of frusto conical compartments, and this layer may serve as the upper and lower covers. Optionally, separate upper and lower covers 232, 234 may be added, as shown in FIG. 29.

Figure 27:
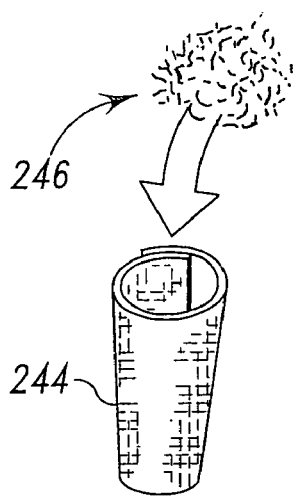
FIG. 27 shows such a conical compartment being filled with a material such as comminuted SIS.
Figure 28:
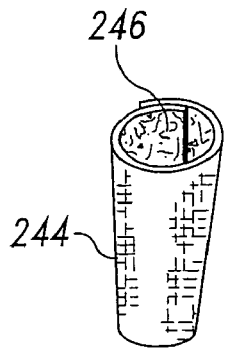
FIG. 28 shows the compartment of FIG. 27 filled with the comminuted SIS.

As shown in FIGS. 27 and 28, each of the frusto conical sections is filled with comminuted SIS 246 alone or with one or more bioactive agents, biologically-derived agents, cells or combinations thereof. The thicker base portion 252 may be sealed by upper and lower covers 232, 234, as shown in FIG. 31, or, alternatively, if device 230 is to be dried, the thicker base portion 252 may be left open after filling with comminuted SIS 256. If bioactives are added processing may be altered. For example, cells could be added to the devices in the operating room or could be cultured on sterile devices. An autograft of PRP could be added at the time of surgery. An allograft could be added in manufacturing. Any of the cavities could be filled with the biological mass during manufacture and before terminal sterilization, after terminal sterilization or in the operating room.

The device 230 may be perforated as discussed above at some point in the processing to facilitate hydration before implantation in surgery. Particularly, the lower cover and the compartments of the device may be perforated to facilitate hydration.

Figure 33:
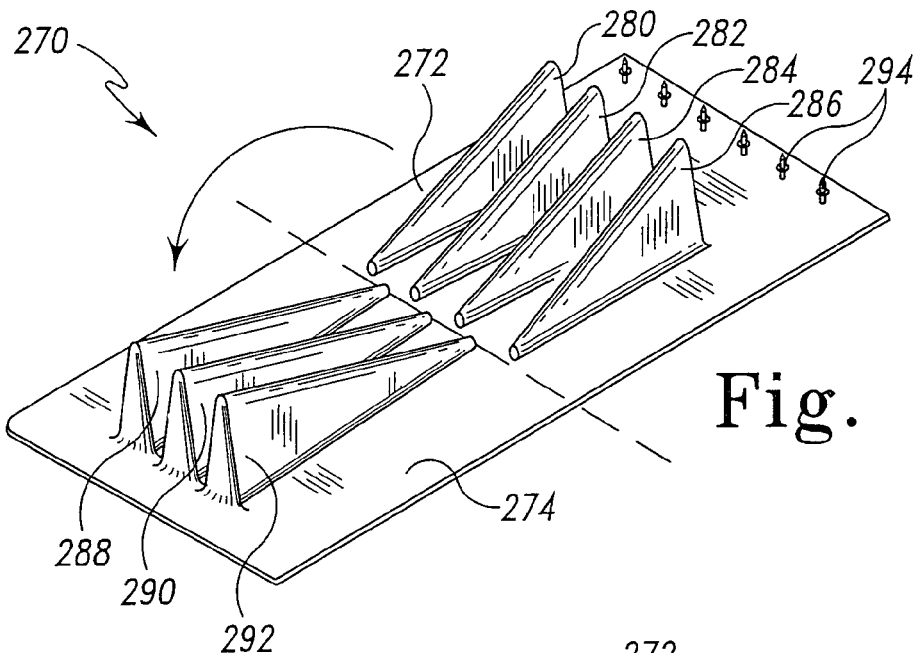
FIG. 33 shows a method for forming the device structure shown in FIG. 32, essentially a plurality of triangular recesses to be formed together.
Figure 34:
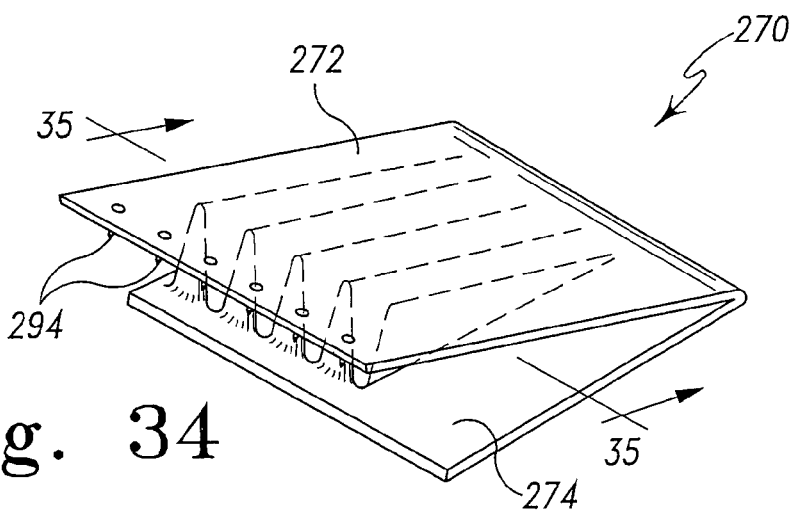
FIG. 34 shows the structure of FIG. 33 after the compartments are filled with material.
Figure 35:
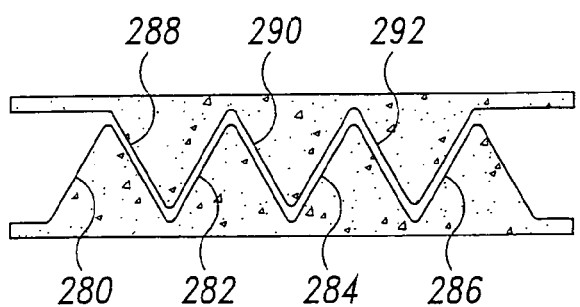
FIG. 35 shows a partial section of the FIG. 34 structure with radially extending compartments filled with comminuted SIS.

FIGS. 32-35 show a device 270 with triangular cross-section compartments between the upper cover 272 and the lower cover 274 extending radially inwardly from the base portion of the device, similar to the device 100 shown in FIGS. 13-16. The device in 270 may be trimmed to be smaller in the circumferential direction (about the meniscus) than the potential of the device in FIGS. 33-35. When the illustrative device 270 is made as depicted in FIGS. 33-35, it will have seven such triangular cross-section compartments which can be trimmed down, for example to the five compartments shown in FIG. 32. The illustrative compartments are made by vacuum drawing or otherwise forming the triangular shaped troughs or cavities 280, 282, 284, 286, 288, 290, 292 in the layers providing the upper panel 272 and the lower panel 274. The cavities may be filled with a mass of biological material such as ECM, or with combinations of ECM and bioactive agents, biologically-derived agents or cells, as discussed previously. FIG. 34 depicts the assembly of FIG. 33 folded about the apex line to provide the device 230. The upper cover 272 may be provided with tacks 294 for fixation of the device. When the device is installed in the meniscus, the radially extending compartments with their larger ends at the base portion of the device, i.e., the heavily vascularized portion of the meniscus, will serve as a framework for regeneration of the meniscus. FIG. 35 shows a cross-section of the device of FIG. 34, illustrating how cavities 280, 282, 284, and 286 interdigitate with cavities 288, 290, and 292.

FIGS. 36-39 show an illustrative device 300 (FIGS. 38 and 39) to be installed in the meniscus of the knee, the device 300 comprising panels 302 and 304 with a wedge-shaped recess 306 formed in the panel 304. The panels 302, 304 may comprise a plurality of layers of ECM material and the recess 306 may be formed by vacuum or in a forming die as discussed above. A mass of biological material is placed in the recess 306 as suggested by the arrow 310. The panel 302 is closed down over the recess 306 and the mass of biological material to provide the upper cover of the device 300.

The device 300 may be provided with attachment tacks as indicated at 312 and the lower cover of the device and the sides and base end of the device may be perforated as indicated at 314 to expedite the hydration before implantation in surgery. The surgeon may trim the device 300 along the lines indicated at 316 to provide the required fit.

Figure 63:
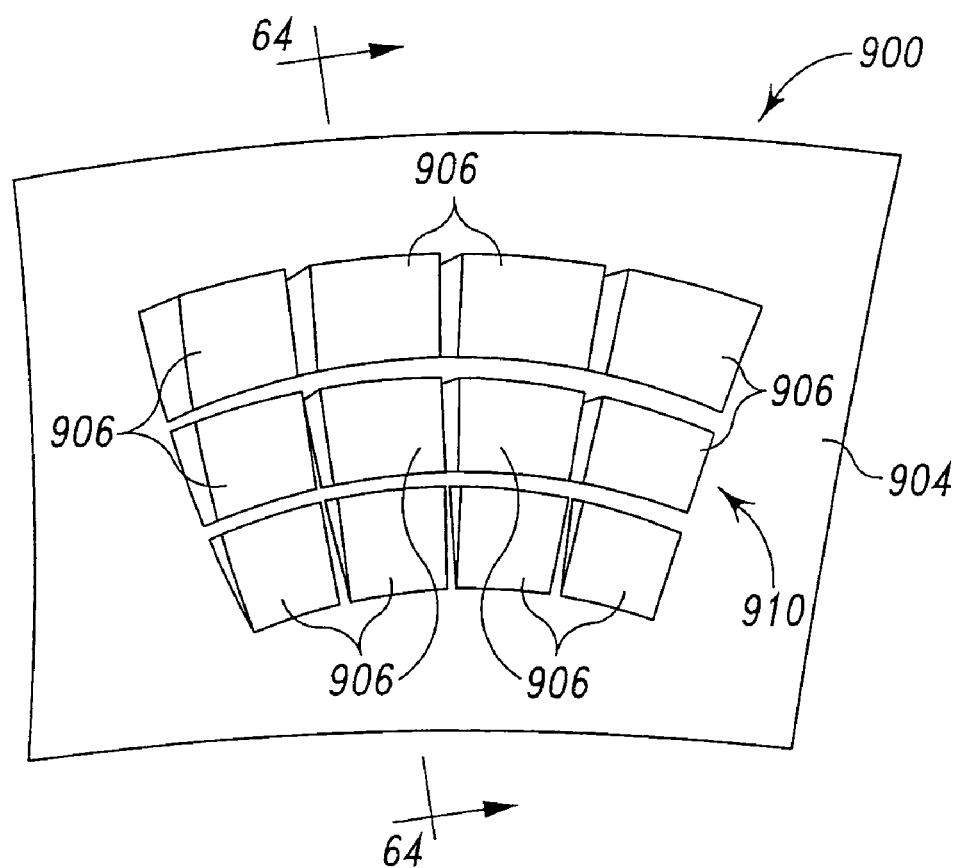
FIG. 63 is a top view of a device similar to the device shown in FIGS. 36-37 except having a segmented pillow.
Figure 64:
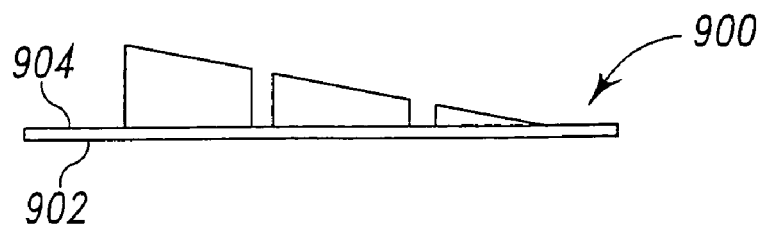
FIG. 64 is a side view of the device of FIG. 63.

FIGS. 63-64 show a device 900 similar to those shown in FIGS. 36-39, except that instead of forming a singular recess 306 in panel 304, device 900 has multiple recesses 906 formed in panel 304. As illustrated, the multiple recesses 906 are shaped and arranged to form a wedge-shaped segmented pillow 910. Each of the recesses 906 may be filled with a biological material. Upon use, a surgeon may trim segmented pillow 910 to fit a space without the release of the biological material. Thus, a single device may be provided for use with a wide variety of defect sizes.

Figure 56:
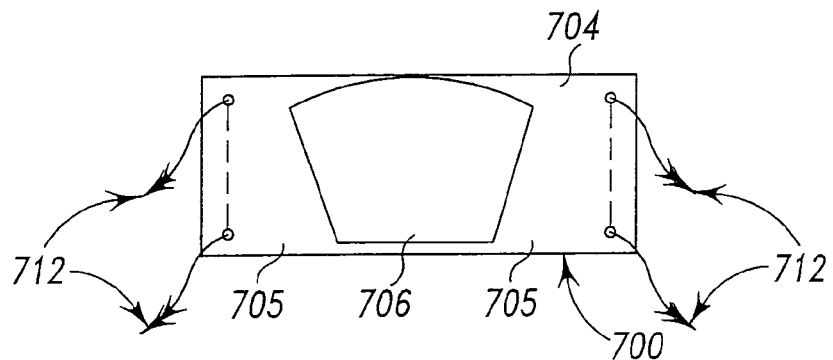
FIG. 56 is a top view of a device similar to that shown in FIG. 38, except having barbs for attachment.
Figure 57:
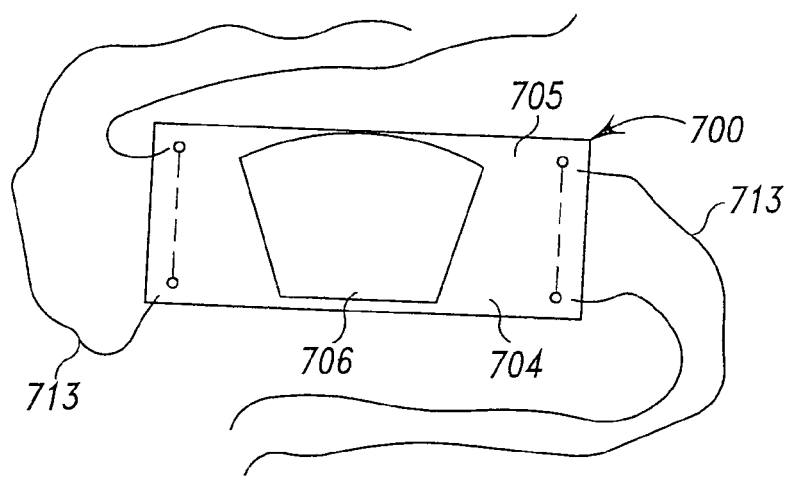
FIG. 57 is a top view of a device similar to that shown in FIG. 56, except having sutures for attachment.
Figure 58:
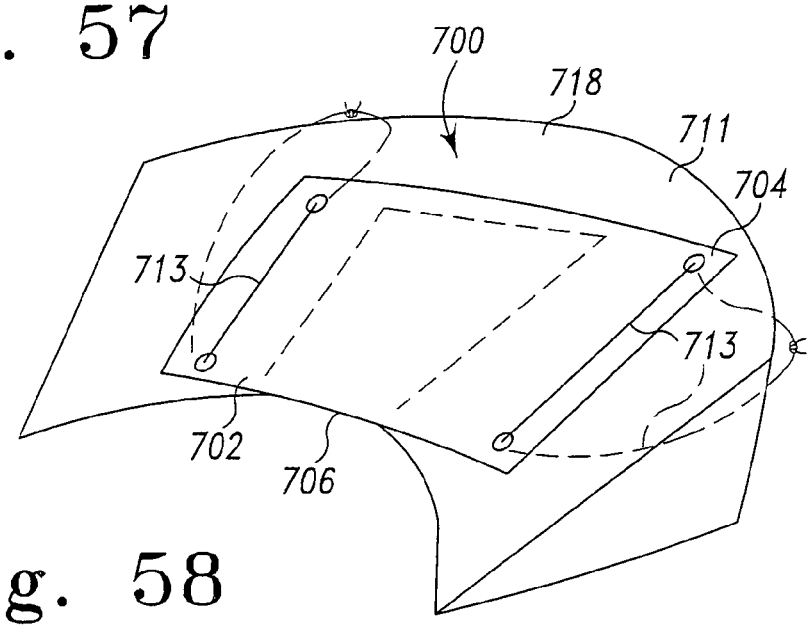
FIG. 58 is a perspective, partially cut-away view of a meniscus with the device of FIG. 56 inserted into the meniscus.

FIGS. 56-58 show devices similar to those shown in FIGS. 36-39, except that device 700 need not be wedge shaped. Device 700 comprises panels 702 and 704, with a pillow 706 of biological material shaped to fill the void in meniscus 711 left after a partial meniscectomy. The pillow is placed between panels 702 and 704. In the illustrative embodiment, pillow 706 is smaller than panels 702 and 704, and wing portions 705 of panels 702 and 704 extend beyond pillow 706. It is understood that pillow 706, as well as any of the other pillows illustrated in this disclosure may be provided as a segmented pillow, as in FIGS. 63-64.

As shown in FIG. 56, device 700 may be provided with barbed darts 712 extending from wings 705. A needle or similar device would be used to push the barbed darts 712 into or through the meniscus to secure device 700 to the meniscus. Barbed darts may be made of any biocompatable material sufficiently rigid to secure device 700 to the meniscus. Barbed darts 712 may be provided integrally with device 700 or may be added by the surgeon prior to insertion of the device.

The device illustrated in FIG. 57 is similar to the device shown in FIG. 56, except that instead of barbed darts, the device of FIG. 57 is provided with sutures 713. The device of FIG. 57 may be affixed to the meniscus in a manner similar to that of the device of FIG. 56. A needle or similar device would be used to push the sutures 713 through the meniscus. As illustrated in FIG. 58, the sutures may be tied together on the outside of the meniscus to secure device 700 in place.

While in the various embodiments discussed herein, tacks and sutures have been shown for anchoring the devices, it will be appreciated that the devices may be anchored by sutures or any other method at the choice of the surgeon. Examples of alternative methods of anchoring the devices are illustrated and described in U.S. patent application "Unitary Surgical Device and Method" application Ser. No. 10/483,929, filed contemporaneously herewith and incorporated by reference herein.

Figure 40:
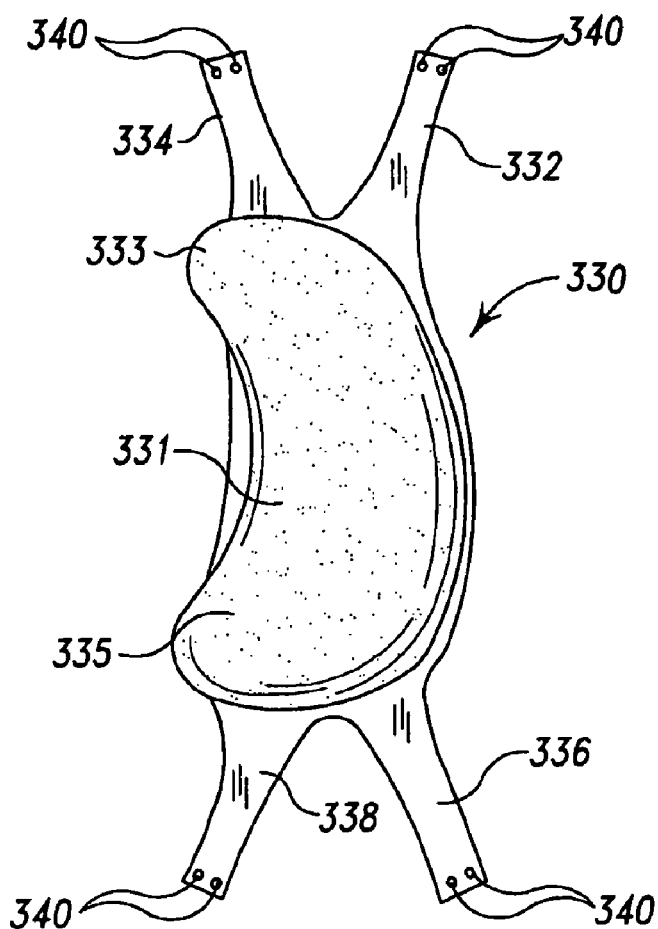
FIG. 40 shows an ECM pillow in the shape of a portion of the meniscus with the end-tabs for attaching the pillow to the surrounding tissue.
Figure 41:
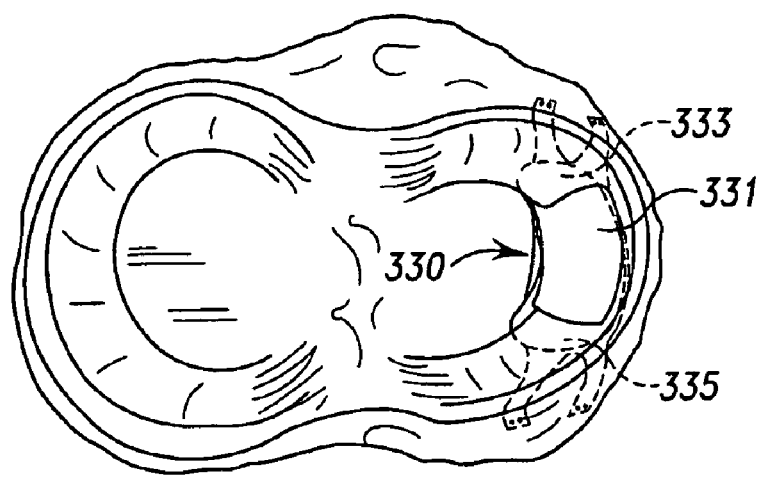
FIG. 41 shows the device of FIG. 40 attached to a meniscus.

FIGS. 40 and 41 show a device 330 which is formed in the shape of a portion of meniscus made using various techniques discussed above with at least some of the layers forming the upper surface of the device and some of the layers forming the lower surface of the device and providing extension tabs at the circumferential ends of the device. Tacks or some means for fastening the tabs to surrounding tissue may be provided at the ends of the extension tabs as indicated by reference number 340.

The central body portion of the device 330 may be a pouch or somewhat pillow-like device with a generally wedge-shaped cross-section filled with comminuted ECMs as discussed above. It is contemplated that the device 330 will be placed in the space from which a defective portion of a meniscus is excised as illustrated in FIG. 41 with ends 333 and 335 of pillow portion 331 and the tab extensions 332, 334, 336, 338 extending under remaining portions of the meniscus, with the tab extensions 332, 334, 336, 338 to be anchored to the knee as illustrated.

Figure 59:
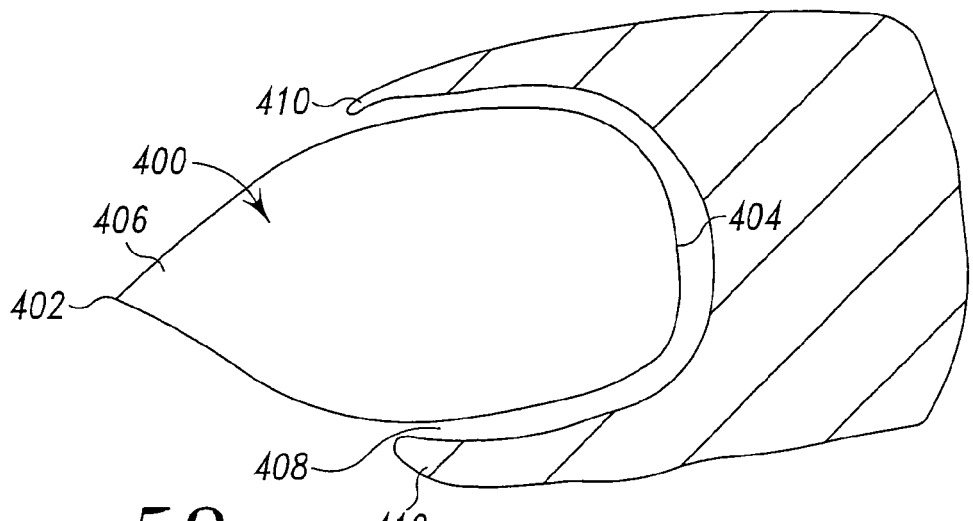
FIG. 59 shows another embodiment of a generally wedge-shaped implantable device, shown in position in a meniscus, the meniscus shown in cross-section.
Figure 60:
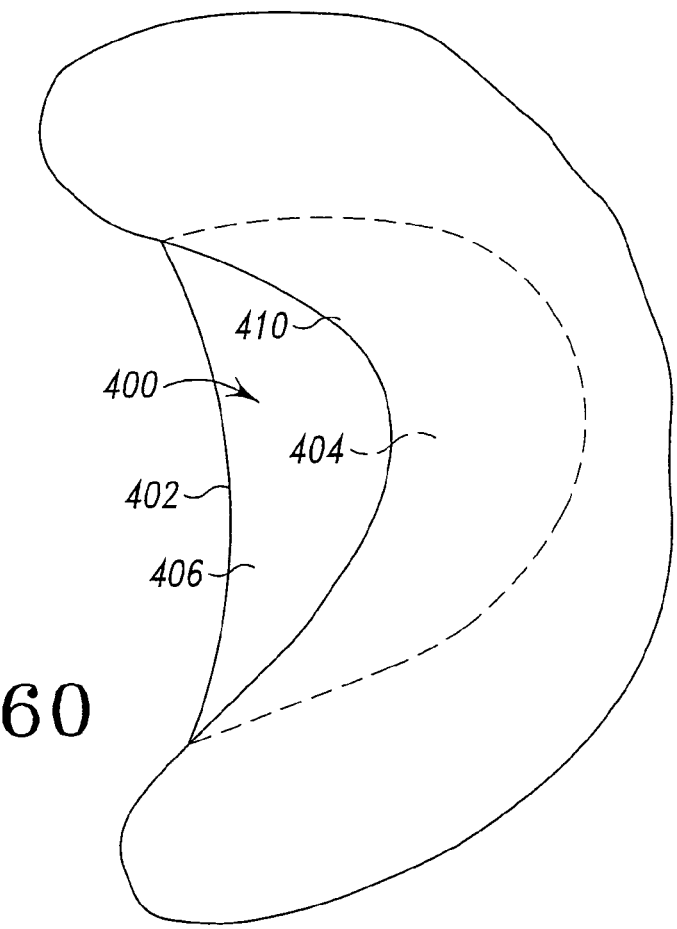
FIG. 60 is a top plan view of the embodiment of FIG. 59 in position in the meniscus.

In the embodiments illustrated in FIGS. 59-60, the device 400 is also generally wedge-shaped, being relatively thick at an outer portion 404 and tapering to an inner edge 402. In this embodiment, the inner edge 402 forms the apex of the wedge-shaped device. As can be seen from the drawings, the upper and lower surfaces of the device 400 may be curved rather than flat. In this embodiment, the process described in U.S. patent application Ser. No. 10/195,354 entitled "Porous Extracellular Matrix Scaffold and Method", referred to above, can be used to produce an ECM foam having the illustrated shape. The outer surface 406 of the foam may be toughened to form a crust-like surface or relatively hard outer shell, for example, by cross-linking the surface of the foam or by placing the shaped foam in a vacuum with heat for a short time to toughen only the outer portion. The mass of biological material remains within the crust or shell. However, it should be understood that this process is identified for purposes of illustration only, and that other processes may be employed to make the device of FIGS. 59-60. To use such a device 400, the surgeon may form a cavity in the meniscus, shown at 408 in FIG. 59, with portions 410, 412 of the meniscus left to lie over and under at least part of the device 400.

Figure 42:
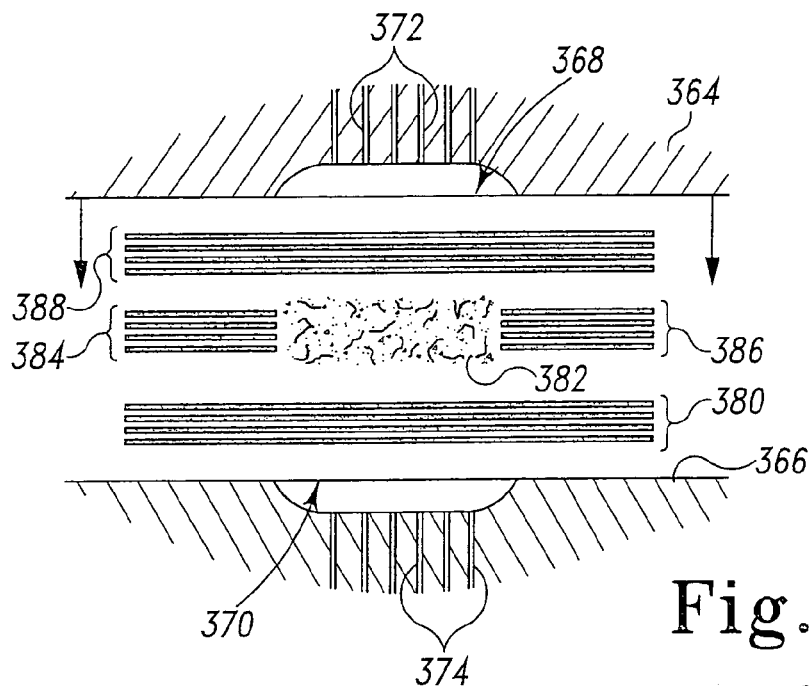
FIG. 42 shows a system for forming a multi-layered device with a central pocket or body portion containing a material such as comminuted SIS.
Figure 43:
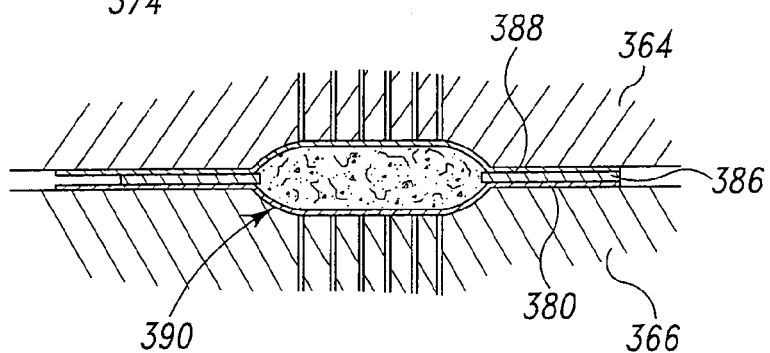
FIG. 43 shows the system of FIG. 42 closed to press the layers of material together enclosing the comminuted SIS.

FIGS. 42 and 43 show an illustrative diagrammatic system for fabricating a device 360 which is shown being installed to repair a meniscal tear in FIGS. 44, 44(a), 44(b) and 44(c).

Illustratively, the device 360 may be shaped and formed as diagrammatically illustrated in FIGS. 42 and 43. The illustrative die system comprises an upper die 364 and a lower die 366 with registering cavities 368 in the upper die and 370 in the lower die. A plurality of layers or strips of ECM material are used to fabricate the device 360. Illustratively, a plurality of layers 380 are placed over the cavity 370 as shown in FIG. 42. A mass of comminuted ECM 382 is placed in the position shown in FIG. 42 to go in the space between the die cavities 368, 370. At each end of the device, there are intermediate set of layers 384, 386. Then, an upper set of layers 388 of ECM material is provided over the layers 384, 386 and the mass 382. When the die halves 364, 366 are closed, as depicted in FIG. 43 a central body portion 390 of the device 360 is formed to have a mass of comminuted biological material surrounded by the upper layers 388 and the lower layers 380. A vacuum may be applied to the cavities 368, 370 through the lines 372, 374 or warm air may be provided through the lines. Once the device is formed as shown in FIG. 43, the central body portion 390 has extension portions 392, 394 formed by pressing the layers 380, 384, 386, 388 together. Either extension portion 392, 394 may be used by the surgeon to pull the device 360 into a tear such as indicated at 393 at FIGS. 44, 44(a), 44(b), 44(c). Essentially, a surgeon may use one of the extensions, such as extension 392, to pull the central body portion 390 downwardly into the tear 393 by extending the end of the extension 392 into the tear and then radially inwardly under the inner most edge of the meniscus. It will be appreciated that some surgeons may prefer to pull the extension 394 radially outwardly under the outer edge of the meniscus.

Figure 44:
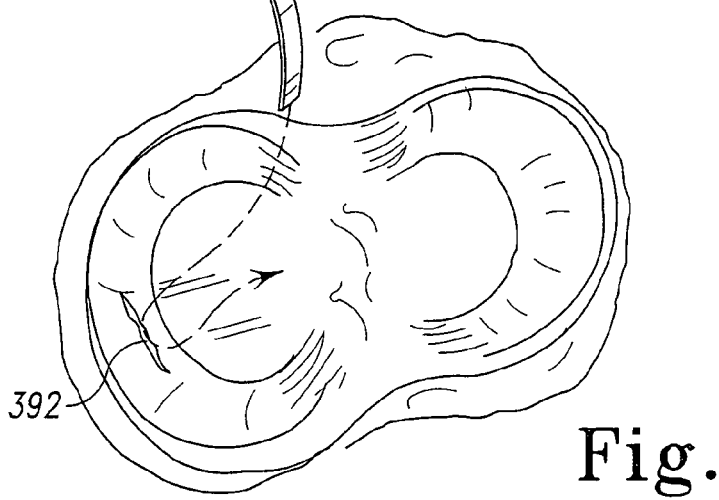
FIG. 44 shows how the device of FIGS. 42 and 43 may be installed into a meniscus.
Figure 44A:
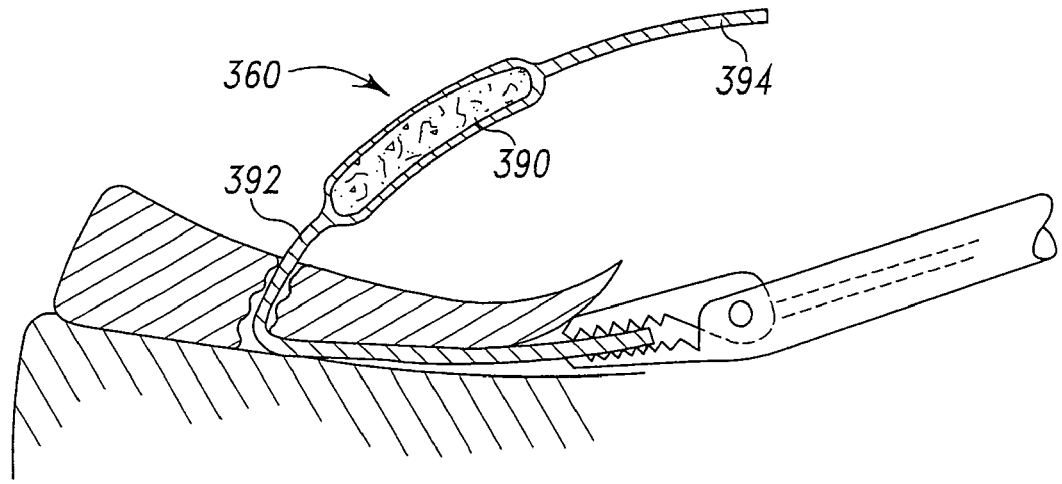
FIGS. 44(a) (b) and (c) show the process started in FIG. 44.
Figure 44B:
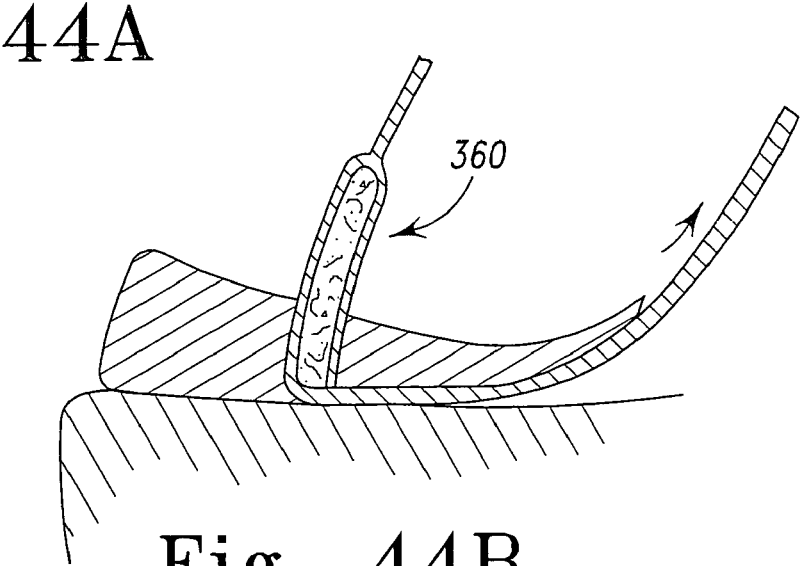
Figure 44C:
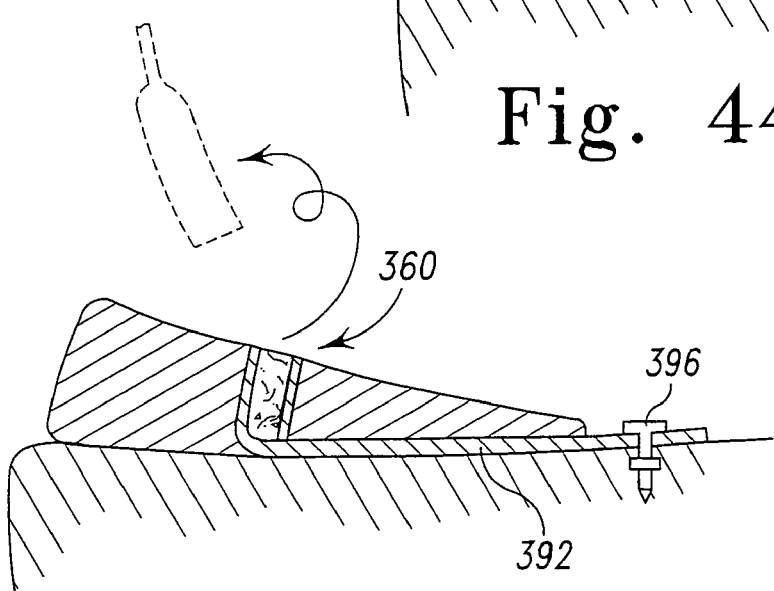

FIGS. 44(a), 44(b) and 44(c) show the progression of the insertion of the device 360 into the tear 393. A surgeon may cut away a portion of the device 360 which extends above the upper surface of the meniscus as suggested in FIG. 44(c). Also, the surgeon may use a tack 396 to hold the distal end of the extension 392 in place as suggested in FIG. 44(c).

Figure 45:
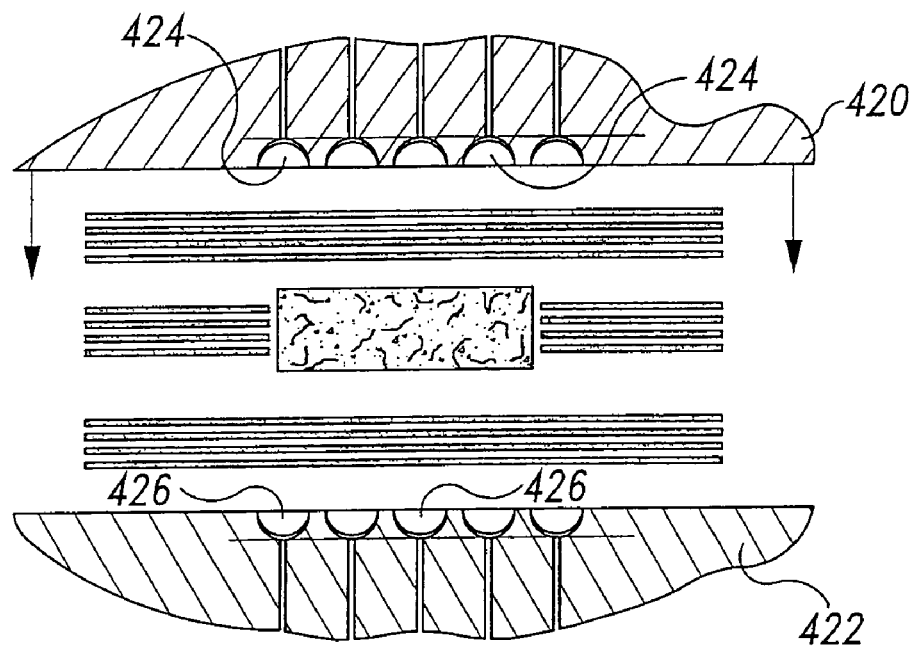
FIG. 45 shows a forming press similar to that of FIGS. 42 and 43 except that there are a plurality of pockets of comminuted SIS separated from each other so that the device can be trimmed between the pockets.
Figure 46:
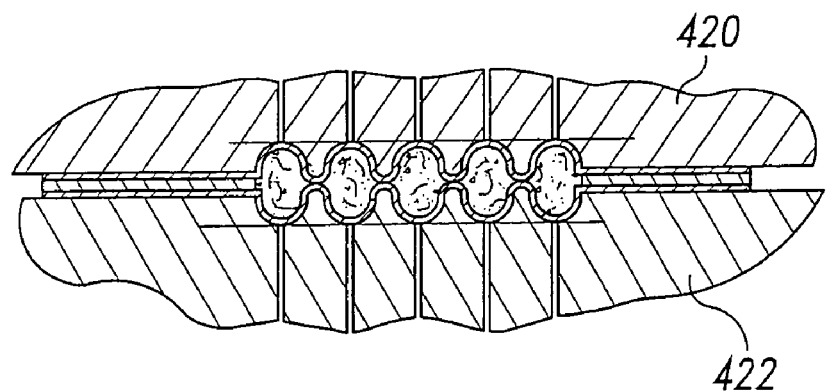
FIG. 46 shows the press of FIG. 45 closed.
Figure 47:
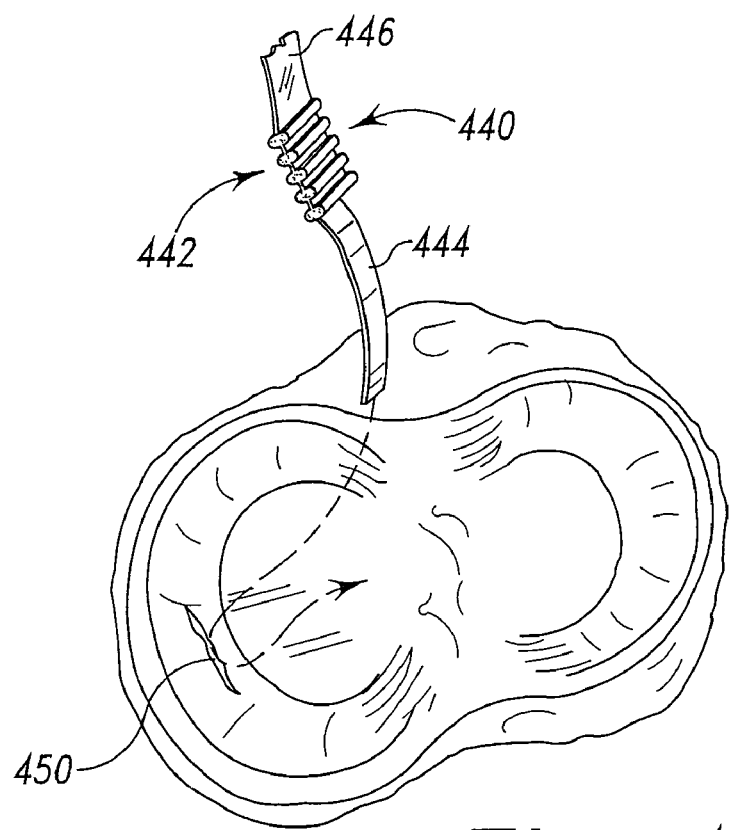
FIG. 47 shows how the device resulting from FIGS. 45 and 46 may be installed on a tibial platform.
Figure 47A:
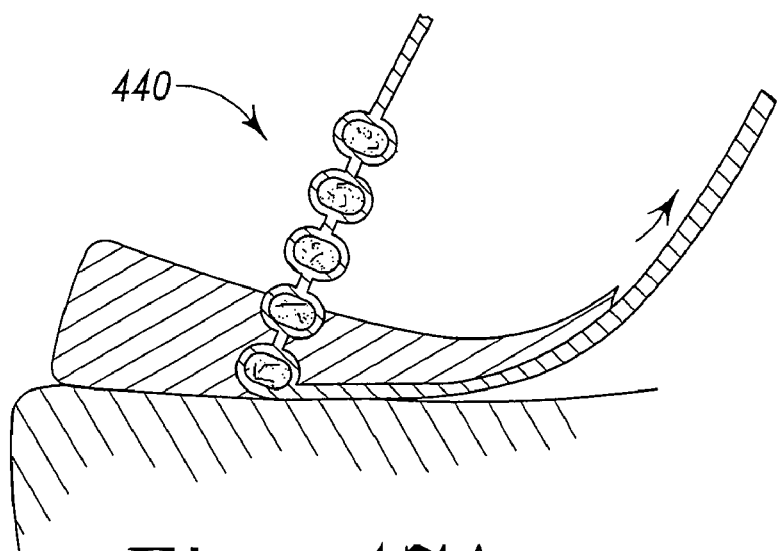
FIG. 47a shows a further step in the process started in FIG. 47.

FIGS. 45 and 46 show an illustrative system similar to that shown in FIGS. 42 and 43 for forming a device except that the central body portion of the device may be divided into spaced apart compartments to provide separation points for trimming by the surgeon. In FIGS. 45 and 46, an upper die 420 and a lower die 422 are provided with a plurality of spaced apart cavities 424 in the upper die and 426 in the lower die. These cavities 424 and 426 are spaced apart so that when the dies 420 and 422 are brought together, they provide five spaced apart compartments, each containing a mass of comminuted ECM on an ECM strip. The resulting device 440 includes a central body portion 442 comprising a plurality of spaced apart compartments with extensions 444, 446 for handling the device 440. The device 440 is pulled into the tear 450 to extend along the tear and to fill the tear as discussed above. The device of 440 is similar to the device 360 except that the surgeon may cut the device as depicted in FIG. 47(a) between adjacent compartments.

It should be appreciated that in the embodiments illustrated in FIGS. 42-47, the layers 380, 384, 386, 388 of ECM material are not exposed to shear forces from the femoral condyles when implanted to repair a tear in the meniscus. In these embodiments, the ECM layers need not be toughened, although they should have sufficient tensile strength to allow the extension portions 392, 394 to be pulled or otherwise positioned between the faces of the meniscal tear as illustrated in FIGS. 44a-44b to the position shown in FIG. 44c.

Figure 48:
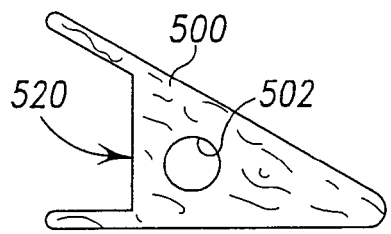
FIG. 48 shows a side view of one of a plurality of ECM members which may be assembled together to fill and repair a cut-out opening in a meniscus.
Figure 49:
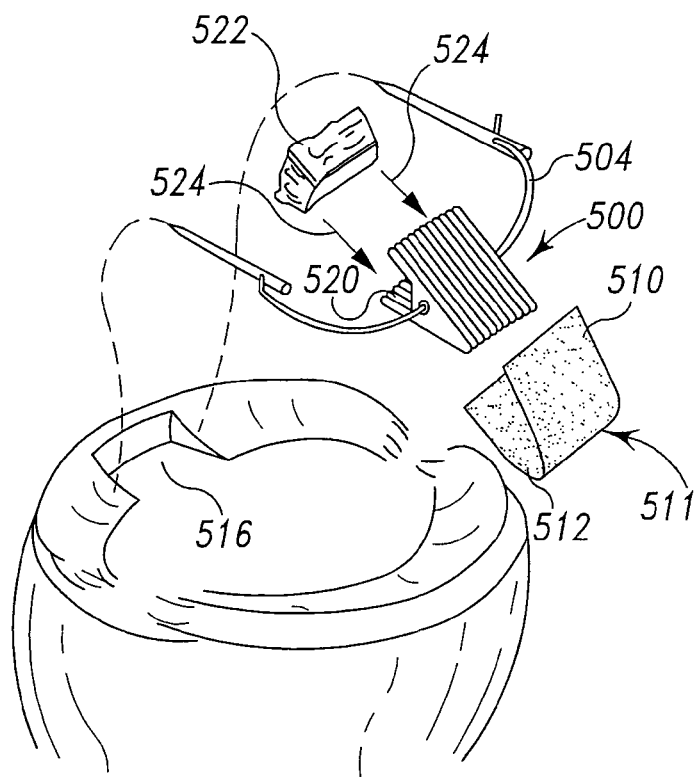
FIG. 49 shows a plurality of members of FIG. 48 arranged and held together for insertion into a cut-out portion of the meniscus.
Figure 50:
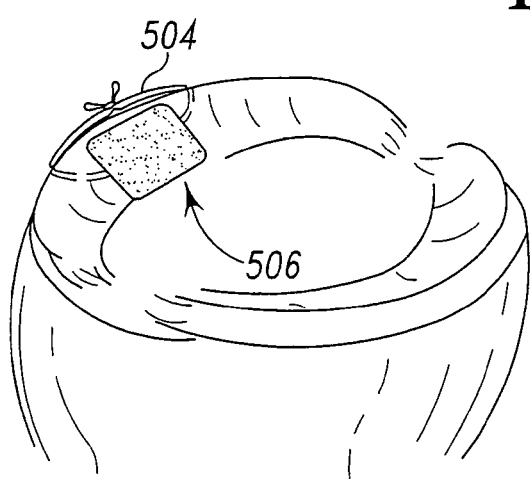
FIG. 50 shows the assembly of FIG. 49 held in place in the meniscus with a suture strand.
Figure 51:
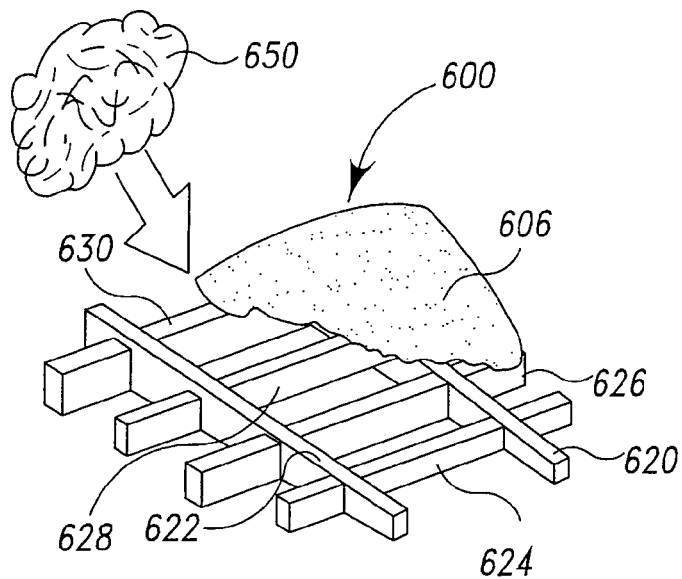
FIG. 51 is a perspective view of a framework structure made by hardened and toughened ECM members to form a lattice which defines spaces to be filled by ECM and which may be covered by ECM.

Referring to FIGS. 48, 49 and 50, it will be seen that the plurality of wafer-like members 500 may be assembled together to provide a wedge-shaped assembly. These members 500 provide a support structure for a wedge-shaped meniscus repair or regeneration device. Each member 500 is formed from a process wherein layers of the naturally occurring ECM material are laminated together, illustratively by curing by air drying, to form a rigid plate-like body. Then, the individual wafer-like members are cut into a wedge shape, for example by a laser machine unit that is programmed to cut the pattern. It has been found that such laser cutting of laminated ECM will fuse the edges together for enhanced structural support. Thus, each member 500 is generally wedge shaped, corresponding to a meniscus section removed from a natural meniscus in a plane extending radially outwardly and axially along the tibia axis, the plurality of members 500 being disposed in a side-by-side relationship about the circumference of the meniscus. It will be appreciated that the illustrative wafer-like members 500 are provided with openings 502 through which a suture 504 may extend to hold the members 500 in position as illustrated in FIGS. 49 and 50. The plurality of members 500 further may be placed in a shell 511 providing an upper panel 510 and a lower panel 512 angularly spaced to define an apex portion and a base portion. The members 500, when assembled together and secured by the suture 504, will provide a support structure between the upper panel 510 and a lower panel 512. It will be appreciated that the upper panel 510 and lower panel 512 may be provided by wrapping a laminate of naturally occurring ECM about the assembly of members 500 such that the upper edge of each member 500 provides a support for the upper panel and the lower edge of the member 500 rests on the lower panel. Such a cover 511 is shown having an upper panel 510 and a lower panel 512 in FIG. 49. Each member 500 is shown having an opening 520 at its base portion (facing radially outwardly in the knee) such that when the plurality of members 500 are assembled together, the openings 520 are aligned to provide a space into which a conformingly-shaped wedge 522 of biological material may be inserted as indicated by the arrows 524 in FIG. 49. This wedge 522 may include naturally occurring ECM to promote regeneration of the meniscus.

Thus, with the assembly of members 500 gathered together on the sutures 504 and inserted into the cover (panels 510, 512) and filled with the material 522, the device 506 may be inserted into an opening 516 cut into the meniscus and held to the meniscus with the suture 504 as suggested in FIG. 50. While each member 500 may shift slightly relative to the adjacent members 500, the device 506 provides sufficient support for weight bearing of the femoral condyles on the meniscal surface. Alternatively, the members may be secured to each other using the openings 502, and the upper or lower panels may be provided with tacks, such as shown in FIG. 38, to secure the device to the remaining portions of the meniscus.

Figure 52:
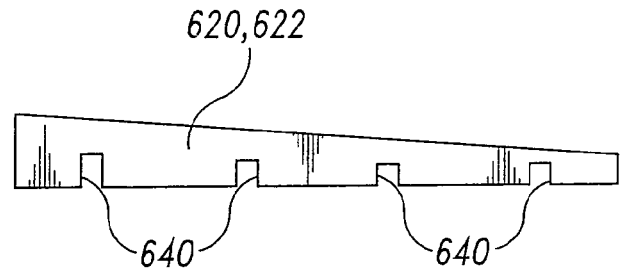
FIG. 52 shows a member of the lattice structure of FIG. 51.
Figure 53:
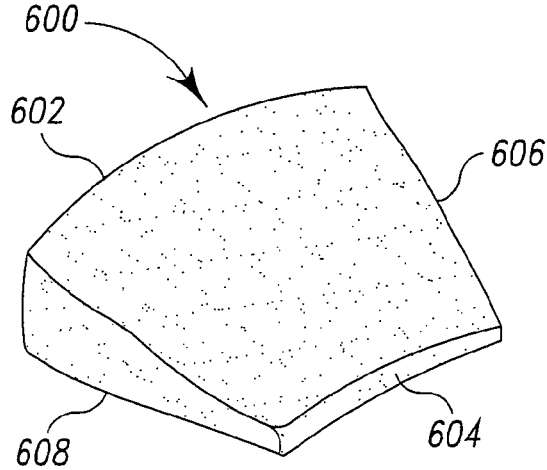
FIG. 53 shows the device of FIG. 51 after being covered with ECM material.
Figure 54:
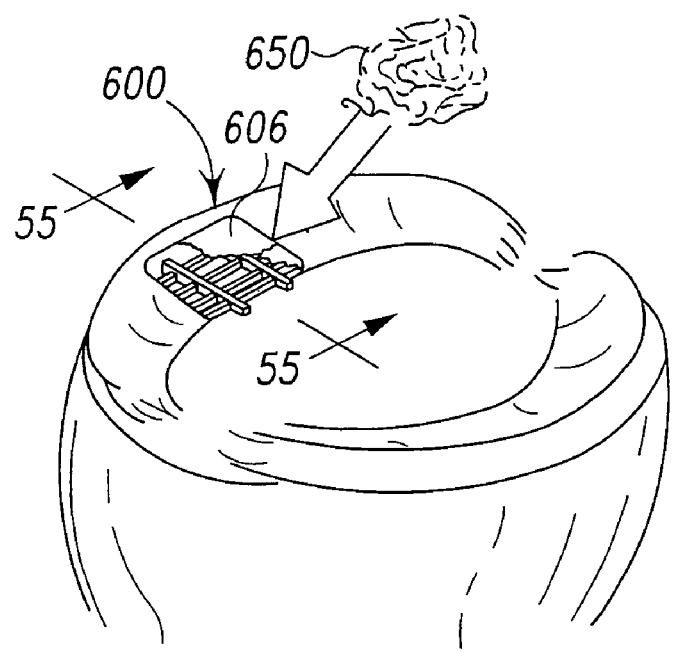
FIG. 54 shows a view of the device of FIGS. 51 and 53 inserted into the meniscus.
Figure 55:
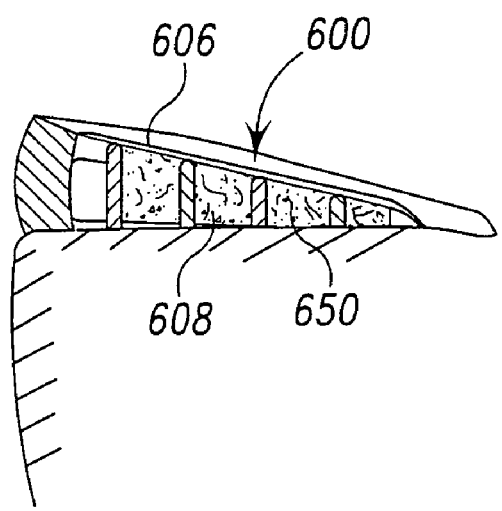
FIG. 55 shows a sectional view taken along the lines of 55-55 in FIG. 54.

FIGS. 51-55 show an implant device 600 for regenerating a portion of a meniscus in a knee. The illustrative device 600 has a radially outer portion 602, a radially inner portion 604, and upper surface 606 and a lower surface 608. Preferably, the radially outer and inner portions will be curved to conform to the outer and inner portions, respectively, of the portion of the meniscus to be regenerated. While the device shown in FIGS. 48-50 has a plurality of wafer-like members 500 to provide a support structure, the device 600 in FIGS. 51-55 has a support structure disposed in the space provided between the upper surface 606 and the lower surface 608, the support structure comprising a plurality of structure members of naturally occurring ECM cured to be rigid and hardened. Illustratively, the device 600 comprises a plurality of interlocking members 620 and 622 extending radially and members 624, 626, 628 and 630 extending circumferentially. These members may be interlocked, for example, by providing interlocking notches, as shown in FIG. 52. Illustratively, each of the radial structural members 620, 622 is provided with notches 640 for receiving the circumferential members 624, 626, 628, 630. It will be appreciated that each of the circumferential members 624, 626, 628, 630 is similarly provided with upwardly open notches for receiving the radial members 620, 622. Thus, the assembled structural members form a lattice defining open spaces. These structure members are formed from hardened and rigid naturally occurring ECM to provide a structure to support the weight on the meniscus being repaired. The lattice of members provide opening spaces in which a material 650 may be placed to promote the regeneration of the meniscus. Material 650 may comprise, for example, comminuted SIS, an SIS foam, fibrin, platelet rich plasma, blood clot, or combinations thereof. The device 600, with its wedge shape will be inserted into a correspondingly shaped cut-out in the meniscus and anchored in the meniscus to support the regeneration thereof.

Figure 61:
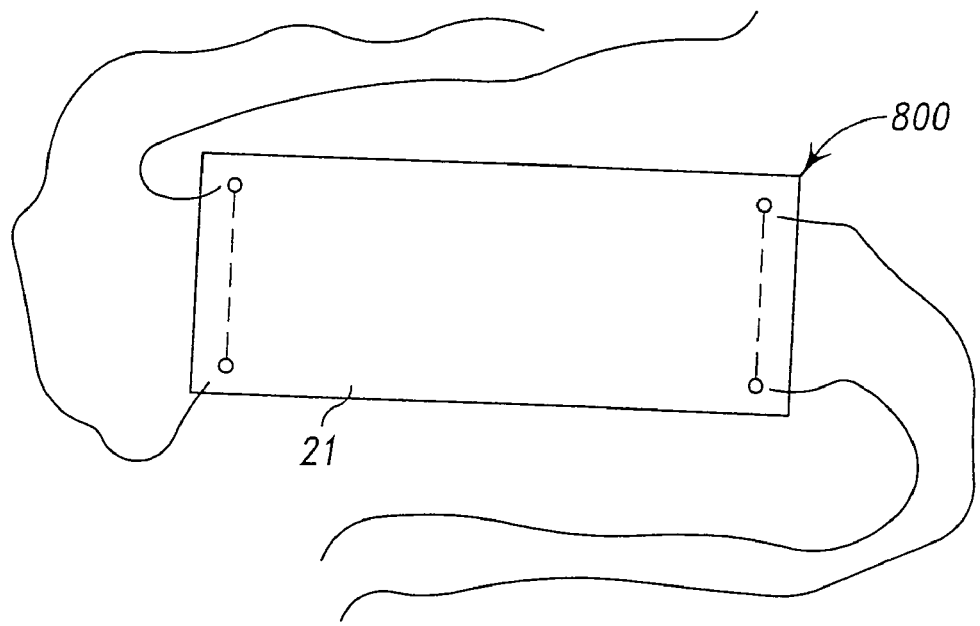
FIG. 61 is a top view of a device similar to those shown in FIGS. 56 and 57, except the device lacks a pillow of biological material.
Figure 62:
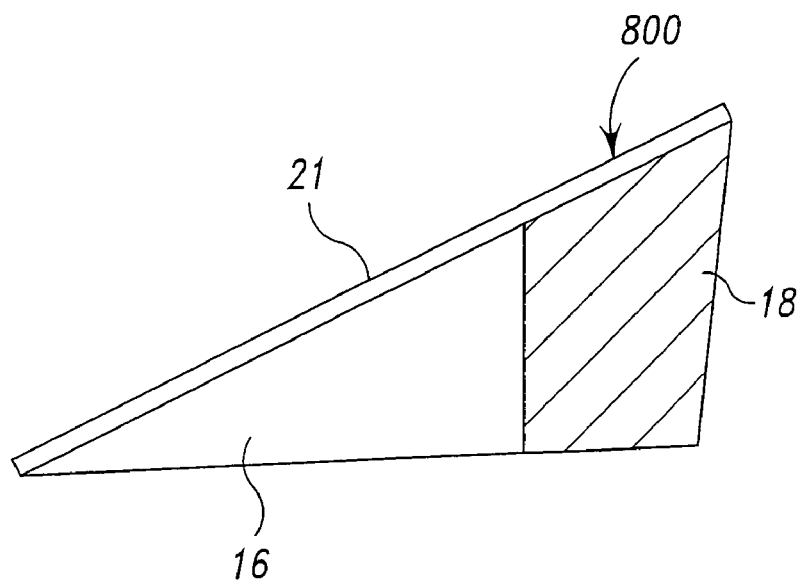
FIG. 62 is a cross-section showing the device of FIG. 61 in place covering a cavity left by a partial meniscectomy, with a discrete mass of biological material separately placed in the cavity.

FIGS. 61-62 show another implant device 800 that is not wedge shaped. In this embodiment, the base 21 comprises a toughened flat sheet, but in this case the device does not include any mass of biological material. As shown, device 800 is placed over space 16 and at least a portion of outer rim 18. If desired, a mass of biological material could be provided separately to fill the space 16 left by the partial meniscectomy, or could be injected to fill the cavity intraoperatively or post operatively. This embodiment can be fixed to native host tissue in the manners illustrated and described for the embodiment of FIGS. 56 and 57-58.

It should be appreciated that the ECM material described above may in some embodiments be combined with other materials. For example, the ECM material can be combined with a biocompatible polymer. Considering FIG. 8, the layers 58, 64 may include one or more layers of ECM and one or more layers of a biocompatible polymer. Unless otherwise called for in the claims, these layers 58, 64 could consist of a biocompatible polymer with ECM material provided for the mass 60; alternatively, the layers 58, 64 could comprise ECM material, or a mixture of ECM material and a biocompatible polymer, and the mass 60 could comprise a biocompatible polymer or a mixture of a biocompatible polymer and ECM material. In the embodiment of FIGS. 20-23, the compartments 190, 192, 194, 196 could be formed of a biocompatible polymer and filled with ECM material. Similar combinations of ECM material and biocompatible polymers can be used in the other illustrated embodiments of the invention. Accordingly, unless the claims are otherwise expressly limited to a particular material, both such types of materials should be considered as falling within the scope of the claims.

Although the invention has been described with reference to a device for regenerating a meniscus or portion of a meniscus, it should be understood that the principles of the invention can also be applied to produce devices for regenerating other intra-articular cartilage. For example, the principles of the invention can be applied to produce devices that are useful in regenerating other fibrocartilage, such as that present in the temporomandibular joint and between vertebrae. The principles of the invention may also be applied to produce devices for use in repair and regeneration of articular hyaline cartilage.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. A device for insertion into a space in a knee meniscus from which space a meniscus portion has been removed, the device comprising:
a shell defining an interior space, said shell comprising an extracellular matrix selected from the group consisting of small intestine submucosa, stomach submucosa, bladder submucosa, alimentary submucosa, respiratory submucosa, genital submucosa, and liver basement membrane that has been dehydrated by dehydrothermal cross-linking, wherein at least a portion of the dehydrothermal cross-linked extracellular matrix has a density of at least 0.9 gm/cm$^3$.

2. The device of claim 1 wherein a biological material is contained within the interior space of said shell.

3. An implantable device for regenerating at least a portion of a meniscus of a knee, the device comprising:
a dehydrated cover sheet and
a mass of extracellular matrix selected from the group consisting of small intestine submucosa, stomach submucosa, bladder submucosa, alimentary submucosa, respiratory submucosa, genital submucosa, and liver basement membrane, the dehydrated cover sheet extending over and beyond the mass of extracellular matrix, wherein at least a portion of the dehydrated cover sheet has a density of at least 0.9 gm/cm$^3$.

4. The implantable device of claim 3 wherein the extracellular matrix comprises small intestine submucosa.

5. The implantable device of claim 4 wherein the small intestine submucosa comprises at least one material selected from the group consisting of: comminuted small intestine submucosa, small intestine submucosa pieces, small intestine submucosa foam, an small intestine submucosa roll, woven small intestine submucosa, non-woven small intestine submucosa mat, braided small intestine submucosa, small intestine submucosa solution, small intestine submucosa dispersion, small intestine submucosa slurry, small intestine submucosa gel, small intestine submucosa paste, and small intestine submucosa that has not been toughened.

6. The implantable device of claim 3 wherein the cover sheet comprises at least one of the following: a biocompatible polymer and extracellular matrix selected from the group consisting of small intestine submucosa, stomach submucosa, bladder submucosa, alimentary submucosa, respiratory submucosa, genital submucosa, and liver basement membrane.

7. The implantable device of claim 3 further comprising at least one of the following: a bioactive agent, a biologically-derived agent, cells, a biological lubricant, a biocompatible polymer, and a biocompatible inorganic material.

8. The implantable device of claim 3 further comprising at least one biologically compatible material associated with the mass of extracellular matrix, said biologically compatible material selected from the group consisting of: a bioactive agent, a biologically-derived agent, cells, a biological lubricant, a biocompatible polymer, and a biocompatible inorganic material.

9. The implantable device of claim 3 wherein the cover sheet comprises a wedge-shaped body having an upper panel and a lower panel angularly separated to define an apex portion and a base portion.

10. The implantable device of claim 9 wherein the mass of extracellular matrix is positioned between the upper panel and lower panel.

11. The implantable device of claim 3 wherein the cover sheet has a toughness sufficient to at least temporarily withstand the forces of articulation at the knee without degrading.

12. The implantable device of claim 3 wherein the cover sheet is treated to increase its density.

13. The implantable device of claim 3 wherein the cover sheet has a density greater than the density of the mass of extracellular matrix.

14. An implantable device for regenerating at least a portion of a meniscus of a knee, the device comprising at least two adjacent dehydrated materials having different densities, wherein each of the materials comprises extracellular matrix selected from the group consisting of small intestine submucosa, stomach submucosa, bladder submucosa, alimentary submucosa, respiratory submucosa, genital submucosa, and liver basement membrane, wherein at least a portion of one of the dehydrated materials is treated to increase its density to a density of at least 0.9 gm/cm$^3$.

15. The implantable device of claim 14 wherein the extracellular matrix comprises small intestine submucosa.

16. The implantable device of claim 14 wherein one of the materials comprises a mass of biological material and the other material comprises a cover.

17. The implantable device of claim 14 wherein at least a portion of the other dehydrated materials has a density greater than 0.5 gm/cm$^3$ when dehydrated.

18. An implantable device for repairing or regenerating at least a portion of the tissue of a vertebrate, the device comprising a sheet of extracellular matrix selected from the group consisting of small intestine submucosa, stomach submucosa, bladder submucosa, alimentary submucosa, respiratory submucosa, genital submucosa, and liver basement membrane dehydrated to have a density of at least 0.9 gm/cm3, wherein the extracellular matrix has been dehydrated by dehydrothermal cross-linking.

19. The device of claim 18 wherein the dehydrothermal cross-linking comprises applying mechanical pressure to the extracellular matrix while using vacuum to remove water.

20. The device of claim 1 wherein the shell is formed as a wedge-shaped body having an upper panel and a lower panel angularly separated to define an apex portion and a base portion.

21. The device of claim 20 wherein the upper and lower panels have outer edges joined together by dehydrothermal cross-linking, said joined edges having a density of at least 0.9 gm/cm$^3$.

22. The device of claim 21 wherein a biological material is contained within the interior space.

23. The device of claim 22 wherein the biological material comprises fibrin, blood clot, platelet rich plasma, comminuted extracellular matrix or combinations thereof.

24. The device of claim 22 wherein the biological material comprises material selected from the group consisting of comminuted small intestine submucosa, small intestine submucosa pieces, small intestine submucosa foam, an small intestine submucosa roll, woven small intestine submucosa, non-woven small intestine submucosa mat, braided small intestine submucosa, small intestine submucosa solution, small intestine submucosa dispersion, small intestine submucosa slurry, small intestine submucosa gel, small intestine submucosa paste, and small intestine submucosa that has not been toughened.

25. The implantable device of claim 3 wherein the cover sheet comprises a biocompatible polymer and extracellular matrix selected from the group consisting of small intestine submucosa, stomach submucosa, bladder submucosa, alimentary submucosa, respiratory submucosa, genital submucosa, and liver basement membrane.

* * * * *